US009797815B2

(12) United States Patent
Cooper et al.

(10) Patent No.: US 9,797,815 B2
(45) Date of Patent: Oct. 24, 2017

(54) BREATH ANALYSIS SYSTEM

(71) Applicant: Pulse Health LLC, Portland, OR (US)

(72) Inventors: Steve Cooper, McMinnville, OR (US);
Neal Andrews, McMinnville, OR (US);
Martin Krauss, Fort Myers, FL (US);
Andrew E. King, Corvallis, OR (US);
Maura Mahon, Lake Oswego, OR (US); Weston Myler, McMinnville, OR (US); James Ingle, Corvallis, OR (US);
Gerald Thomas, Springfield, OR (US);
Rachel Dreilinger, Beavercreek, OR (US); David Barsic, Portland, OR (US);
Rick Myers, McMinnville, OR (US);
Craig Carlsen, Lake Oswego, CA (US); Scot Herbst, San Jose, CA (US);
Brian Young, Portland, OR (US);
Juven Lara, Portland, OR (US);
Charles Noll, Portland, OR (US)

(73) Assignee: Pulse Health LLC, Lake Oswego, OR (US)

( * ) Notice: Subject to any disclaimer, the term of this patent is extended or adjusted under 35 U.S.C. 154(b) by 135 days.

(21) Appl. No.: 14/754,534

(22) Filed: Jun. 29, 2015

(65) Prior Publication Data
US 2015/0377748 A1 Dec. 31, 2015

Related U.S. Application Data

(60) Provisional application No. 62/156,441, filed on May 4, 2015, provisional application No. 62/149,988, filed
(Continued)

(51) Int. Cl.
*G01N 1/22* (2006.01)
*G01N 33/497* (2006.01)
(Continued)

(52) U.S. Cl.
CPC .............. *G01N 1/22* (2013.01); *G01D 11/24* (2013.01); *G01N 21/6428* (2013.01);
(Continued)

(58) Field of Classification Search
CPC ...... G01N 1/22; G01N 33/98; G01N 33/4972; G01N 2001/2244; G01N 21/645
See application file for complete search history.

(56) References Cited

U.S. PATENT DOCUMENTS 3,094,511 A 6/1963 Hill, Jr. et al.
3,446,773 A 5/1969 Schwarz
(Continued)

FOREIGN PATENT DOCUMENTS

EP 2606820 A1 6/2013
EP 2641537 A1 9/2013
(Continued)

OTHER PUBLICATIONS

International Search Report and Written Opinion dated Sep. 23, 2015; PCT/US2015/038394.
(Continued)

*Primary Examiner* — David M Gray
*Assistant Examiner* — Andrew V Do
(74) *Attorney, Agent, or Firm* — Brownstein Hyatt Farber Schreck, LLP

(57) ABSTRACT

A breath analysis system that includes a handle assembly with an analysis cartridge on an upper end thereof. The handle includes a main body portion with a pressure opening and a pressure transducer therein. The analysis cartridge includes a main body portion with an upper portion that defines a breath chamber, a lower portion that defines a fluid chamber and a filter assembly that is movable between a breath capture position and an analysis position. The filter assembly has an opening defined therethrough. In the breath
(Continued)

capture position, the opening partially defines the breath chamber and in the analysis position the opening partially defines the fluid chamber. The system also includes an analysis device with a case, a door, a controller that controls the motor and a fluorescence detection assembly and a rotation assembly positioned in the case interior. The rotation assembly includes a shroud with a funnel portion for receiving the analysis cartridge.

15 Claims, 43 Drawing Sheets

Related U.S. Application Data on Apr. 20, 2015, provisional application No. 62/018,448, filed on Jun. 27, 2014.

(51) Int. Cl.
| | | |
|---|---|---|
| G01D 11/24 | (2006.01) | |
| G01N 33/52 | (2006.01) | |
| G01N 33/64 | (2006.01) | |
| G01N 21/64 | (2006.01) | |

(52) U.S. Cl.
CPC ....... *G01N 33/497* (2013.01); *G01N 33/4972* (2013.01); *G01N 33/52* (2013.01); *G01N 33/64* (2013.01); *G01N 21/645* (2013.01); *G01N 2001/2244* (2013.01); *G01N 2021/6482* (2013.01); *G01N 2033/4975* (2013.01); *G01N 2201/022* (2013.01); *G01N 2201/062* (2013.01); *G01N 2201/068* (2013.01); *Y10T 436/200833* (2015.01); *Y10T 436/202499* (2015.01)

(56) References Cited

U.S. PATENT DOCUMENTS

| | | | |
|---|---|---|---|
| 4,080,170 A | 3/1978 | Borkenstein | |
| 4,184,850 A | 1/1980 | Habenstein | |
| 4,340,470 A | 7/1982 | Van Mol | |
| 4,438,206 A | 3/1984 | Nakajima et al. | |
| 4,548,904 A | 10/1985 | Kent et al. | |
| 4,552,849 A | 11/1985 | Nakajima | |
| 4,950,317 A | 8/1990 | Dottermans | |
| 5,081,871 A | 1/1992 | Glaser | |
| 5,174,959 A | 12/1992 | Kundu et al. | |
| 5,254,261 A | 10/1993 | Tomaschke et al. | |
| 5,284,054 A | 2/1994 | Loebach | |
| 5,310,682 A | 5/1994 | Novotny et al. | |
| 5,462,061 A | 10/1995 | Malouvier | |
| 5,465,728 A | 11/1995 | Phillips | |
| 5,585,469 A | 12/1996 | Kojima et al. | |
| 5,739,535 A | 4/1998 | Koch et al. | |
| 5,801,059 A | 9/1998 | Smith et al. | |
| 5,924,994 A | 7/1999 | Harbrecht et al. | |
| 6,019,731 A | 2/2000 | Harbrecht et al. | |
| 6,023,982 A | 2/2000 | Basch et al. | |
| 6,136,608 A | 10/2000 | Kawachi | |
| 6,138,521 A | 10/2000 | Basch et al. | |
| 6,242,267 B1 | 6/2001 | Herron et al. | |
| 6,315,688 B1 | 11/2001 | McLaughlin et al. | |
| 6,462,128 B1 | 10/2002 | Barashkov et al. | |
| 6,582,376 B2 | 6/2003 | Baghdassarian | |
| 6,632,402 B2 | 10/2003 | Blazewicz et al. | |
| 6,835,431 B1 | 12/2004 | Alperovich et al. | |
| 7,032,431 B2 | 4/2006 | Baum et al. | |
| 7,087,434 B2 | 8/2006 | Chen et al. | |
| 7,101,716 B2 | 9/2006 | Nakano et al. | |
| 7,153,272 B2 | 12/2006 | Talton | |
| 7,220,387 B2 | 5/2007 | Flaherty et al. | |
| 7,312,071 B2 | 12/2007 | Lu et al. | |
| 7,347,825 B2 | 3/2008 | Vaughan et al. | |
| 7,352,465 B2 | 4/2008 | Fay et al. | |
| 7,384,793 B2 | 6/2008 | McCash et al. | |
| 7,432,298 B2 | 10/2008 | Lam et al. | |
| 7,514,265 B2 | 4/2009 | Yoon et al. | |
| 7,533,558 B2 | 5/2009 | Flaherty et al. | |
| 7,547,285 B2 | 6/2009 | Kline | |
| 7,560,574 B2 | 7/2009 | Habi et al. | |
| 7,790,467 B1 | 9/2010 | Massick | |
| 7,833,480 B2 | 11/2010 | Blazewicz et al. | |
| 7,992,422 B2 | 8/2011 | Leddy et al. | |
| 8,002,712 B2 | 8/2011 | Meka et al. | |
| 8,012,761 B2 | 9/2011 | Boga et al. | |
| 8,026,103 B2 | 9/2011 | Van Harpen et al. | |
| 8,181,503 B2 | 5/2012 | Flaherty et al. | |
| 8,198,097 B1 | 6/2012 | Pera | |
| 8,383,672 B2 | 2/2013 | Habi et al. | |
| 8,394,030 B2 | 3/2013 | Varga et al. | |
| 8,618,161 B2 | 12/2013 | Lam et al. | |
| 8,628,975 B2 | 1/2014 | Lam et al. | |
| 8,642,966 B2 | 2/2014 | Weckstrom et al. | |
| 8,772,487 B2 | 7/2014 | Chen et al. | |
| 8,778,693 B2 | 7/2014 | Boudenne et al. | |
| 8,809,531 B2 | 8/2014 | Bremberg et al. | |
| 8,821,409 B2 | 9/2014 | Ku et al. | |
| 8,950,240 B2 | 2/2015 | Yeh et al. | |
| 2001/0029340 A1 | 10/2001 | Mault | |
| 2002/0189457 A1 | 12/2002 | Dallas | |
| 2003/0164051 A1 | 9/2003 | Kumimune | |
| 2003/0208133 A1 | 11/2003 | Mault | |
| 2004/0017570 A1 | 1/2004 | Parikh et al. | |
| 2004/0162500 A1 | 8/2004 | Kline | |
| 2005/0084921 A1 | 4/2005 | Cranley et al. | |
| 2005/0227274 A1 | 10/2005 | Takahashi | |
| 2006/0073604 A1 | 4/2006 | Yoon et al. | |
| 2006/0266353 A1 | 11/2006 | Yamada et al. | |
| 2007/0062255 A1 | 3/2007 | Talton | |
| 2007/0093725 A1 | 4/2007 | Shaw | |
| 2008/0204705 A1 | 8/2008 | Liu | |
| 2008/0234553 A1 | 9/2008 | Urman et al. | |
| 2009/0159803 A1 | 6/2009 | Berthold et al. | |
| 2009/0162891 A1 | 6/2009 | Lu et al. | |
| 2010/0178662 A1 | 7/2010 | Urman et al. | |
| 2010/0256514 A1 | 10/2010 | Chazan et al. | |
| 2011/0003395 A1 | 1/2011 | Dey et al. | |
| 2011/0098590 A1 | 4/2011 | Garbutt et al. | |
| 2012/0004571 A1 | 1/2012 | Ku et al. | |
| 2012/0011918 A1 | 1/2012 | Bacal et al. | |
| 2012/0071342 A1 | 3/2012 | Lochhead et al. | |
| 2012/0105949 A1 | 5/2012 | Cummings et al. | |
| 2012/0165694 A1 | 6/2012 | Meka et al. | |
| 2012/0250024 A1 | 10/2012 | Noda | |
| 2012/0276651 A1 | 11/2012 | Kim et al. | |
| 2012/0302907 A1 | 11/2012 | Palmskog et al. | |
| 2013/0006068 A1 | 1/2013 | Gemer et al. | |
| 2013/0253336 A1 | 9/2013 | Haveri et al. | |
| 2013/0276509 A1 | 10/2013 | Rathke et al. | |
| 2013/0281873 A1 | 10/2013 | Evans et al. | |
| 2013/0288911 A1 | 10/2013 | Chen et al. | |
| 2013/0305808 A1 | 11/2013 | Yoo | |
| 2014/0171635 A1 | 6/2014 | Schwartz et al. | |
| 2014/0202234 A1 | 7/2014 | Burgon et al. | |
| 2014/0220696 A1 | 8/2014 | Schwartz et al. | |
| 2014/0373649 A1 | 12/2014 | Harrell et al. | |
| 2015/0073290 A1 | 3/2015 | Star et al. | |

FOREIGN PATENT DOCUMENTS

| | | |
|---|---|---|
| WO | 94/06057 | 3/1994 |
| WO | 96/38724 | 12/1996 |
| WO | 9965383 A1 | 12/1999 |
| WO | 20091094536 | 7/2009 |
| WO | 2010/009406 | 1/2010 |
| WO | 2012120140 | 9/2012 |
| WO | 2013115933 | 8/2013 |
| WO | 2013172873 | 11/2013 |

(56) References Cited

FOREIGN PATENT DOCUMENTS

| WO | 2014116604 | 7/2014 |
| WO | 2014/165184 | 10/2014 |

OTHER PUBLICATIONS

Mallya et al., "Organic Molecule Based Sensor for Aldehyde Detection," Abstract, Sensing Technology: Current Status and Trends III, Smart Sensors, Measurement and Instrumentation vol. 11, 2015, pp. 299-325. http://link.springer.com/chapter/10.1007%2F978-3-319-10948-0_15.
Fink, Johannes , Petroleum Engineer's Guide to Oil Field Chemicals and Fluids, First Edition, Gulf Professional Publishing, p. 188.
Marinho et al., "The reaction of o-phenylenediamine with ethoxymethylene compounds and aromatic aldehydes," ARKIVOC 2009 (xiv) pp. 346-361.
Dunn, Connie Dee, Automated Determination of Carbonyl Compounds in Organic Solvents, A Thesis in Chemistry, Aug. 1992.
Stejskal, Jaroslav, "Polymers of phylendiamines," Progress in Polymer Science, 41(2015) pp. 1-31.
International Search Report and Written Opinion issued on Mar. 25, 2016 in PCT/US15/38386.
Xu, et al. "Fluorescence Ratiometric Sensor for Trace Vapor Detection of Hydrogen Peroxide," Applied Materials and Interfaces, 2014, 6, 8708-8714; May 7, 2014.
International Search Report & Written Opinion dated Sep. 30, 2015; PCT/US2015/038389.
International Search Report & Written Opinion dated Sep. 30, 2015; PCT/US2015/038391.
International Search Report & Written Opinion dated Sep. 29, 2015; PCT/US2015/038392.

| Aldehyde (C#) | Relative Response to Hexanal (Counts-30 min) |
|---|---|
| C2 | 0.1275 |
| C3 | 0.1248 |
| C6 | 1.0000 |
| C10 | 1.3041 |

BREATH ANALYSIS SYSTEM

CROSS REFERENCE TO RELATED APPLICATIONS

This application claims the benefit of U.S. Provisional Application No. 62/156,441, filed May 4, 2015, U.S. Provisional Application No. 62/149,988, filed Apr. 20, 2015, and U.S. Provisional Application No. 62/018,448, filed Jun. 27, 2014, which are all incorporated by reference herein in their entireties.

FIELD OF THE INVENTION

The present invention is directed to the field of carbonyl detection and quantitation, and in particular the detection and quantitation of the concentration of carbonyl containing moieties in biological samples.

BACKGROUND OF THE INVENTION

The detection of carbonyl containing moieties is known but the precise detection of specific low concentrations of specific carbonyl containing moieties in biological samples is not known. The use of carbonyl's to induce the polymerization of o-phenylene diamine and p-phenylene diamine at high temperature is known to produce solid polymers for subsequent use in manufacturing products, but the use of phenylene diamine derivatives is not known to be used in methods to detect carbonyl containing moieties in a number of biological samples. In addition, measuring the fluorescence of a fluorogenic species in solution to determine the presence of molecules corresponding to the species is known, as well as the quantitation of the concentration of such molecules in a given sample. In addition, breath analysis device including for alcohol levels are known.

BRIEF DESCRIPTION OF THE DRAWINGS

FIG. 26 is a cross-sectional view of the breath analysis cartridge of FIG. 24 with the ampule assembly in elevation and the ampule member pushed in;

FIG. 26A is a cross-sectional view of the ampule assembly of the breath analysis cartridge;

SUMMARY OF THE PREFERRED EMBODIMENTS

Figure 1:
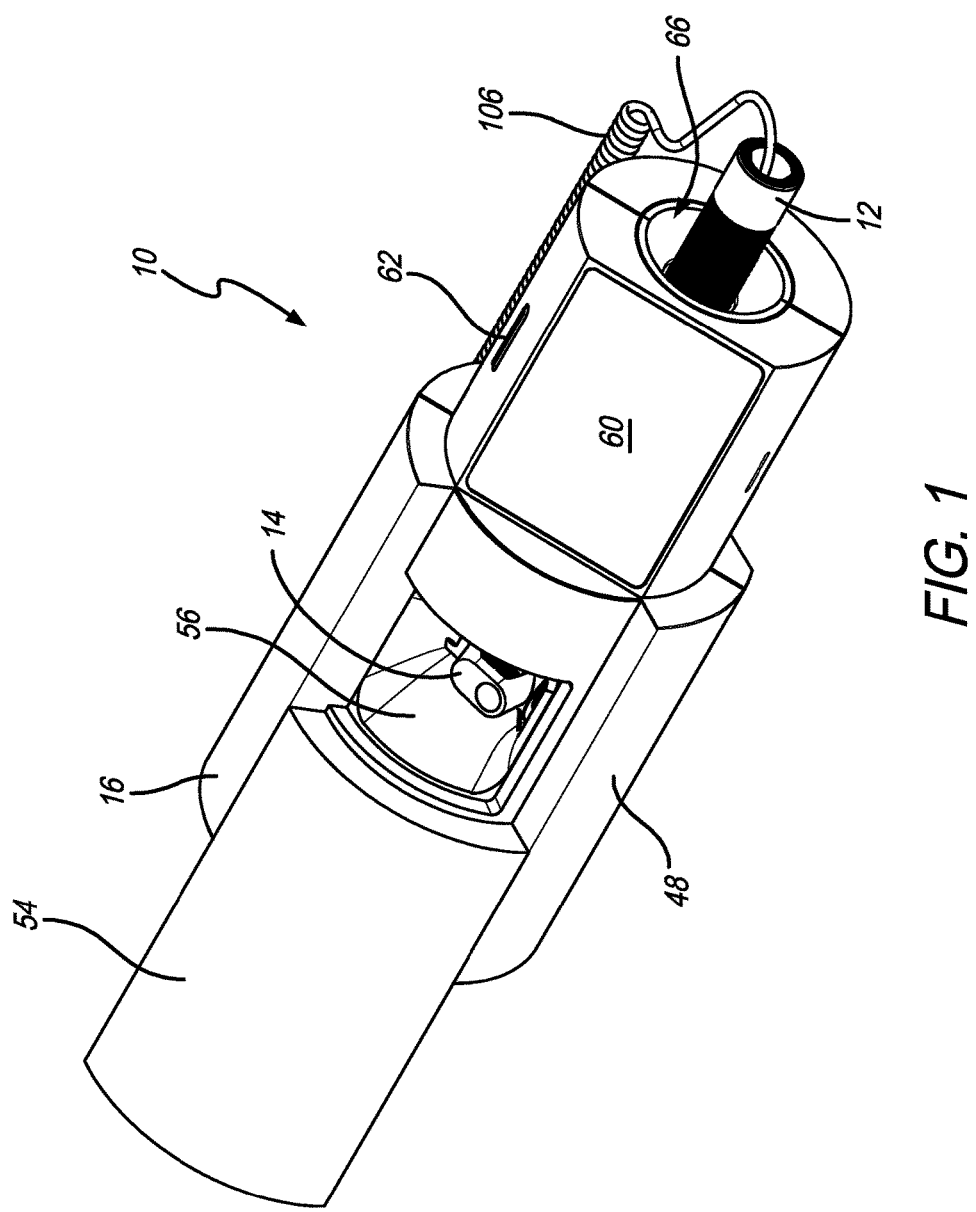
FIG. 1 is a perspective view of the breath analysis system in accordance with a preferred embodiment of the present invention with the door opened to show the analysis cartridge in the pocket.

In accordance with an aspect of the present invention there is provided an analysis cartridge that includes a main body portion having an upper portion that defines an upper chamber and a lower portion that defines a fluid chamber, and a filter assembly that is movable along a filter assembly path between a first position and a second position. The filter assembly has an opening defined therethrough. In the first position, the opening partially defines the upper chamber and in the second position the opening partially defines the fluid chamber. In a preferred embodiment, the filter assembly is movable within a cylindrical sleeve that extends from the upper chamber to the fluid chamber. Preferably, the sleeve includes a top opening such that an upper surface of the filter assembly is exposed to an exterior of the main body portion.

In a preferred embodiment, the filter assembly includes a cylindrically shaped filter holder that includes the opening extending transversely therethrough and two filters positioned such that they span the opening. The filters define a substrate space therebetween and a substrate is disposed in the substrate space. In a preferred embodiment, the substrate is silica and the fluid chamber includes an elution solution or rinse therein. Preferably, the upper chamber is a breath chamber that includes a breath entry opening, a breath exit opening and a breath path therebetween. In a preferred embodiment, the analysis cartridge includes a pressure measurement hole defined in a wall of the upper portion that communicates the breath chamber with a pressure tunnel that extends through the main body portion and to a pressure recess defined in the lower portion.

In a preferred embodiment, a phenylene diamine derivative is disposed in the analysis cartridge. Preferably, the analysis cartridge includes an ampule member having a fluorescence chromophore space with the phenylene diamine derivative disposed therein and the fluid chamber includes an elution solution disposed therein. The ampule member is movable between a first position where the phenylene diamine derivative is separated from the elution solution and a second position where the phenylene diamine derivative is disposed in the elution solution. In a preferred embodiment, the phenylene diamine derivative is m-phenylene diamine.

In accordance with an embodiment of the present invention there is provided a method that includes (a) obtaining an analysis cartridge that includes a main body portion having an upper portion that defines a breath chamber and a lower portion that defines a fluid chamber, and a filter assembly that is movable along a filter assembly path between a first position and a second position. The filter assembly has an opening defined therethrough and in the first position the opening partially defines the upper chamber and in the second position the opening partially defines the fluid chamber and the fluid chamber includes an elution solution therein, as described below. The method also includes (b) capturing a breath sample in the filter assembly, (c) moving the filter assembly from the first position to the second position, and (d) eluting constituents of the breath sample into the elution solution to form a constituent solution. In a preferred embodiment, prior to step (c) the method includes inserting the analysis cartridge into an analysis pocket, and rotating the analysis cartridge to an insertion position where an arm performs step (c).

In accordance with another embodiment of the present invention there is provided an analysis cartridge system that includes a breath analysis cartridge and a fluorescence analysis cartridge. The breath analysis cartridge includes a main body portion that includes an upper portion that defines a breath chamber and a lower portion that defines a fluid chamber. The breath chamber includes a breath entry opening, a breath exit opening and a breath path therebetween, and the lower portion includes a receiver member extending therefrom. The breath analysis cartridge also includes a filter assembly that is movable along a filter assembly path between a first position and a second position. The filter assembly has an opening defined therethrough, and, in the first position, the opening partially defines the breath chamber and is part of the breath path and in the second position the opening partially defines the fluid chamber. The fluorescence analysis cartridge includes a main body portion that includes an upper portion that defines an upper chamber and a lower portion that defines a fluid chamber. The upper chamber includes a front opening that is adapted to receive the receiver member of the breath analysis cartridge therein. The fluorescence analysis cartridge also includes a filter assembly that is movable along a filter assembly path between a first position and a second position The filter assembly has an opening defined therethrough, and, in the first position, the opening partially defines the upper chamber and in the second position the opening partially defines the fluid chamber. In a preferred embodiment, the in both the breath analysis cartridge and the fluorescence analysis cartridge the breath or upper chamber is sealed from the fluid chamber when the filter assembly is in the first position.

In a preferred embodiment, the breath analysis cartridge includes an ampule member that is slideable within a slide tube between the first and second positions. Preferably, the ampule member includes at least one opening therein that is sealed from fluid communication with the fluid chamber when the ampule member is in the first position, and is in fluid communication with the fluid chamber when the ampule member is in the second position. In a preferred embodiment, the filter assembly divides the upper chamber of the fluorescence analysis cartridge into a front chamber and a rear chamber. The front chamber includes a piercing member disposed therein that is adapted to pierce a breakable barrier of the ampule member. Preferably, the rear chamber of the fluorescence analysis cartridge includes an absorption member positioned therein.

In a preferred embodiment, the breath analysis cartridge includes a removable mouthpiece that defines a central opening that is in communication with the breath chamber. The mouthpiece includes a sleeve portion that is received in the breath entry opening and a mouthpiece portion. Preferably, the mouthpiece includes a stopper that abuts the main body portion. The stopper includes an alignment member extending therefrom that is received in an alignment opening in the main body portion. In a preferred embodiment, the fluorescence analysis cartridge includes opposing light entry and light exit windows positioned on opposite sides of the fluid chamber, and a fluorescence window positioned on the bottom of the main body portion. Preferably, the light entry and light exit windows each include an outer surface, and wherein the outer surfaces are parallel to one another. Preferably, the fluorescence window includes an outer surface and the outer surface of the fluorescence window is perpendicular to the outer surface of the light entry window.

In accordance with another embodiment of the present invention there is provided a method that includes obtaining an analysis cartridge system that includes a biological analysis cartridge and an identified constituent analysis cartridge. The biological analysis cartridge has an upper chamber and a fluid chamber, and the identified constituent analysis cartridge has an upper chamber and a fluid chamber. The method also includes capturing a biological sample as described below on a substrate as described below positioned in the upper chamber in the biological analysis cartridge, moving the substrate from the upper chamber to the fluid chamber, which includes a first elution solution therein as described below, eluting constituents of the biological sample into the first elution solution to form a constituent solution as described below, releasing a moiety into the second solution to form a first identifiable constituents solution, transferring the first identifiable constituents solution as described below to the upper chamber of the identified constituent analysis cartridge, such that identified constituents are captured on a substrate positioned in the upper chamber, moving the substrate from the upper chamber to a fluid chamber that includes a second elution solution therein as described below, and eluting the identified constituents into the second elution solution to form a second identifiable constituents solution as described below.

In a preferred embodiment, the biological analysis cartridge is a breath analysis cartridge, the identified constituent analysis cartridge is a fluorescence analysis cartridge, and the biological sample is a breath sample. Preferably, the moiety is a fluorescence chromophore as described below.

In accordance with another embodiment of the present invention there is provided a method of forming a solution within a breath analysis cartridge that includes a main body portion with an upper portion that defines a breath chamber a lower portion that defines a fluid chamber having an elution solution disposed therein and an ampule member that is movable between a first position and a second position. The ampule member includes a fluorescence chromophore space having a fluorescence chromophore disposed therein. The method includes moving the ampule member from the first position where the fluorescence chromophore space and fluorescence chromophore are separated from the fluid chamber to the second position where the fluorescence chromophore space is in communication with the fluid chamber, and mixing the fluorescence chromophore with the elution solution.

In accordance with another embodiment of the present invention there is provided an analysis cartridge that includes a main body portion that includes an upper portion that defines a breath chamber and a lower portion that defines a fluid chamber. The breath chamber includes a breath entry opening, a breath exit opening and a breath path therebetween. The analysis cartridge also includes a filter assembly that is movable along a filter assembly path between a first position and a second position. The filter assembly has an opening defined therethrough, and, in the first position, the opening partially defines the breath chamber and is part of the breath path and in the second position the opening partially defines the fluid chamber. In a preferred embodiment, the filter assembly includes first and second filters positioned in the opening and the first and second filters define a substrate space therebetween with a substrate disposed therein. Preferably, the substrate is incorporated with an active reactive capture agent. In a preferred embodiment, the active reactive capture agent is a fluorescent hydrazine or aminooxy compound.

In accordance with another embodiment of the present invention there is provided a method of forming a fluorescing solution within an analysis cartridge that includes a main body portion with an upper portion that defines a breath chamber, a lower portion that defines a fluid chamber having an elution solution disposed therein and a filter assembly that is movable along a filter assembly path between a first position and a second position. The filter assembly has an opening defined therethrough, and, in the first position, the opening partially defines the breath chamber and in the second position the opening partially defines the fluid chamber. The filter assembly includes a substrate incorporated with an active reactive capture agent disposed therein. The method includes capturing carbonyl containing moieties on the substrate, moving the filter assembly from the first position to the second position, and eluting the carbonyl containing fluorescence chromophores and active reactive capture agent into the elution solution to form the fluorescing solution.

In accordance with another embodiment of the present invention there is provided a breath capture assembly that includes a handle assembly having an elongated main body portion that defines a handle interior, a cap disposed at an end of the main body portion that includes a pressure opening defined therein, and a pressure transducer disposed in the handle interior. The breath capture assembly also includes an analysis cartridge received on an upper end of the handle assembly. The analysis cartridge includes a main body portion that has an upper portion that defines a breath chamber and a lower portion that defines a fluid chamber. The breath chamber includes a breath entry opening, a breath exit opening and a breath path therebetween. The analysis cartridge includes a filter assembly that is movable along a filter assembly path between a first position and a second position. The filter assembly has an opening defined therethrough, and, in the first position, the opening partially defines the breath chamber and is part of the breath path and in the second position the opening partially defines the fluid chamber.

In a preferred embodiment, the pressure measurement hole is defined in a wall of the upper portion of the analysis cartridge and communicates the breath chamber with a pressure tunnel that extends through the main body portion.

A pressure path is defined from the breath chamber, through the pressure measurement hole, the pressure tunnel, the pressure opening and to the pressure transducer. Preferably, the cap of the handle assembly includes a pressure protrusion extending upwardly therefrom that is sealingly received in a pressure recess in the analysis cartridge. The pressure recess is in communication with the pressure tunnel, and the pressure opening is defined in the pressure protrusion. In a preferred embodiment, the cap includes a seat defined therearound, and a collar depending downwardly from the analysis cartridge is received on the seat. The cap preferably includes an attachment protrusion extending radially outwardly therefrom that is received in an attachment recess defined in the collar of the analysis cartridge.

In a preferred embodiment, a hollow extension tends downwardly from the cap of the handle assembly and into the handle interior. The hollow extension is part of the pressure path. Preferably, a pressure tube is received on the hollow extension and is in the pressure path between the hollow extension and the pressure transducer.

In a preferred embodiment, the analysis cartridge includes a breakable barrier disposed between the breath chamber and the fluid chamber when the filter assembly is in the first position to seal the breath chamber from the fluid chamber.

In accordance with another embodiment of the present invention there is provided an analysis device that includes a case defining a case interior, a door movable between an open and a closed position, and a rotation assembly positioned in the case interior that includes first and second fixed members and a rotatable portion positioned between the first and second fixed members. The rotatable portion is rotatable about a rotation axis with respect to the first and second fixed members. The rotatable portion includes a shroud that has a funnel portion defined therein for receiving an object to be rotated. The shroud includes a pocket opening defined at the top thereof and the rotation assembly includes a fluorescence detection assembly positioned generally below the shroud. The analysis device also includes a motor that drives rotation of the rotatable portion and a controller that controls the motor and the fluorescence detection assembly.

In a preferred embodiment, the shroud includes a pocket opening and an analysis opening opposite to one another, and the shroud includes walls that taper between the pocket opening and the analysis opening. The fluorescence detection assembly preferably includes a housing that has an analysis cartridge receiving portion with a well defined therein that is aligned with the analysis opening in the shroud to form an analysis pocket. In a preferred embodiment, the analysis cartridge receiving portion cooperates with the shroud to define a light entry aperture, a light exit aperture and a fluorescence aperture. Preferably, the fluorescence detection assembly includes a light that is configured to be directed along a light path that extends through a light chamber defined in the housing, through the light entry aperture, through the light exit aperture, and into a light trap.

In a preferred embodiment, the fluorescence detection assembly includes a detector for receiving fluorescence emitted through the fluorescence opening and through a fluorescence chamber defined in the housing. Preferably, the fluorescence chamber is generally orthogonal to the light chamber. In a preferred embodiment, the analysis device includes an arm that is pivotal between a stowed position and a deployed position. The arm includes a first end that extends through an arm opening defined in the shroud when in the deployed position. When the rotatable portion rotates from a start position to an insertion position the arm pivots from the stowed position to the deployed position. In a preferred embodiment, the arm is biased toward the stowed position and includes a second end that is operationally associated with a cam surface on the second fixed member. The cam surface preferably has a stowed end that is associated with the stowed position of the arm and a deployed end that is associated with the deployed end of the arm and includes an increasing radius from the stowed end to the deployed end. In a preferred embodiment, the arm includes a ball bearing on the second end thereof that interacts with the cam surface. Preferably, the arm is pivotal on a shaft that extends from the shroud.

In accordance with another embodiment of the present invention there is provided a rotation assembly that includes first and second fixed members, and a rotatable portion positioned between the first and second fixed members that is rotatable about a rotation axis with respect to the first and second fixed members. The rotatable portion includes a shroud that has a funnel portion defined therein for receiving an object to be rotated and an arm that is pivotal between a stowed position and a deployed position. The arm includes a first end that extends through an arm opening defined in the shroud when in the deployed position. The analysis device also includes a motor that drives rotation of the rotatable portion. When the rotatable portion is rotated from a start position to an insertion position the arm pivots from the stowed position to the deployed position. In a preferred embodiment, the shroud includes a pocket opening and an analysis opening opposite to one another and walls that taper between the pocket opening and the analysis opening.

In a preferred embodiment, the shroud includes first and second axle members extending outwardly therefrom that are received in opening in the first and second fixed members, respectively. Preferably, the shroud includes at least one internally threaded fastener receiver member extending therefrom. The housing of the fluorescence detection assembly includes at least one receiver tube and a threaded receiver extends through the receiver tube and into the fastener receiver member to secure the shroud to the housing. Preferably, the housing includes first and second housing halves. A first receiver tube is located on the first housing half and a second receiver tube is located on the second housing half. The threaded receiver extends through the first and second receiver tubes and into the fastener receiver member to secure the shroud to the housing.

In accordance with another embodiment of the present invention there is provided a handle assembly for use with a breath analysis system that includes an analysis cartridge and an analysis device. T handle includes an elongated main body portion that defines a handle interior, a cap disposed at an end of the main body portion that includes a pressure opening defined therein, a pressure transducer disposed in the handle interior, and a pressure path defined between the pressure opening and the pressure transducer. In a preferred embodiment, the cap includes a pressure protrusion extending upwardly therefrom and the pressure opening is defined in the pressure protrusion. Preferably, the handle interior includes a magnet disposed therein that interacts with a magnet in the analysis device. The magnet is positioned in a magnet recess defined in the cap.

In accordance with another embodiment of the present invention there is provided a filter assembly that includes a main body portion having a generally cylindrical shape that defines a first axis, an opening defined transversely through the main body portion that extends generally perpendicularly to the first axis, first and second filters spanning the opening and defining a substrate space therebetween, and a substrate disposed in the substrate space. Preferably, the first and second filters comprise a plastic having pores defined therethrough. In a preferred embodiment, the main body portion includes guide rails on an outside surface thereof that extend generally parallel to the axis. Preferably, the main body portion includes a lower surface that includes at least one piercer extending downwardly therefrom.

In accordance with another embodiment of the present invention there is provided a method of making a filter assembly that includes obtaining a filter holder having a main body portion with a generally cylindrical shape that defines a first axis and includes an opening defined transversely through the main body portion that extends generally perpendicularly to the first axis, dosing a first filter with a substrate, pressing a second filter onto the substrate, and positioning the first filter, substrate and second filter into the opening such that the first and second filter span the opening. The first and second filters and substrate can be positioned in the opening together or separately.

In accordance with another embodiment of the present invention there is provided a fluorescence detection assembly that includes an emitter, a detector, a housing that defines an light chamber, a fluorescence chamber and a well, a light path that extends from the emitter, through the light chamber and through the well, and a fluorescence path that extends from the well, through the fluorescence chamber and to the detector. In a preferred embodiment, the fluorescence detection assembly includes a first lens and a first filter positioned within the light path. Preferably, the fluorescence detection assembly includes second lens and a second filter positioned within the fluorescence path. In a preferred embodiment, the fluorescence detection assembly includes at least one of a first light baffle positioned within the light path between the emitter and the first lens, a second light baffle positioned within the light path between the first lens and the first filter and a third light baffle positioned within the light path between the first filter and the well. The first baffle includes a first light baffle aperture defined therein that has a smaller inner diameter than an inner diameter of the light chamber. The second baffle includes a second light baffle aperture defined therein that has a smaller inner diameter than the inner diameter of the first light baffle aperture. The third baffle includes a third light baffle aperture defined therein that has a smaller inner diameter than the inner diameter of the second light baffle aperture.

In a preferred embodiment, the light trap is positioned at a distal end of the light path and includes a first wall that is angled between about 25° and about 45° with respect to the light path. Preferably, the light trap includes a second wall connected to the first wall and the second wall is not perpendicular to the light path. In a preferred embodiment, the housing is comprised of an upper housing half and a lower housing half and the lower housing half includes an analysis cartridge receiving portion that defines the well. In a preferred embodiment, the upper housing half includes a flange that extends downwardly therefrom and overlaps a flange extending upwardly from the lower housing half. In a preferred embodiment, an analysis cartridge is positioned in the well that includes a light entry window, a light exit window and a fluorescence window. The light entry window and light exit window are positioned along the light path.

In a preferred embodiment, the housing is comprised of an upper housing half and a lower housing half that cooperate to define a first lens pocket that houses the first lens, a first filter pocket that houses the first filter, a second lens pocket that houses the second lens, and a second filter pocket that houses the second filter. Preferably, the fluorescence detection assembly includes a shroud connected to the housing that includes a pocket opening and an analysis opening opposite to one another and a funnel portion therebetween. The funnel portion cooperates with the well to define an analysis pocket and the shroud at least partially defines the light entry aperture and the fluorescence aperture.

In accordance with another embodiment of the present invention there is provided a method of detecting fluorescence that includes emitting light from an emitter into an light chamber and along a light path that includes a sensing chamber therealong. The sensing chamber includes a fluorescing solution therein. The emitted light passes through the fluorescence solution and produces a fluorescence light, and wherein the fluorescence light is emitted from the sensing chamber into a fluorescence chamber along a fluorescence path, and detecting a fluorescence signal of the fluorescence light.

In accordance with another embodiment of the present invention there is provided a method of detecting fluorescence that includes inserting an analysis cartridge into an analysis pocket. The analysis cartridge includes a filter assembly that includes a substrate having a carbonyl containing moiety thereon. The method also includes rotating the analysis cartridge from a start position to an insertion position, moving the filter assembly within the analysis cartridge from an upper chamber to a fluid chamber that contains an elution solution, rotating the analysis cartridge from the insertion position to an analysis position such that the elution solution drains through the filter assembly and the carbonyl containing moiety is eluted into the elution solution to form a fluorescing solution, and analyzing the fluorescence of the fluorescing solution.

In accordance with another embodiment of the present invention there is provided a breath analysis system that includes a breath capture assembly that includes a handle assembly that includes an elongated main body portion that defines a handle interior, a pressure opening defined in an end of the elongated main body portion, and a pressure transducer disposed in the handle interior. The breath analysis system also includes an analysis cartridge received on an upper end of the handle assembly. The analysis cartridge includes a main body portion that includes an upper portion that defines a breath chamber, and a lower portion that defines a fluid chamber. The breath chamber includes a breath entry opening, a breath exit opening and a breath path therebetween. The analysis cartridge includes a filter assembly that is movable along a filter assembly path between a breath capture position and an analysis position. The filter assembly has an opening defined therethrough, and, in the breath capture position, the opening partially defines the breath chamber and is part of the breath path and in the analysis position the opening partially defines the fluid chamber. The system also includes an analysis device that includes a case defining a case interior, a door movable between an open and closed position, and a rotation assembly positioned in the case interior that includes a shroud that has a funnel portion defined therein for receiving the analysis cartridge. The system also includes a controller that controls the motor and the fluorescence detection assembly. The pressure transducer is in communication with the controller.

In accordance with another embodiment of the present invention there is provided a method for detecting and quantifying carbonyl containing moieties in breath. The method includes (a) providing an analysis cartridge, (b) connecting the analysis cartridge to a handle assembly, (c) collecting a breath sample of carbonyl containing moieties on a filter assembly, (d) labeling the carbonyl containing moieties to provide a labeled solution, (e) inserting the labeled solution into an analysis device, (f) directing light within a predetermined wavelength range through the labeled solution, thereby producing a fluorescence, and (g) detecting the fluorescence.

It will be appreciated that any biological sample can be analyzed using the system. Breath constituents other than carbonyl containing moieties (CCM) or aldehydes can be captured and analyzed as desired. U.S. Patent Publication Nos. 2003/0208133 and 2011/0003395 are incorporated by reference herein in their entireties.

DETAILED DESCRIPTION OF THE PREFERRED EMBODIMENTS

The following description and drawings are illustrative and are not to be construed as limiting. Numerous specific details are described to provide a thorough understanding of the disclosure. However, in certain instances, well-known or conventional details are not described in order to avoid obscuring the description. References to one or another embodiment in the present disclosure can be, but not necessarily are, references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. Appearances of the phrase "in one embodiment" in various places in the specification do not necessarily refer to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "top," "bottom," "side," "short," "long," "up," "down," and "below" used herein are merely for ease of description and refer to the orientation of the components as shown in the figures. It should be understood that any orientation of the components described herein is within the scope of the present invention.

FIGS. 1-30 show a breath analysis system 10 for analyzing carbonyl containing moieties ("CCM") in a patient's breath. As shown in FIG. 1, the system 10 generally includes a handle assembly 12, an analysis cartridge 14 and an analysis device 16. Generally, the handle assembly 12 and analysis cartridge 14 are used by the clinician and patient to capture certain components of the patient's breath (as described more fully below), and the analysis device 16 is used to analyze the captured components.

The analysis cartridge 14 shown in FIGS. 2-7 and 21A-23 will now be described. In a preferred embodiment, the analysis cartridge 14 includes a main body portion 11 that includes an upper portion 29 that defines an upper or breath chamber 30 and a lower portion 31 that defines a lower or fluid chamber 32. The breath chamber 30 includes a front opening or breath entry opening 33, a breath exit opening 40 and a breath path P1 therebetween. In a preferred embodiment, the breath chamber 30 tapers toward the breath exit opening 40, however, this is not a limitation. The analysis cartridge 14 also includes a filter assembly 19 that is movable along a filter assembly path P2 between a first or breath capture position (FIG. 2) and a second or analysis position (FIG. 21E). The filter assembly 19 has an opening 17 defined therethrough that includes at least one and preferably two filters 26 positioned therein. In the breath capture position the opening 17 partially defines the breath chamber 30 and is part of the breath path P1 and in the analysis position the opening 17 partially defines the fluid chamber 32.

Figure 3A:
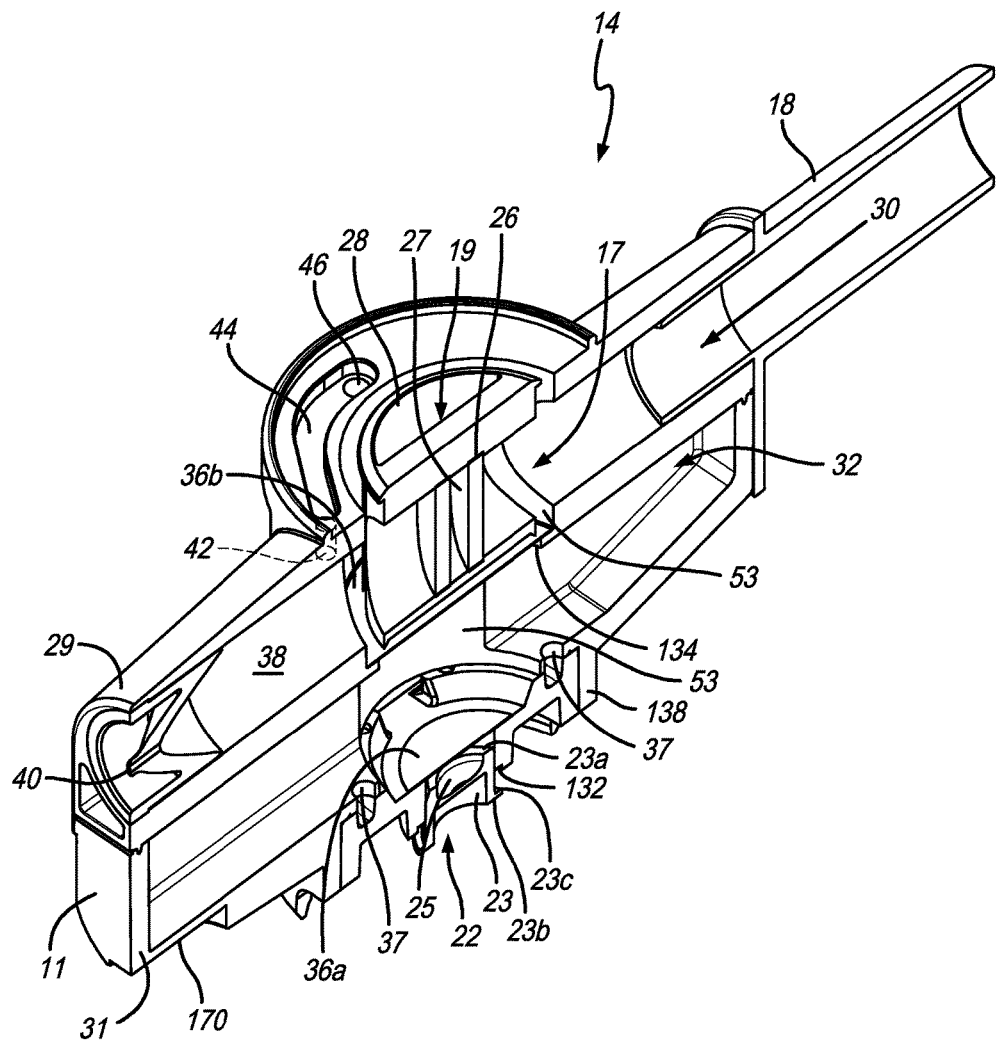
FIG. 3A is a cross-sectional perspective view of the analysis cartridge.
Figure 3B:
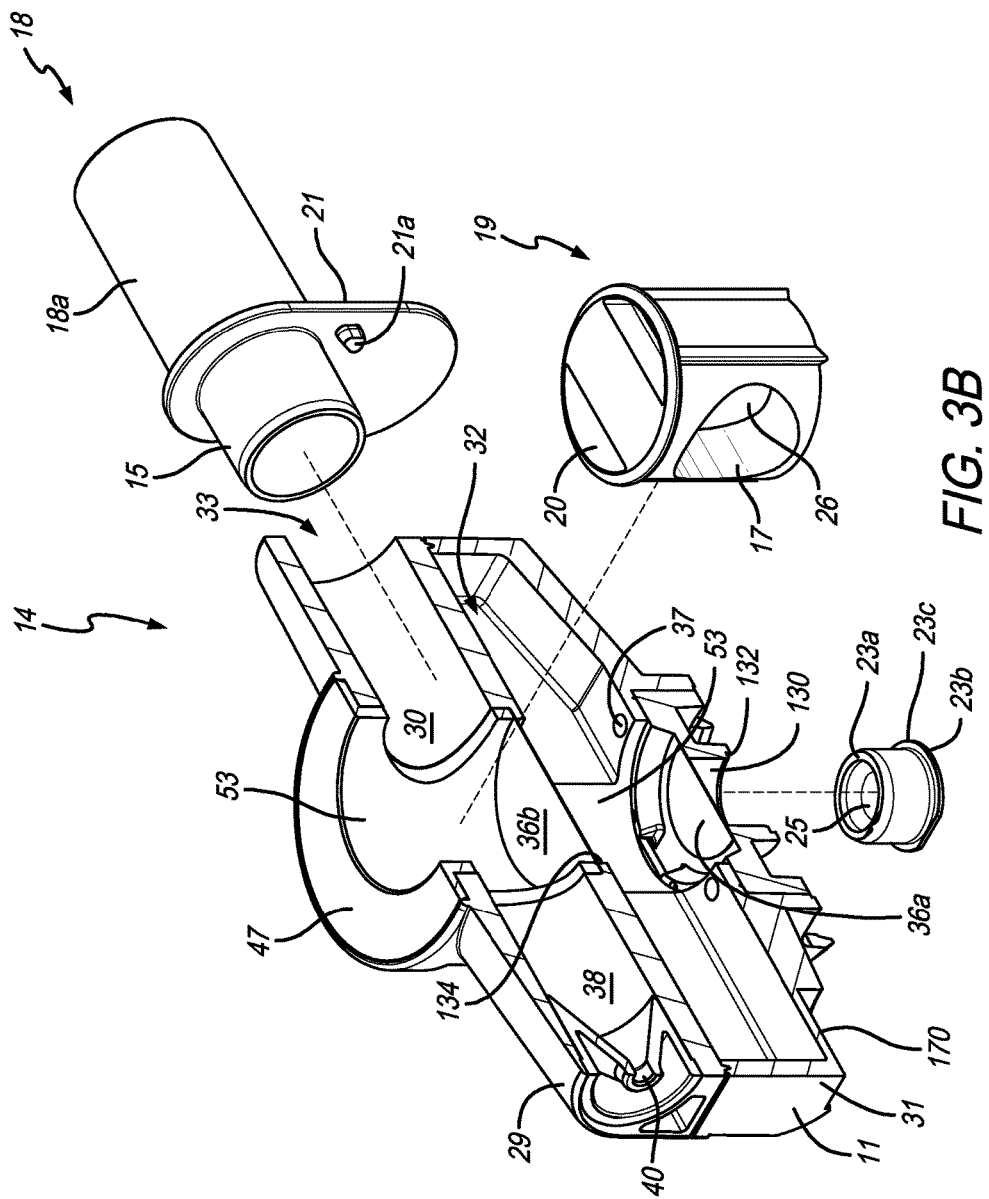
FIG. 3B is a cross-sectional exploded perspective view of the analysis cartridge.

In a preferred embodiment, the analysis cartridge 14 includes a removable mouthpiece 18, the filter assembly 19 on the top and an ampule member 22 on the bottom. As shown in FIG. 3B, the mouthpiece 18 includes a sleeve portion 15 that is received in breath entry opening 33 on the main body portion 11, a mouthpiece portion 18a, a stopper 21 that abuts the main body portion 11 and an alignment member 21a that is received in a complementary alignment opening in the main body portion 11 (not shown). The mouthpiece 18 partially defines the breath chamber 30 and the breath path P1. The filter assembly 19 preferably includes two filters or frit plates 26 (sometimes referred to together as a frit stack) that are held by a frit holder 20. The frit plates 26 span opening 17.

Figure 2:
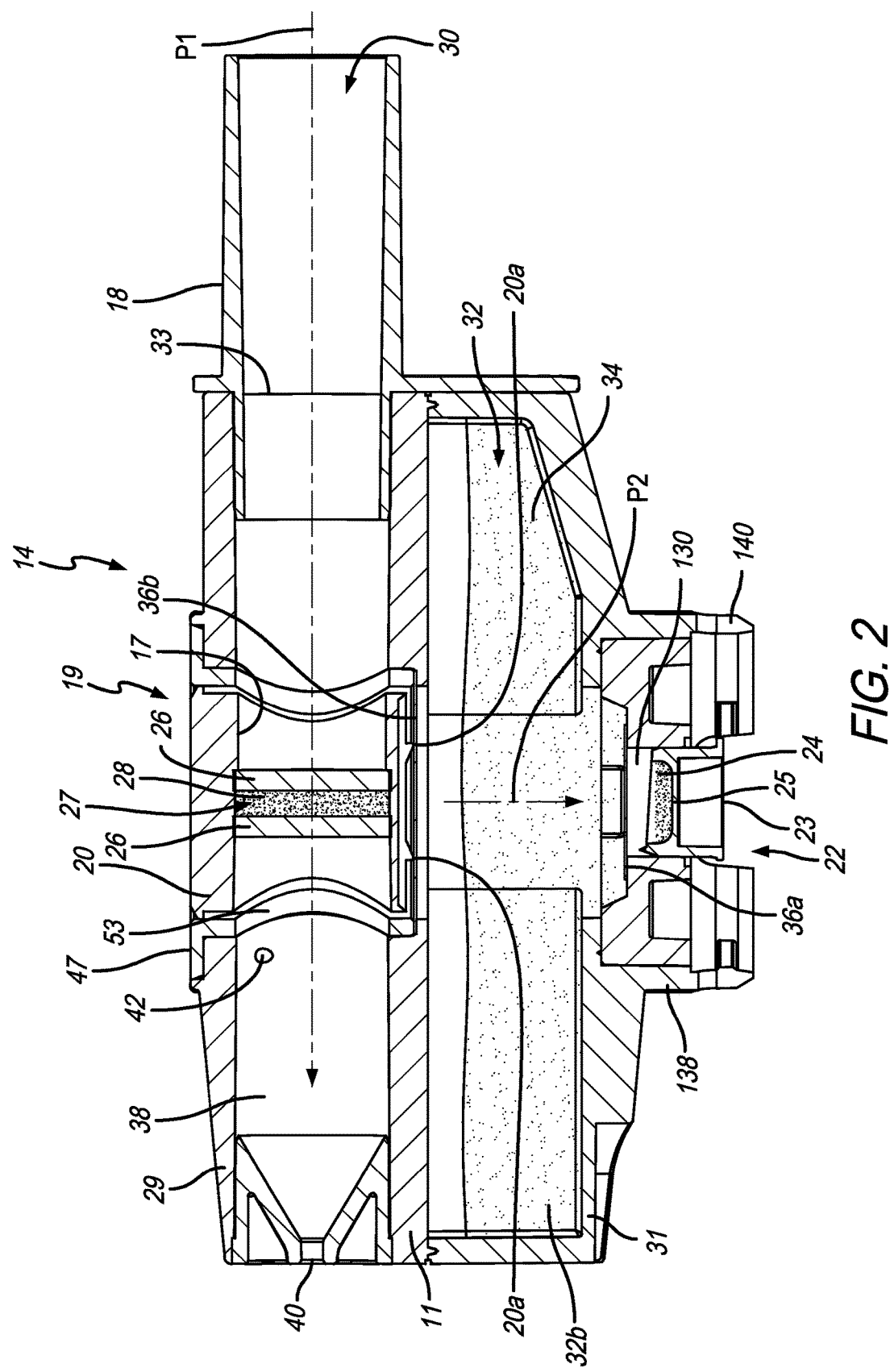
FIG. 2 is a cross-sectional elevational view of the analysis cartridge.

In a preferred embodiment, the frit holder 20 includes at least one piercer 20a on the bottom surface thereof for piercing a breakable barrier discussed below. Preferably, the frit holder 20 includes at least one guide rail 39 on an outside surface for helping guide the frit assembly 19 as it is moved along the filter assembly path. The piercer 20a can be on the bottom of the guide rail 39. Prior to use, the frit stack 26 is positioned in the breath chamber 30. As shown in FIG. 2, a substrate space 27 is defined between the frit plates 26. In a preferred embodiment, a substrate 28, such as silica, is disposed in the substrate space 27 between the frit plates 26.

It will be appreciated that the frit plates 26 are sufficiently porous so that the breath can pass therethrough, but not so porous that the substrate 28 trapped therebetween can escape. The filters or frit plates 26 are preferably made of polyethylene spheres that are pressed and packed together in a form. When pressed together in the disc or plate shape, the spherical or roundish shape creates the voids or pores necessary for breath to get through. The spheres can be made out of different plastic materials (e.g., polyethylene, polypropylene, etc.) or teflon in different diameters. In another embodiment, the filters 26 can comprise spheres all made of the same plastic materials and of the same or different diameters. In an exemplary embodiment, the frits 26 are polyethylene or teflon frits with 10 µm or 20 µm pore sizes. As is described more fully below, in use, as a patient blows through the breath chamber 30, CCM including aldehydes, collect on the substrate 28 (also referred to as CCM capture material). In a preferred embodiment, silica is used as the substrate or CCM capture material. However, this is not a limitation on the present invention and other substrates with the ability to capture CCM or aldehydes can be used.

In a preferred embodiment, the frit plates or filters 26 that span opening 17 are preferably press fit therein. The method of creating the filter assembly includes pressing the spherical plastic pieces into first and second filters 26, pressing the first filter 26 into the opening 17 in the frit holder 20. Then, the substrate 28 (preferably silica) is dosed on the first frit 26, a second filter 26 is then pressed into the opening 17 onto the silica 28 using a predefined pressure. In another embodiment, the silica 28 can be dosed onto the first frit 26 and then the second frit 26 can be pressed onto the silica 28 to create a frit stack, prior to pressing the frit stack into the opening 17 in the frit holder 20. In another embodiment, the filters can be disposed in grooves defined in the inside wall of the frit holder 20.

As shown in FIGS. 2-3B, the ampule member 22 comprises a main body portion 23 having a fluorescence chromophore space or trough 25 defined therein that includes an upper rim 23a and a lower surface 23b. The trough 25 includes a phenylene diamine derivative ("PD derivative") 24 disposed therein. The ampule member 22 is movable between a first position where the trough 25 and PD derivative 24 are separated from the fluid chamber 32 by a first breakable barrier 36a and a second position where the trough 25 is in communication with the fluid chamber 32 (where the PD derivative 24 and elution solution 34 are mixed in the fluid chamber 32, as described below). The breakable barrier 36a can be a foil or the like. In a preferred embodiment, the ampule member 22 is movable within an ampule tunnel 130 that is defined in the lower portion 31 of the analysis cartridge 14. In a preferred embodiment, the ampule member 22 includes a flange or stopper 23c that abuts a stopper surface 132 on the analysis cartridge 14 when the ampule member 22 is moved to the second position. The stopper 23c prevents the ampule member 22 from moving too far into the ampule tunnel 130 and/or into the fluid chamber 32. In a preferred embodiment the ampule tunnel 130 is orthogonal to the fluid chamber 32. However, this is not a limitation.

As shown in FIGS. 2-3B, the fluid chamber 32 is located between the breath chamber 30 and the ampule member 22 and ampule tunnel 130. An elution solution 34 is disposed in the fluid chamber 32. In a preferred embodiment, the elution solution 34 includes water and ethanol, however, this is not a limitation on the present invention. In a preferred embodiment, the fluid chamber 32 is sealed from the ampule tunnel 130. This can be done by any sealing method. In a preferred embodiment, the fluid chamber 32 is sealed from the ampule tunnel 130 by first breakable barrier 36a. In a preferred embodiment, the fluid chamber 32 is sealed from the breath chamber 30. This can be done by any sealing method. In a preferred embodiment, a second breakable barrier 36b positioned across the filter assembly pathway P2 (dividing the filter assembly sleeve 53) between the breath chamber 30 and the fluid chamber 32. The opening between the fluid and breath chambers is referred to herein as the filter assembly opening 134 and it includes a ledge on which the second breakable barrier 36b is secured. The fluid chamber 32 also includes vent holes 37 to keep the elution solution 34 from getting "air locked" during mixing.

It will be appreciated by those of skill in the art that before use of the analysis cartridge 14 (i.e., before it is attached or connected to the handle assembly 12), the filter assembly 19 is in the breath capture position and the ampule member 22 is in the first position. In this configuration, the elution solution 34 in the fluid chamber 32 is separated from the filter assembly 19 in the breath chamber 30 by second breakable barrier 36b and the ampule member 22 in the ampule tunnel 130 by first breakable barrier 36a.

Figure 4:
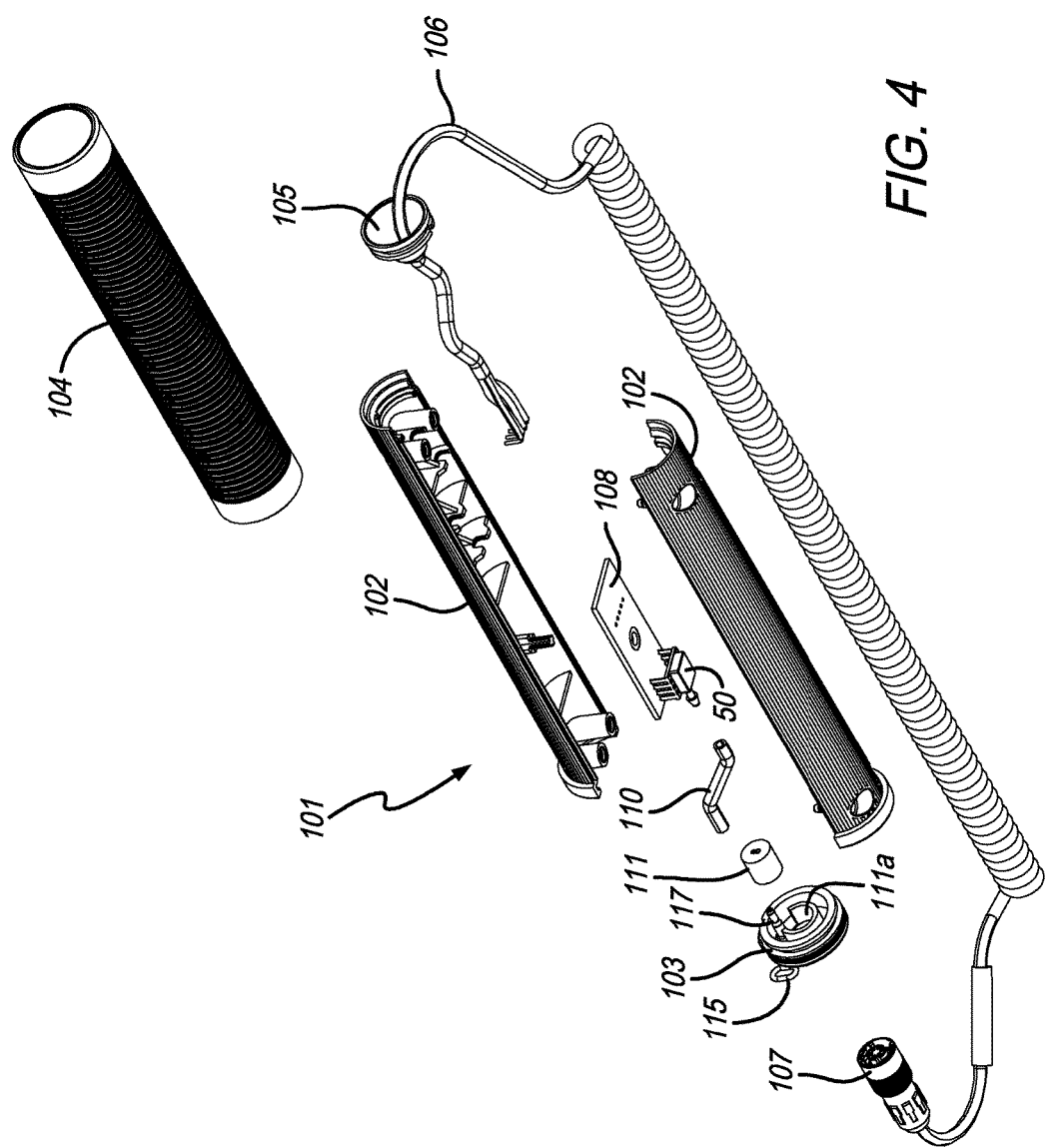
FIG. 4 is an exploded view of the handle assembly.
Figure 5A:
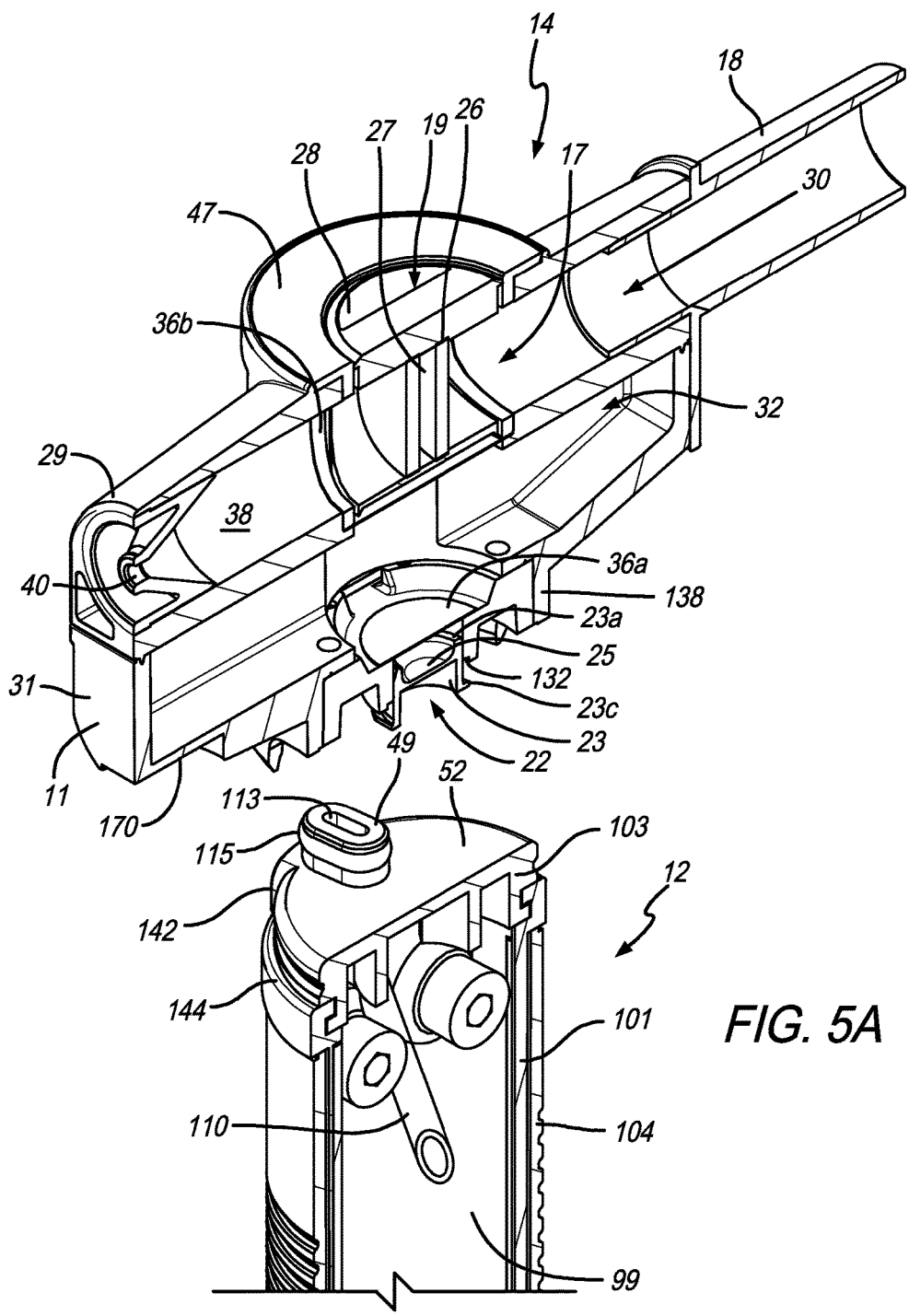
FIG. 5A is a cross-sectional perspective view of the analysis cartridge prior to being connected to the handle assembly.
Figure 5B:
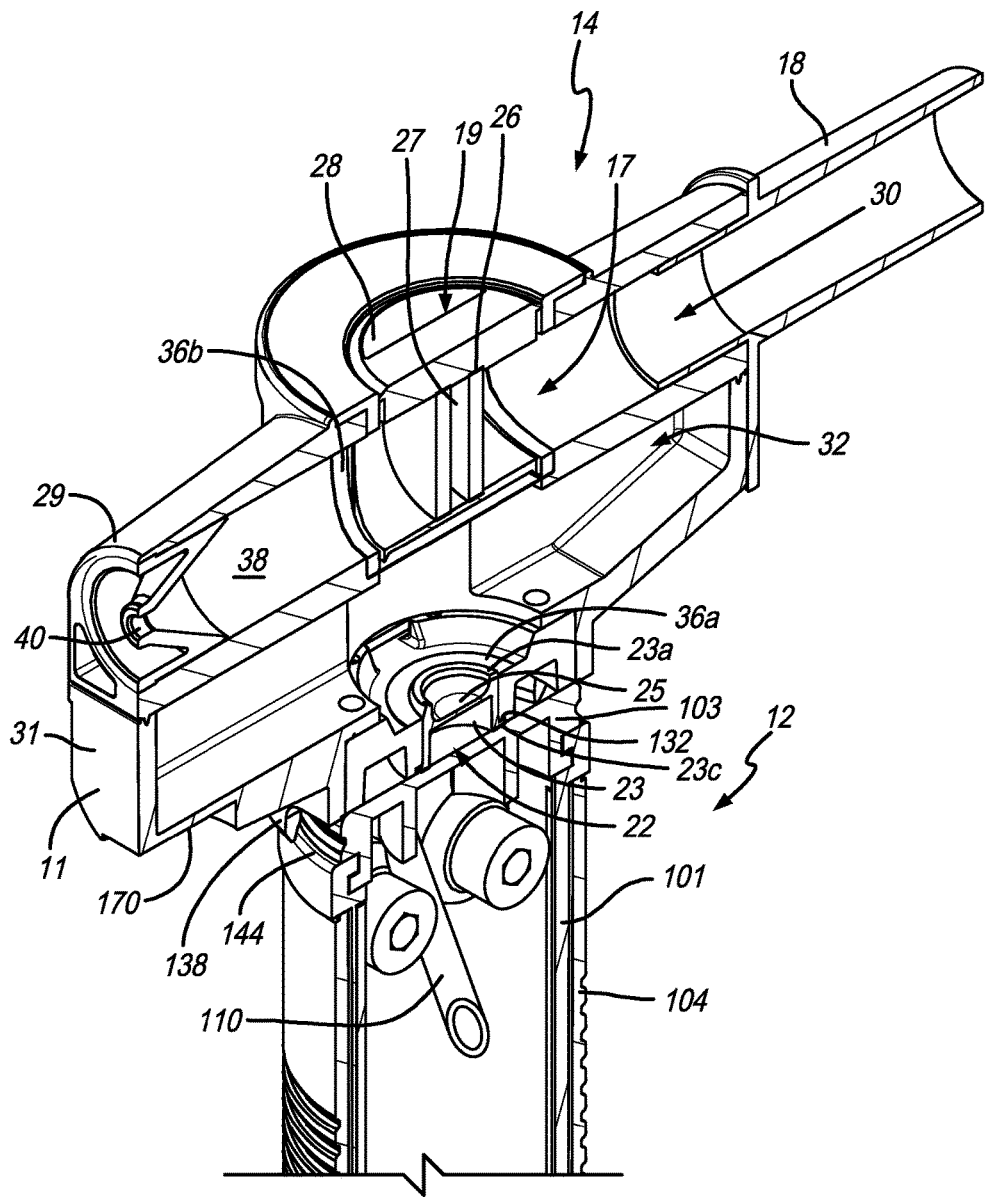
FIG. 5B is a cross-sectional perspective view of the analysis cartridge after being connected to the handle assembly.

FIG. 4 is an exploded view of the handle assembly 12 and the components thereof. In a preferred embodiment, the handle assembly 12 includes an elongated main body portion 101 with first and second halves 102 that define a handle interior 99 (see FIG. 5A), top and bottom end caps 103 and 105, a grip 104, a cable 106 that connects to the analysis device 16 (electric and/or data) via plug 107 and a pressure transducer 50 and associated components (circuit board 108, pressure tube 110, etc.). The handle assembly 12 also preferably includes a magnet 111 that interacts with a magnet 150a in handle storage pocket 66 and tube 150 described below. A pressure protrusion 49 extends outwardly from the upper surface 52 of the top end cap 103 (see FIG. 5A). A pressure opening 113 is defined in the top of the pressure protrusion 49. In a preferred embodiment, the pressure protrusion includes an O-ring 115 therearound that seals the pressure protrusion 49 when it is coupled to the analysis cartridge 14. Preferably, the pressure protrusion 49 is received in a pressure recess 139 (see FIG. 7) defined in the lower portion 31 of the analysis cartridge. As shown in FIGS. 5 and 5A, in a preferred embodiment, the pressure path within the handle assembly 12 extends from the pressure opening 113, through an extension 117 on the bottom surface of the top end cap 103 (which is received in the pressure tube 110), through the pressure tube 110 and to the pressure transducer 50 (an end of which is received in the pressure tube 110). Generally, the pressure path is defined between the pressure opening 113 and the pressure transducer 50. The cable 106 is connected to the circuit board 108. Therefore, the pressure reading of the pressure transducer 50 can be communicated to main circuit board 74 of the analysis device 16.

FIGS. 5A-6B show the analysis cartridge 14 being attached to the handle assembly 12. In a preferred embodiment, the analysis cartridge 14 includes a collar 138 extending downwardly from the main body portion 11. The collar 138 includes at least one and preferably a plurality of attachment recesses 140 defined therein. One of the recesses 140 mates with an alignment or attachment protrusion 142 on the top end cap 103 of the handle assembly 12 (in another embodiment there can be more attachment protrusions 142). The collar 138 is also received on a seat 144 that is a part of the top end cap 103. An annular protrusion extends outwardly from cap 103 that mates with an undercut slot on the collar 138 and that creates a snap fit. A friction fit is also within the scope of the present invention. The attachment recesses 140 allow the collar to expand when secured on the top of the handle assembly 12.

The pressure recess 139 for receiving the pressure protrusion 49 on the top of the handle assembly 12 is defined within the collar 138. The complementary attachment recess 140 and attachment protrusion 142 align the analysis cartridge 14 and handle assembly 12 during the attachment process so that the pressure protrusion 49 is received in the pressure recess 139. The seat 144 can include a rubber material or the like for providing a friction fit with the collar 138. Any method of attaching the analysis cartridge 14 to the handle assembly 12 is within the scope of the present invention. For example, analysis cartridge 14 to the handle assembly 12 can be connected by a threaded fit, snap fit, friction fit or the like.

As shown in FIG. 5A, in the first position, the ampule member 22 extends downwardly from the lower portion 31 of the analysis cartridge 14. Therefore, when the analysis cartridge 14 is connected to the handle assembly 12, the lower surface 23b of the ampule member 22 contacts the upper surface 52 of the handle assembly 12, thereby pushing the ampule member 22 upwardly, thus breaking the first breakable barrier 36a, and moving the ampule member from the first position to the second position. This facilitates transferring the PD derivative 24 into the fluid chamber 32 and the elution solution 34. It will be appreciated that the PD derivative 24 is kept separated from the elution solution 34 until the analysis cartridge 14 is connected to the handle assembly 12. The elution solution 34 and PD derivative 24 mix to form a phenylene diamine solution ("PD solution") 35 (further mixing of the elution solution 34 and PD derivative 24 analysis device 16 is described below).

With references to FIGS. 2-7, another feature included in the analysis cartridge 14 is the breath pressure measurement capability. This enables a patient blowing into the analysis cartridge to know via the screen 60 on the analysis device 16 whether the blown pressure is within a predetermined range. Generally, a pressure path is defined between a pressure measurement hole 42 in the upper portion 29 of the analysis cartridge 14 (that is in communication with the breath chamber 30) and the pressure transducer 50 in the handle assembly 12. As shown in FIG. 3A, the pressure path extends from the pressure measurement hole 42 to a pressure channel 44 that extends partially around the filter assembly 19, and to a pressure tunnel 46 that extends downwardly through the main body portion 11. It will be appreciated that FIG. 3A shows a top ring cover 47 omitted from the analysis cartridge 14. The top ring cover 47 (or other wall or barrier) encloses the pressure channel 44 to maintain the pressure.

Figure 7:
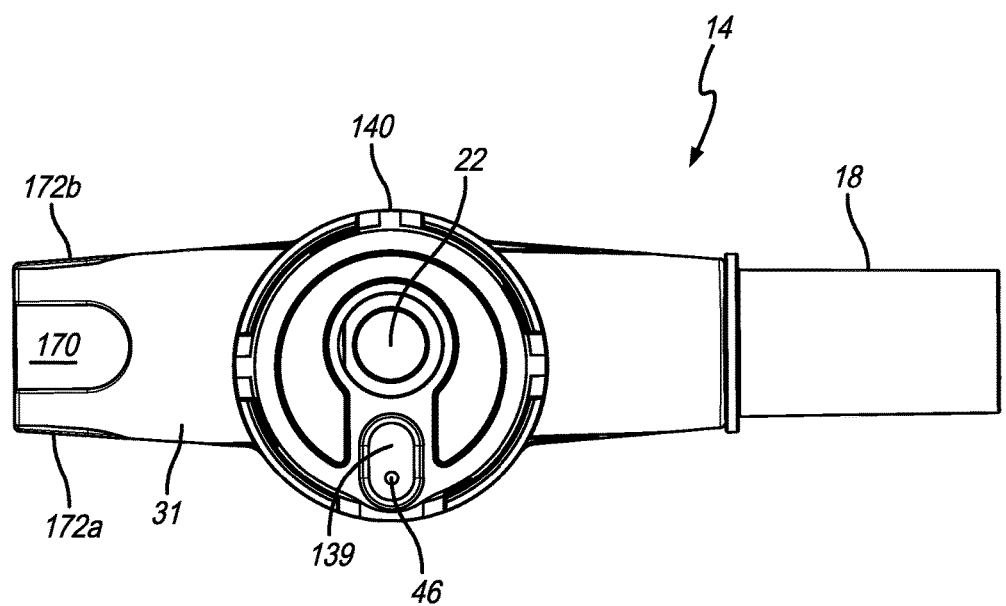
FIG. 7 is a bottom plan view of the analysis cartridge.
Figure 8:
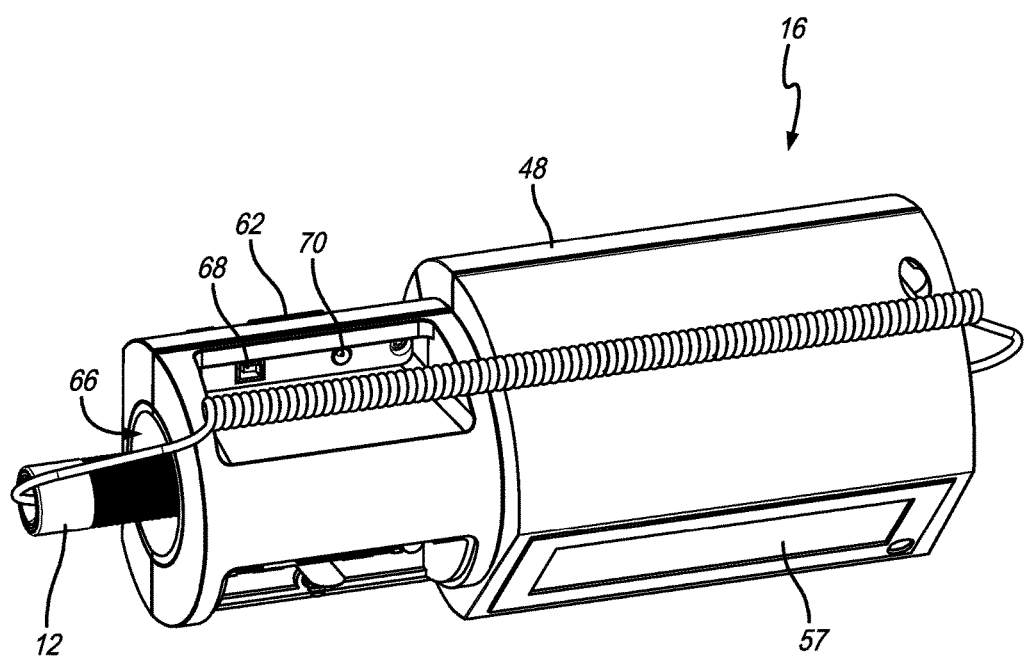
FIG. 8 is a perspective view of the back of the analysis device.

FIG. 7 shows the bottom of the analysis cartridge 14 and the end of the pressure tunnel 46 that communicates with the pressure recess 139. When the pressure protrusion 49 is received in the pressure recess 139, the pressure tunnel 46 is communicated with the pressure opening 113. Therefore, the complete pressure path extends from the pressure measurement hole 42, through the pressure channel, through the pressure tunnel, through the pressure opening, through the hollow extension 117, through the pressure tube 110 and to the pressure transducer 50.

When a patient blows through the breath chamber 30 (and the frit plates 26), a pressure measurement is taken. In a preferred embodiment, this requires a pressure differential flow calculation. As breath is being blown through the breath chamber, depending on how hard the person is blowing, there is a pressure differential that is created in the distal space 38 of the breath chamber 30 in between the rear frit plate 26 and the breath exit hole 40. The pressure measurement hole 42 is defined in the wall within the distal space 38 and is essentially a tap for measuring ambient and distal pressure differential. The pressure of the breath in distal space 38 via pressure measurement hole 42 pressurizes the existing air within the pressure channel (pressure path). The pressure path extends through the pressure measurement hole 42 into the channel 44 and is channeled over and then down through pressure tunnel 46 and to the handle assembly 12. The pressure that is inside the distal space 38 of the breath chamber 30 is being measured by pressure transducer 50 and based on the pressure measurement the flow rate through the breath chamber 30 can be calculated. The electronics of the pressure transducer 50 are located in the handle assembly 12 (i.e., on the circuit board 108).

In use, once the analysis cartridge 14, is placed on the handle assembly 12, a user blows through the mouthpiece 18 and the breath chamber 30 so that a predetermined volume of air or breath (e.g., 3 liters) is exhaled through the breath chamber 30. Therefore, CCM are filtered out of a predetermined or known volume of breath and are collected on the substrate 28. After the CCM have been collected, the user removes the analysis cartridge 14 from the handle assembly 12, removes the mouthpiece 18 and places the analysis cartridge 14 in the analysis device 16, as described below. The analysis cartridge 14 and handle assembly 12 in combination (shown in FIG. 6B) are referred to herein as the breath capture assembly 13.

Figure 6A:
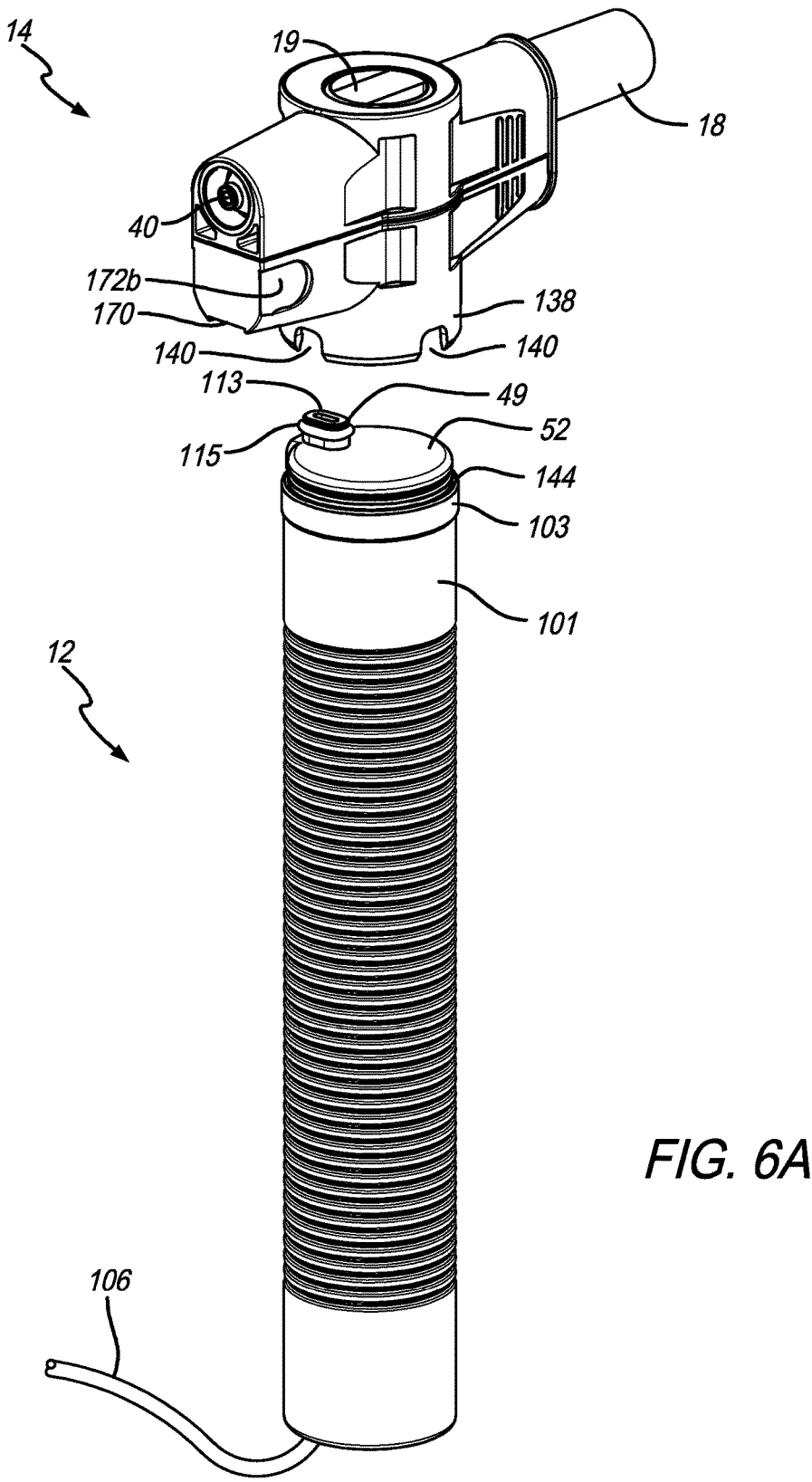
FIG. 6A is a perspective view of the analysis cartridge prior to being connected to the handle assembly.
Figure 6B:
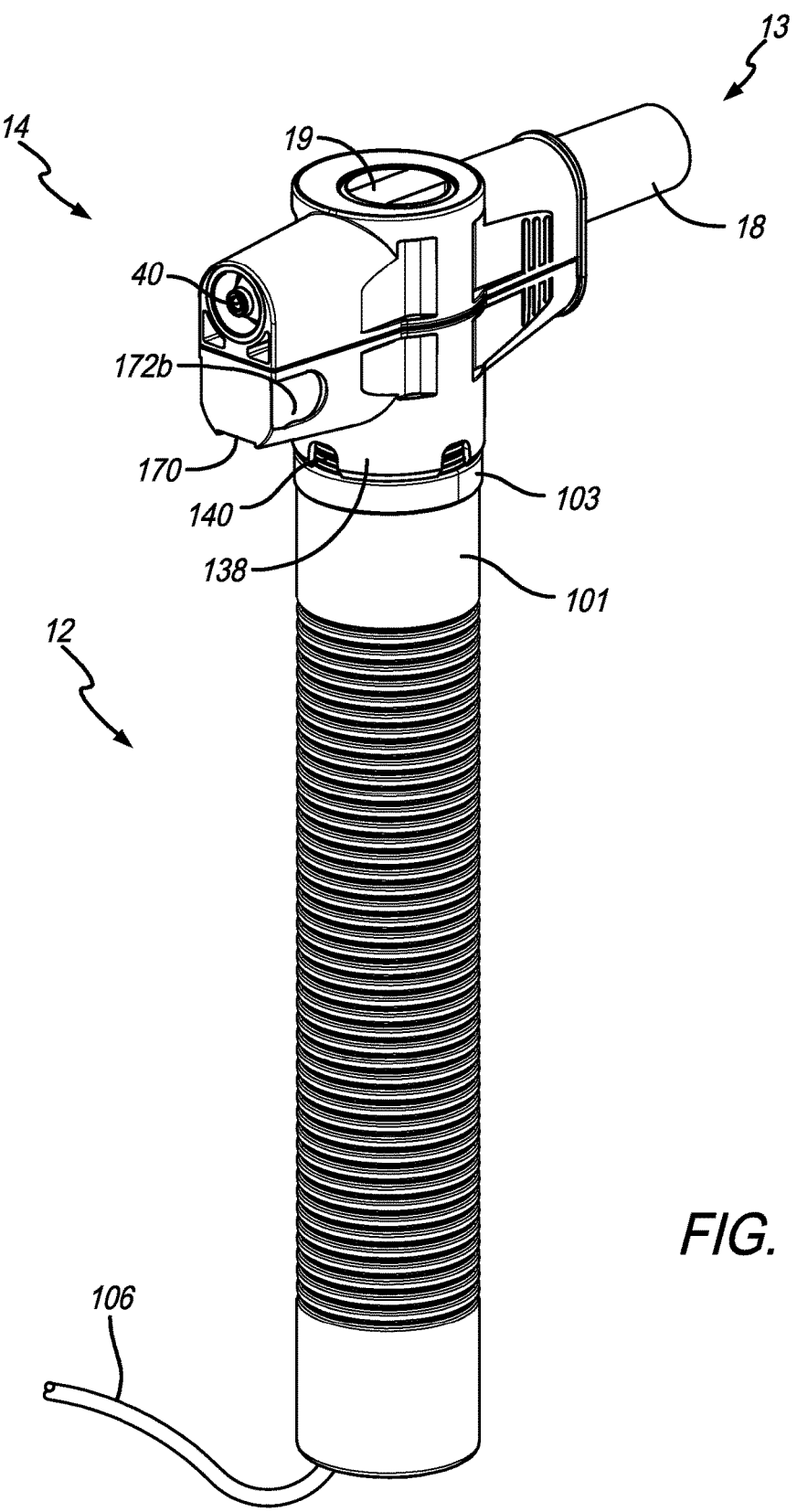
FIG. 6B is a perspective view of the analysis cartridge connected to the handle assembly.

As shown in FIGS. 6A-7, the analysis cartridge includes a bottom window and two side windows. The bottom window is referred to herein as the fluorescence window 170 and the side windows are referred to herein as the light entry window 172a and the light exit window 172b. The fluorescence window 170, light entry window 172a and light exit window 172b are used in conjunction with an optical system 77 (also referred to herein as a fluorescence detection assembly or fluorometer) in the analysis device 16 described below. In a preferred embodiment, the windows 170 and 172a and 172b are a clear plastic and are the same material as the remainder of the main body portion 11. However, the windows can be a different material. Preferably, the windows 170 and 172a and 172b are optically polished and are oriented such that outer surface is orthogonal to the appropriate components of the optical system 77 (described below). In a preferred embodiment, the remainder of the main body portion 11 is not optically clear and includes a draft so that the windows 170 and 172a and 172b are isolated (i.e., the sides or bottom of the cartridge are angled or not parallel to the outer surface of the windows). Preferably, the light entry and light exit windows 172a and 172b are parallel to one another and the fluorescence window 170 is perpendicular to the light entry and light exit windows 172a and 172b.

In a preferred embodiment, the analysis cartridge 14 is made of plastic (e.g., polycarbonate, PMMA, etc.) and the various pieces are ultrasonically bonded to one another. However, this is not a limitation and the analysis cartridge can be made of any desirable material and bonded as desired.

Figure 9:
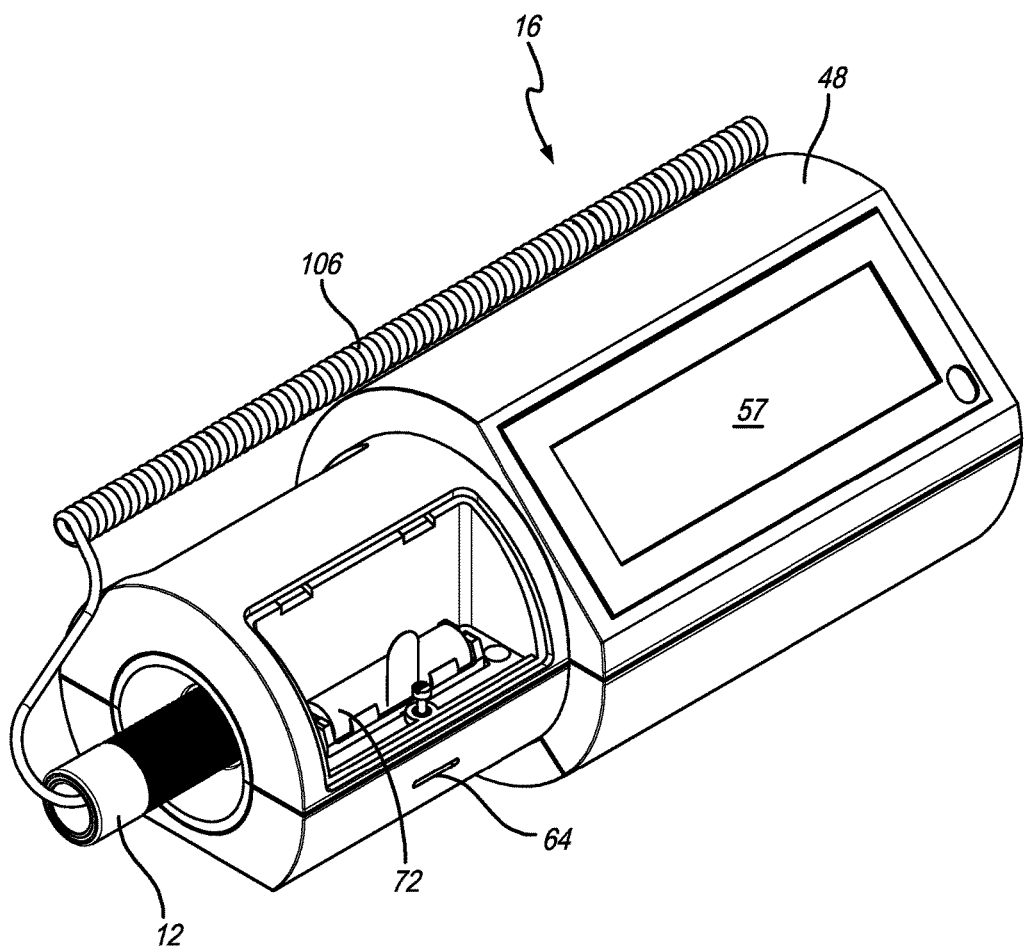
FIG. 9 is a perspective view of the back of the analysis device with the battery cover removed.

FIGS. 1 and 8-23 show the analysis device 16. As shown in FIGS. 1 and 8-11, generally, the analysis device 16 includes a case 48 (comprised of two halves 48a and 48b), a door 54 that is slidable between open and closed positions, a shroud 56, analysis pocket 58 defined in the shroud 56 (where the analysis cartridge is received), a bottom 57, a main circuit board 74, a rotation assembly 76 and a display 60 (which is preferably touch screen). It will be appreciated that the full analysis pocket 58 includes the tapering funnel portion 58a and the well 173 described below. The analysis device 16 also includes an on/off button 62, a speaker 64, a handle storage pocket 66, a USB port 68 and a DC input power port 70 (see FIG. 8). The analysis device 16 also includes a battery 72, as shown in FIG. 9 and a battery door 156 shown in FIG. 11. The battery is preferably rechargeable, however this is not a limitation.

Figure 10:
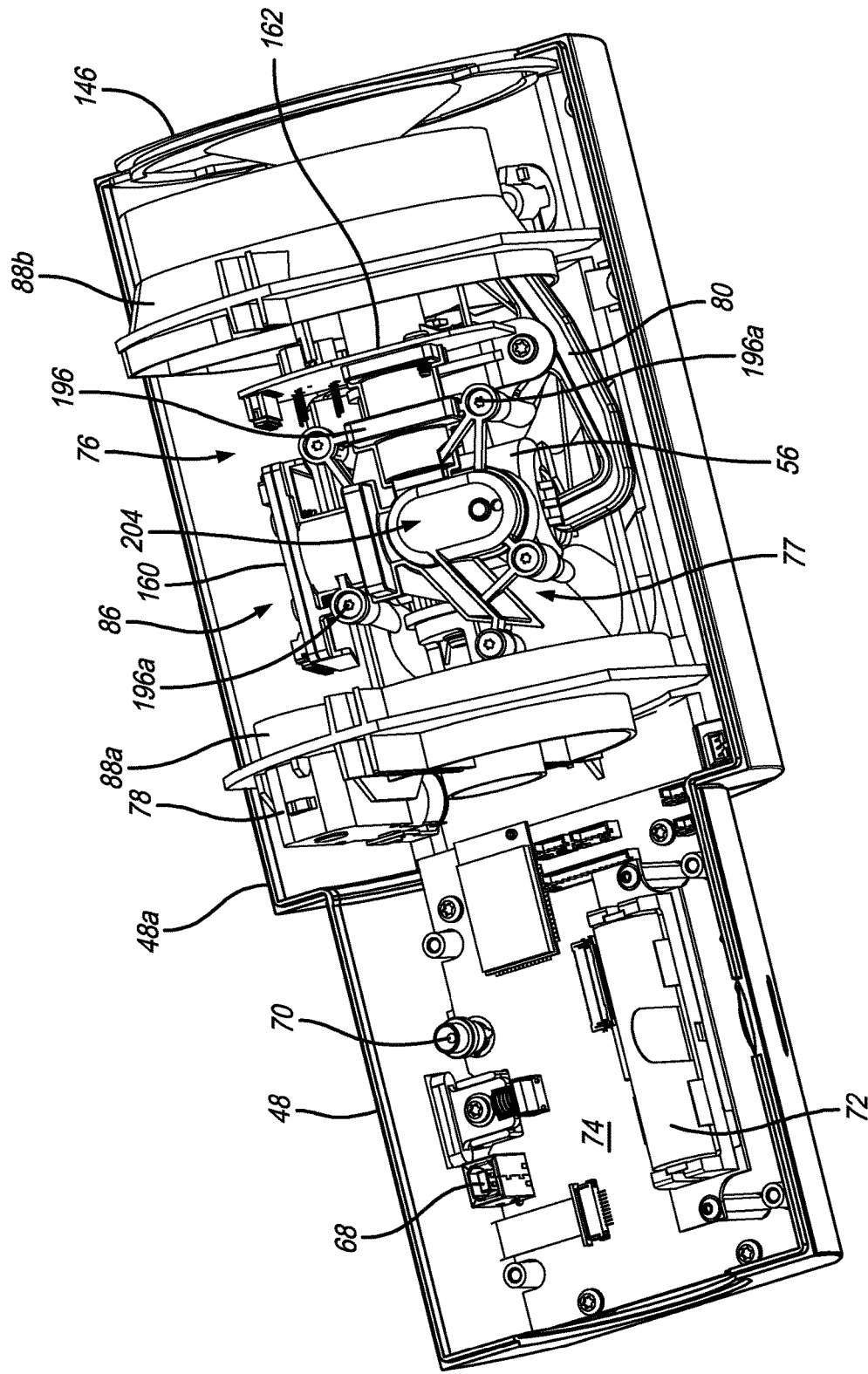
FIG. 10 is a perspective view of the analysis device with half of the case removed.

Shroud 56 is the interface between the analysis cartridge 14 and the analysis device 16. In use, after a breath sample is taken using the analysis cartridge 14, the user places the analysis cartridge in the analysis pocket 58 (through pocket opening 58b) and closes the door 54. FIG. 10 shows the analysis device 16 with the bottom half of the case 48b removed. As shown, the analysis device 16 includes the main circuit board 74 and the rotation assembly 76 for mixing the elution solution 34 and aldehydes, as described below. The rotation assembly 76 also includes the optical system 77. The main circuit board 74 (mother board) is the controller and includes (or is in electrical communication with), but is not limited to, the USB port 68, DC input power port 70, cable(s) for communicating with a motor 78 and the optical system 77 (and optics boards 160 and 162 described below), a cable for communicating with the handle assembly 12 (via plugs 107 and 148, cable 106 and circuit board 108), the display 60, on/of switch 62, battery 72, and optical sensors for sensing if the door 54 is open or closed.

Figure 11:
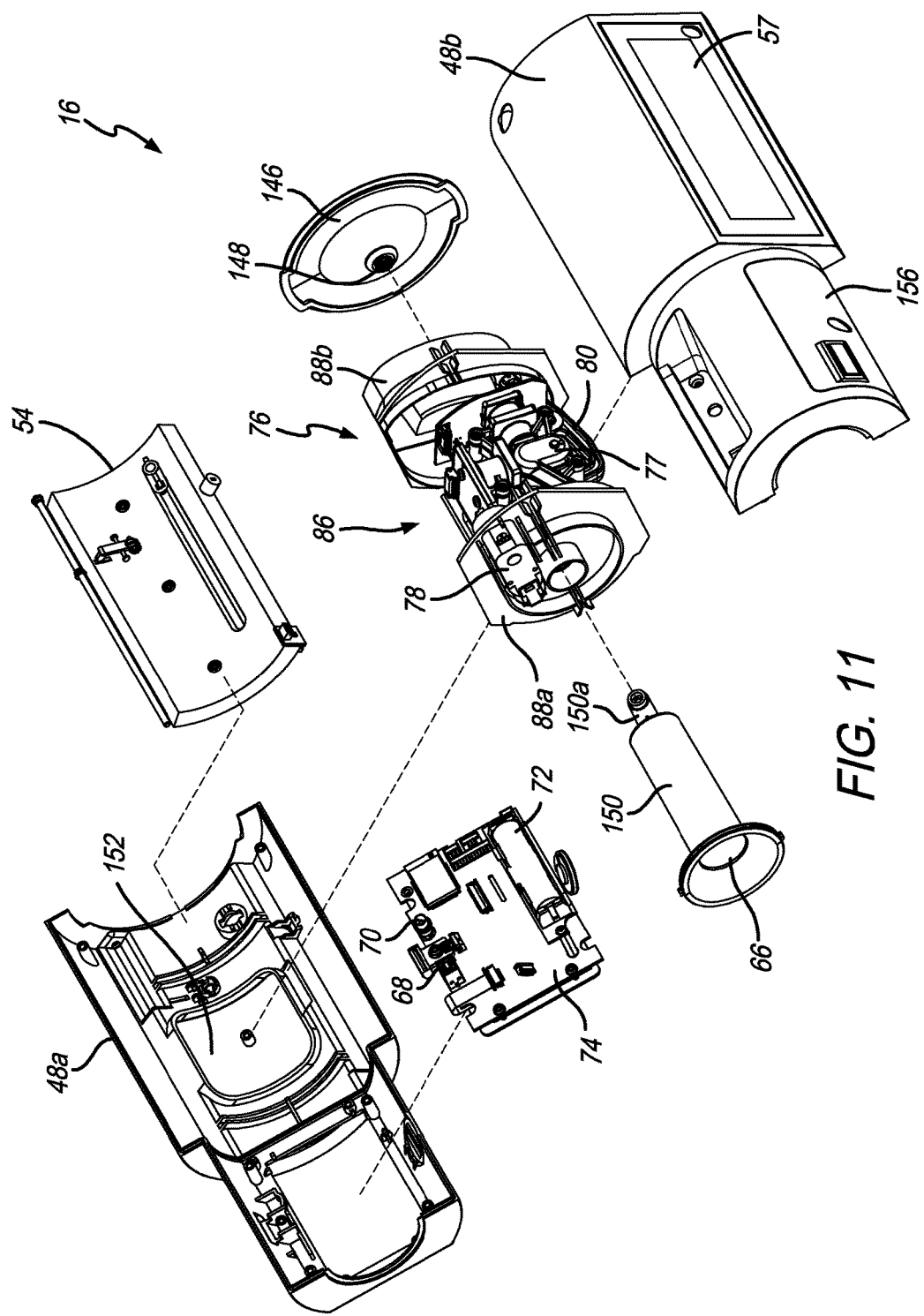
FIG. 11 is an exploded perspective view of the analysis device.

FIG. 11 shows the analysis device 16 exploded and illustrates the first and second halves of the case 48a and 48b, the slideable door 54, the main circuit board 74 and the rotation assembly 76. As shown, the analysis device 16 also includes an end cap 146 having a plug 148 therein for connection of the cable 106, and a tube 150 that defines the handle storage pocket 66. As discussed above, the handle storage pocket 66 and tube 150 include a magnet 150a that interacts with magnet 111 in the handle assembly 12. The interaction of the two magnets helps hold the handle assembly 12 in the handle storage pocket 66. In a preferred embodiment, the first half of the case 48a includes an opening 152 that aligns with the shroud 56 to define the analysis pocket 58. Opening/cover 154 in the case 48 houses the display 60. In a preferred embodiment, the second half of the case 48b includes the bottom 57, battery door 156 and openings for the USB port 68 and DC input power port 70, which are part of the main circuit board 74.

Figure 12:
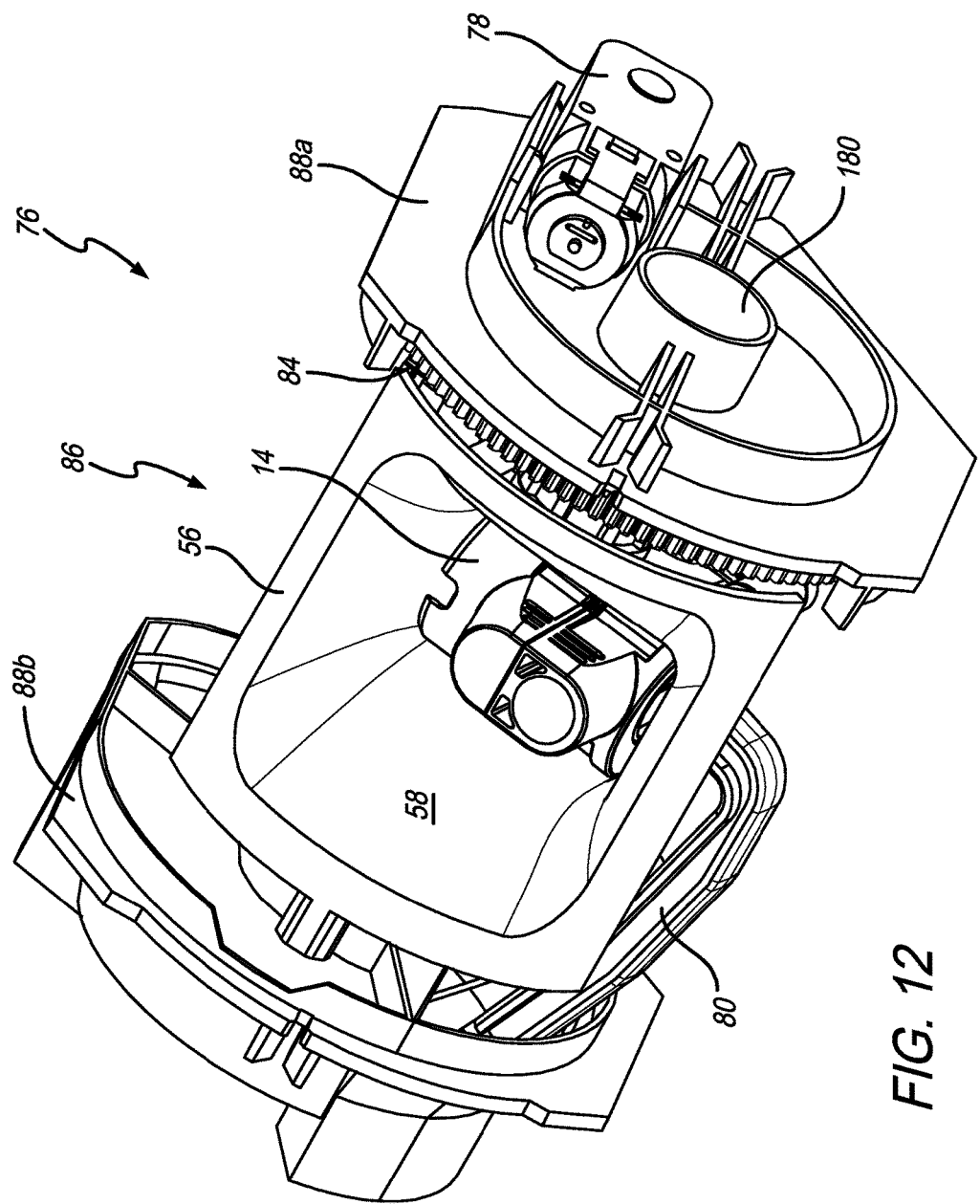
FIG. 12 is a top perspective view of the rotation assembly with the analysis cartridge in the pocket.
Figure 13:
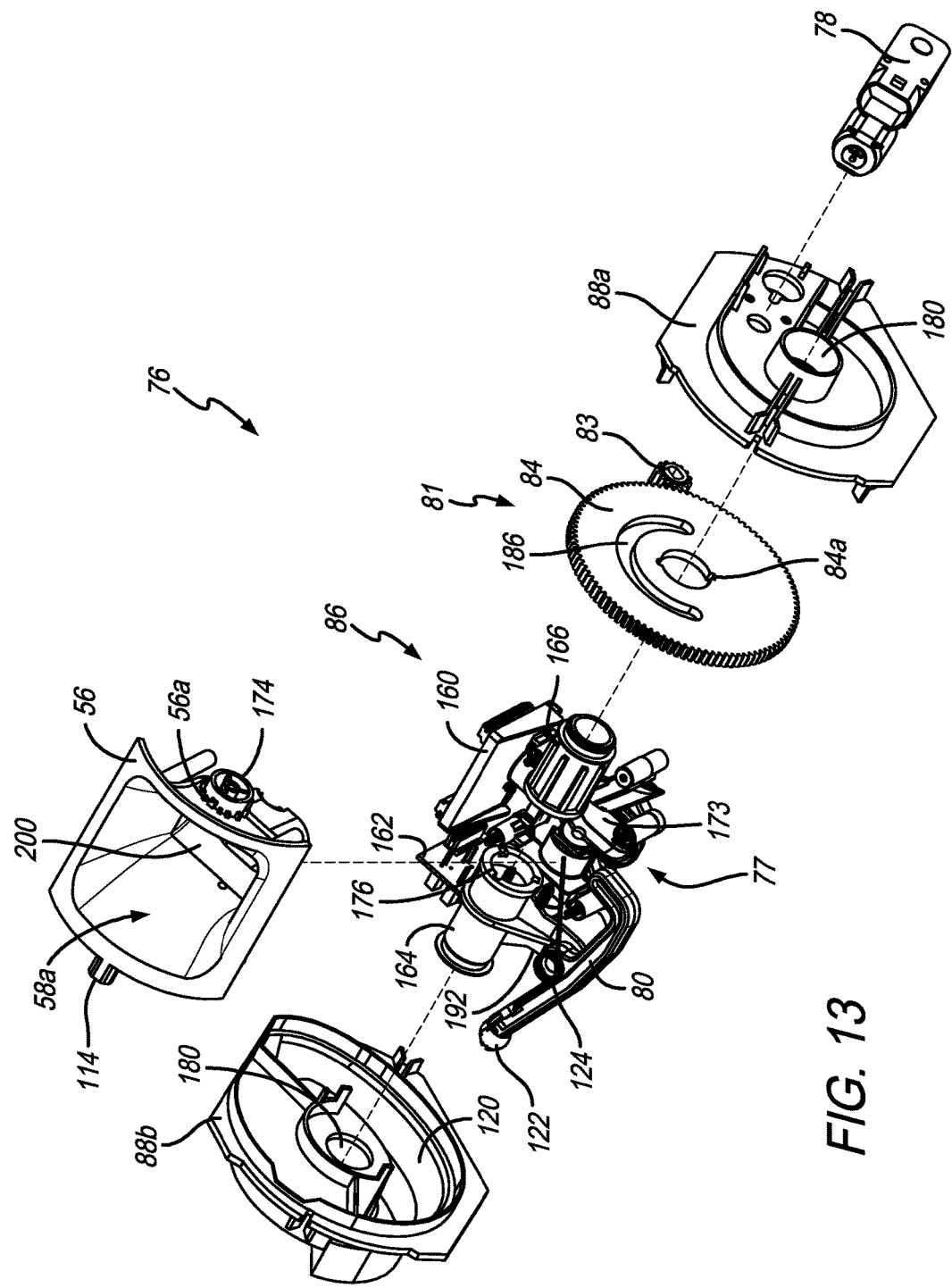
FIG. 13 is an exploded perspective view of the rotation assembly.
Figure 14:
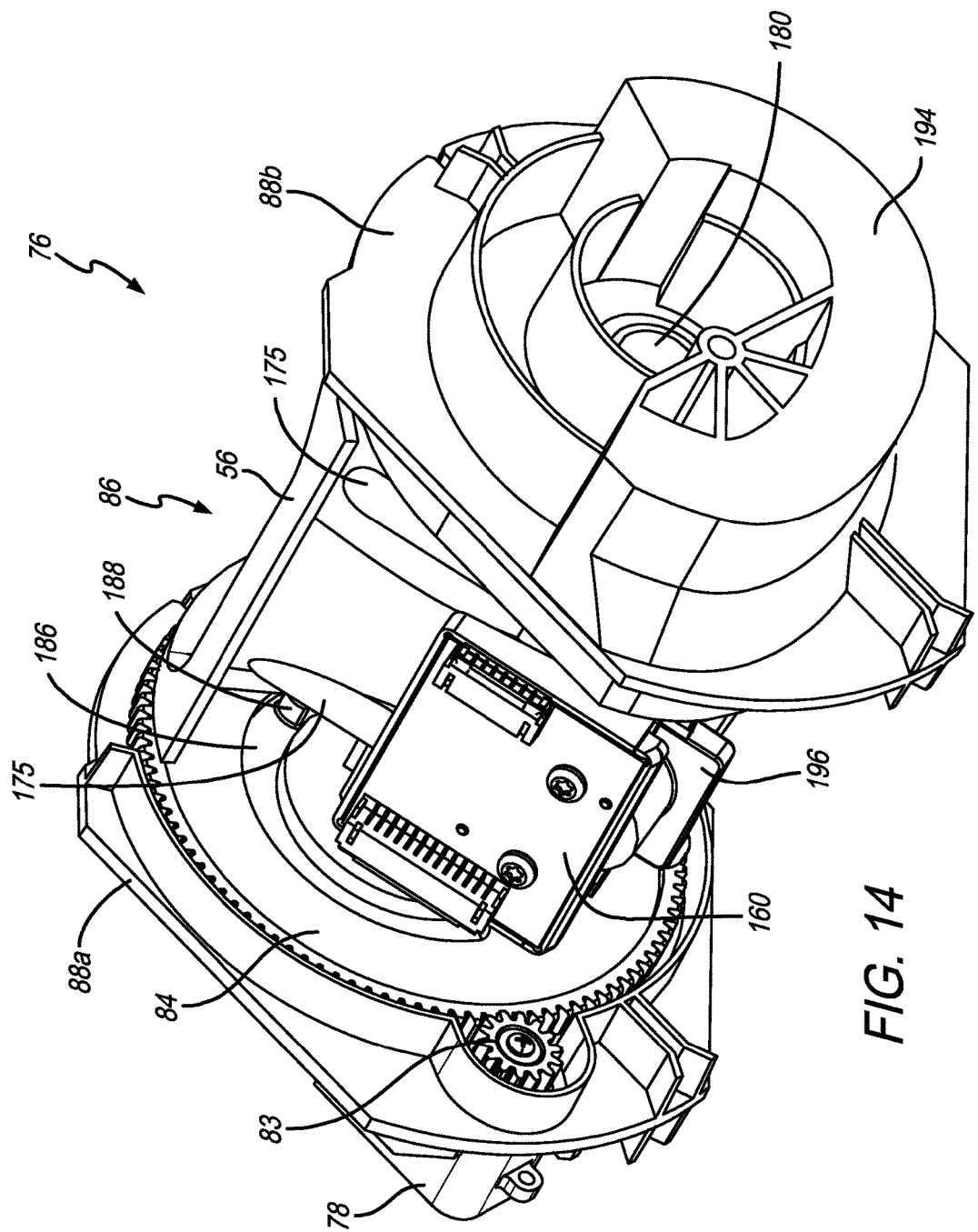
FIG. 14 is another perspective view of bottom perspective view of the rotation assembly.
Figure 15:
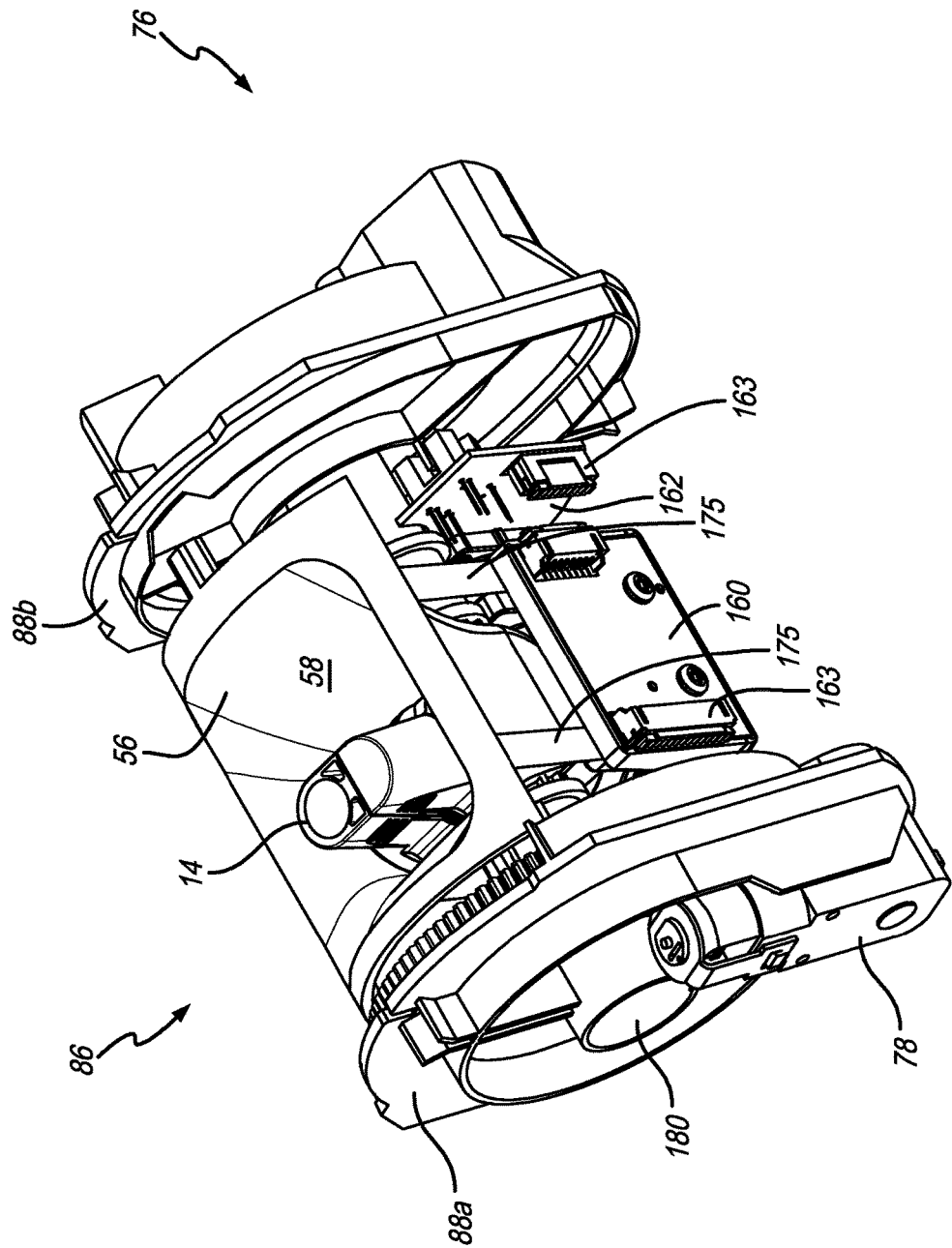
FIG. 15 is a perspective view of the rotation assembly with the analysis cartridge in the pocket.

FIGS. 12-20 show the rotation assembly 76 with most other components omitted. As shown in FIGS. 12-13, the rotation assembly 76 generally includes a rotatable portion 86, first and second fixed members 88a and 88b, motor 78, a gear train 81 (that preferably includes a pinion gear 83 that drives a large gear 84), the shroud 56, and the optical system 77. Motor 78 includes a drive shaft (not shown) that drives pinion gear 83, which meshes with and rotates large gear 84. Motor 78 is preferably controlled by main circuit board 74. It will be appreciated that the center portion (the rotatable portion 86) pivots, and the fixed members 88a and 88b stay stationary within the case 48. Large gear 84 preferably includes an arcuate slot 186 therein that receives a guide protrusion 188 on fixed member 88a. The ends of the arcuate slot 186 provide stops (by interacting with guide protrusion 188) so that the rotatable portion 86 can only rotate a certain degree in each direction.

Figure 16:
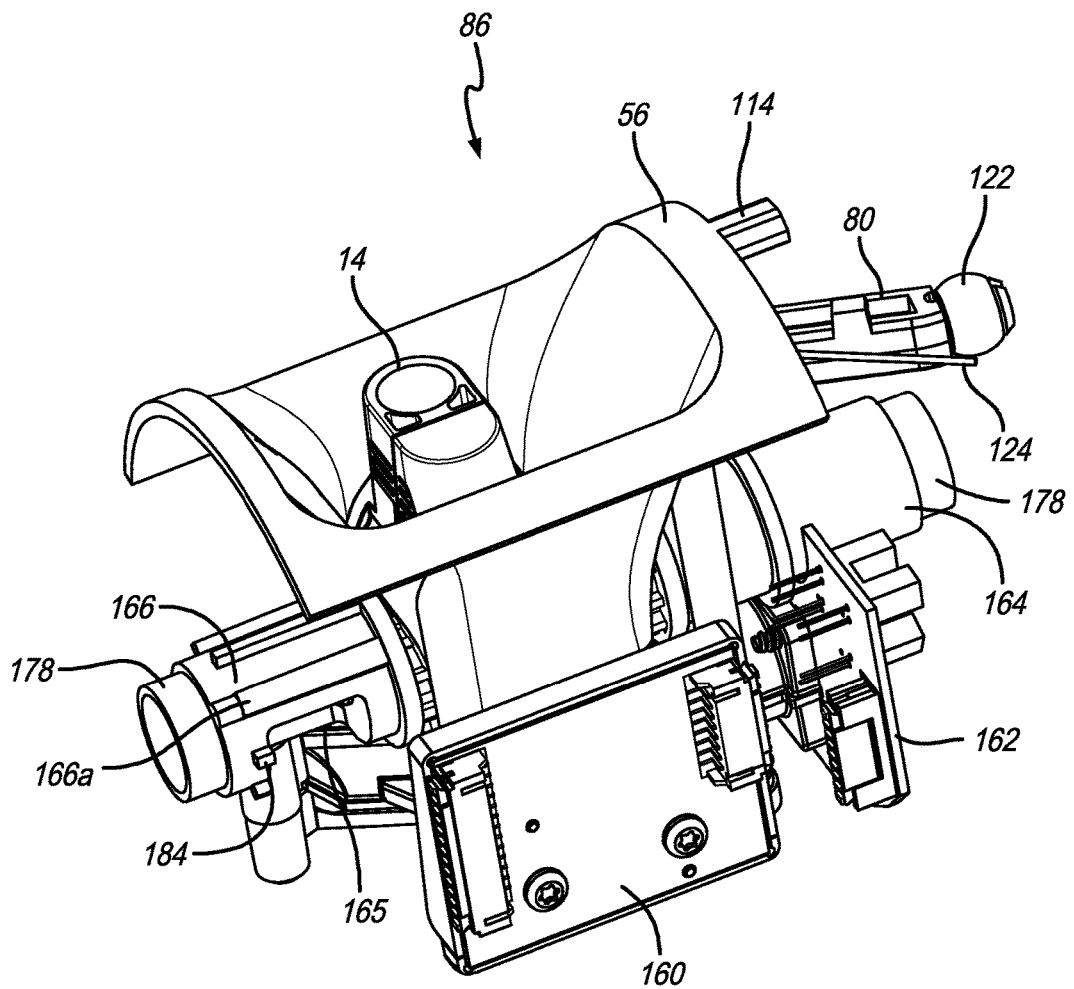
FIG. 16 is a perspective view of the rotatable portion with the analysis cartridge in the pocket.
Figure 17A:
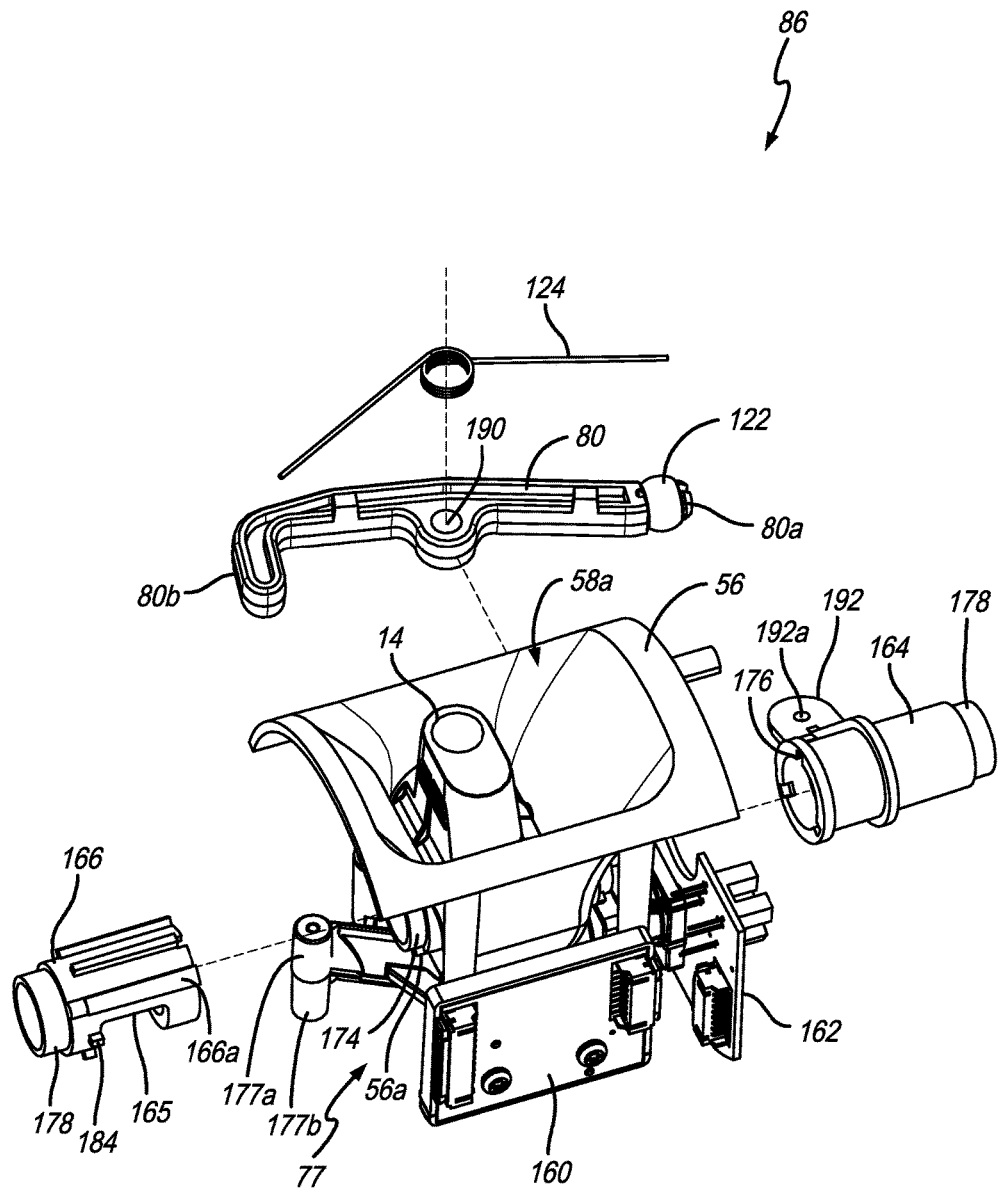
FIG. 17A is an exploded perspective view of the rotatable portion with the analysis cartridge in the pocket.
Figure 17B:
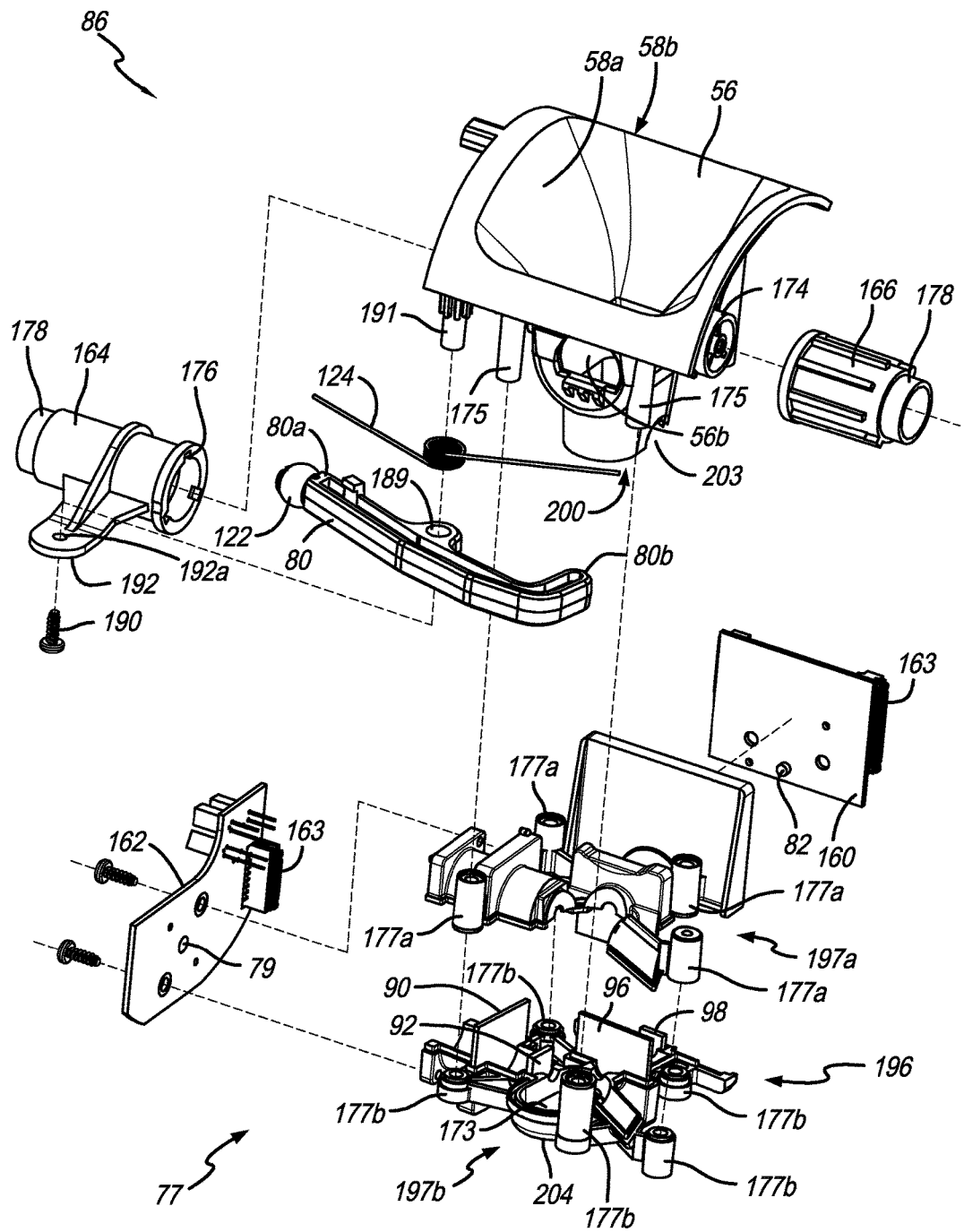
FIG. 17B is another exploded perspective view of the rotatable portion.

FIGS. 16-17B show the rotatable portion 86 alone. The rotatable portion 86 includes first and second axle members 164 and 166 that connect to the shroud via a key and keyway relationship. This is not a limitation. In another embodiment, the first and second axle members 164 and 166 can be glued or bonded to the shroud or can be unitary with the shroud. As shown in FIG. 13, in a preferred embodiment, the shroud 56 includes axially aligned cylindrical protrusions 174 with a key 56a on opposite sides thereof. The protrusions 174 receive first and second axle members 164 and 166 that include complementary keyways 176 defined therein. First and second axle members 164 and 166 are preferably keyed so that they only fit on the shroud 56 in one orientation.

The first and second axle members 164 and 166 have bearings 178 thereon that cooperate with central openings 180 in the fixed members 88a and 88b and allow the rotatable portion 86 to rotate. The rotatable portion 86 is connected to the large gear 84 via at least one key 166a that meshes with at least one keyway 84a in the center opening of the large gear 84. The second axle member 166 also includes a stop 184 for the large gear 84 and a cable passing recess 165 that allows a cable (not shown) coming from the main circuit board 74 and extending to the optical system 77 to pass therethrough. Therefore, the motor 78 drives the pinion gear 83, which drives the large gear 84, which meshes with and drives the second axle member 166, which drives the shroud 56 (which holds the analysis cartridge 14 in the analysis pocket 58) and all other components attached thereto, such as the optical system 77 and an arm 80 (discussed below).

In a preferred embodiment, the analysis device 16 includes a door lock assembly where the door 54 is locked by the motion of the rotation assembly 76. Preferably, the door lock assembly includes a door detection sensor that senses whether the door is open or closed. The shroud 56 includes a cam feature 114 (see FIG. 16) thereon that interacts with a pivotal tab member on the case. The cam feature 114 is positioned so that when the rotation assembly 76 goes to the load position the tab is disengage, thus allowing the door to slide open. In all the other orientations of the rotation assembly 76, the tab is up and that locks the door and prevents it from sliding open.

As will be described below, the rotatable portion 86 rotates with the analysis cartridge 14 therein to mix the PD solution 35 therein and to allow the optical system 77 to perform its analysis. In addition, the rotatable portion 86 includes a cam and lever system to translate the rotational motion to pivotal motion, so that the arm 80 pushes the filter assembly 19 from the breath chamber 30 into the fluid chamber 32. FIGS. 17A-19C show the cam and lever system and how the rotation assembly 76 moves the arm 80. The arm 80 is pivotal on post 191 that defines a pivot axis and includes a first end 80a with a ball bearing 122 thereon that rides on a cam surface 120 and a second end that moves in and out of an arm opening 56b in the side of shroud 56. In a preferred embodiment, the arm 80 is pivotal on post 191 and is secured to a tab 192 that extends from the first axle member 164, as shown in FIG. 17B. Preferably, the arm 80 includes an opening 189 that receives post 191, which extends downwardly from the shroud 56 (see FIG. 17B). Spring 124 is formed so that the coil section forms an opening that receives post 191. A fastener 190 extends through the opening 192a in tab 192 and into the end of post 191. The first end 80a of the arm 80 with the ball bearing 122 extends into a cam channel 194 defined in second fixed member 88b (see FIG. 18).

Figure 18:
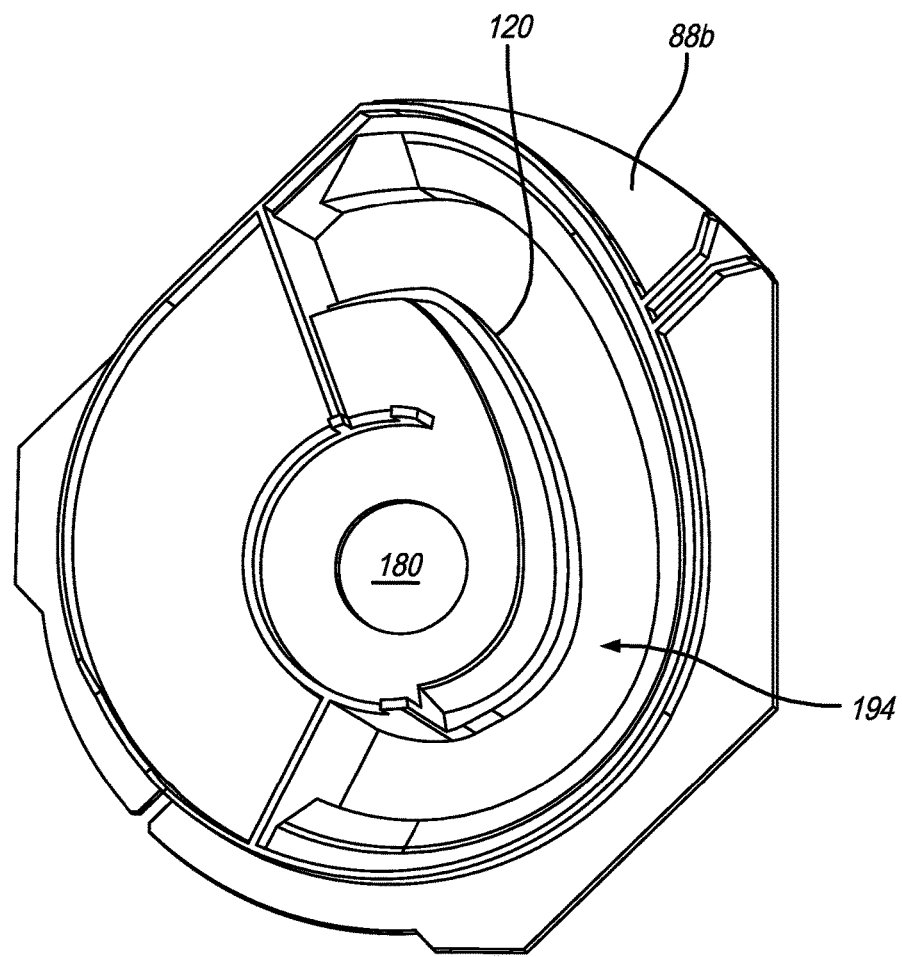
FIG. 18 is a perspective view of the second fixed member that includes the cam track.
Figure 19A:
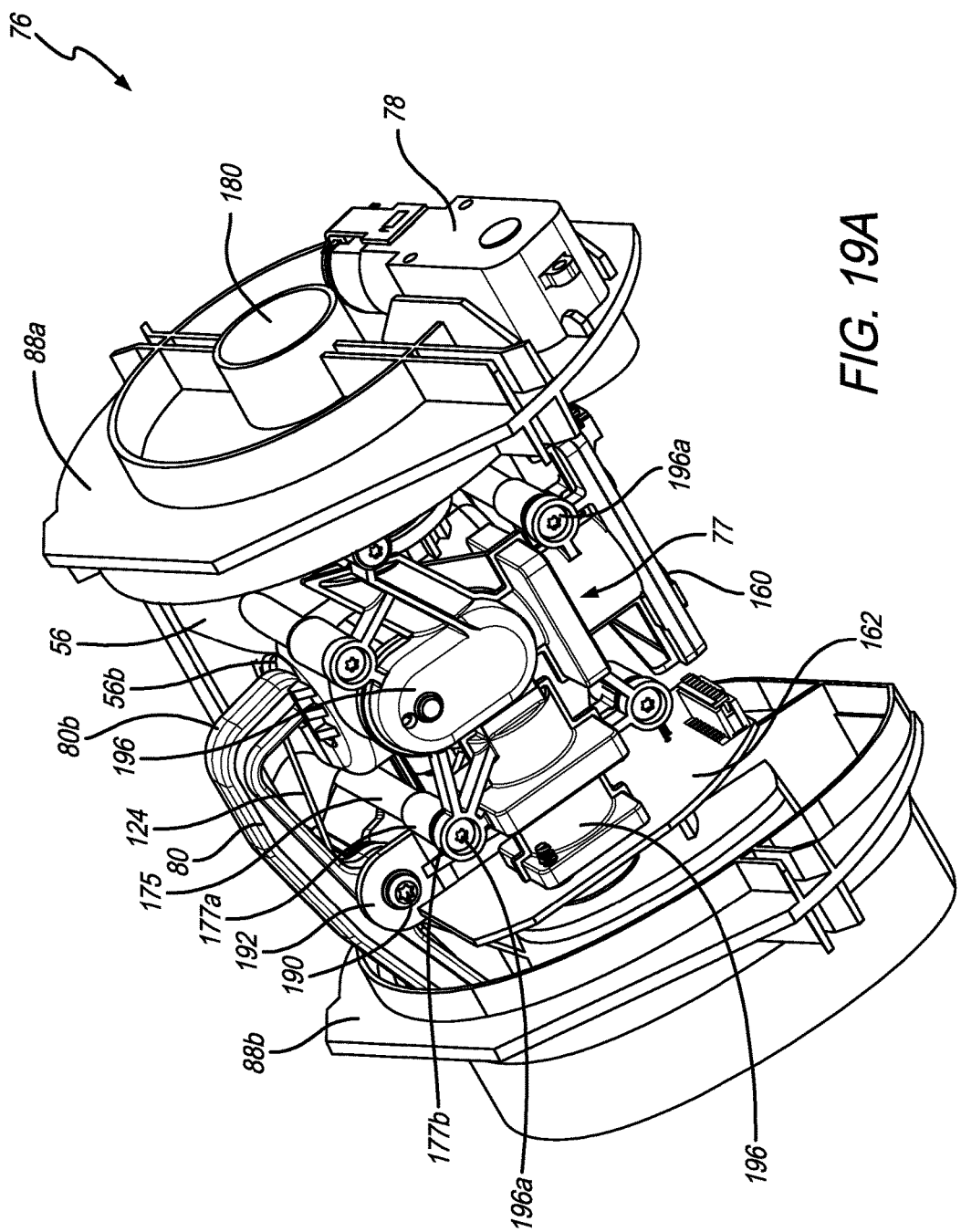
FIG. 19A is a perspective view of the rotation assembly with the arm in the stowed position.
Figure 19B:
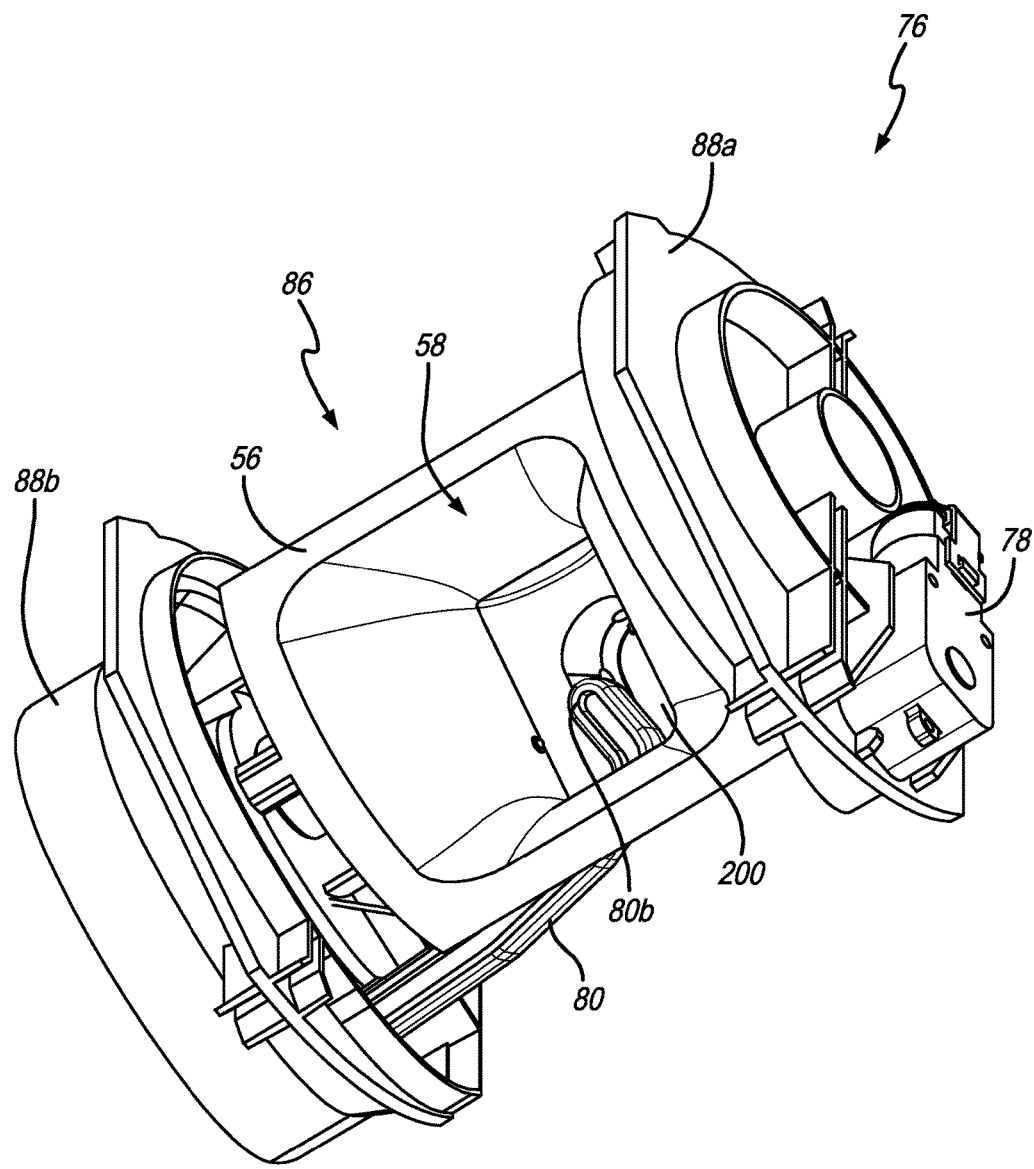
FIG. 19B is a perspective view of the rotation assembly with the arm in the deployed position.
Figure 20:
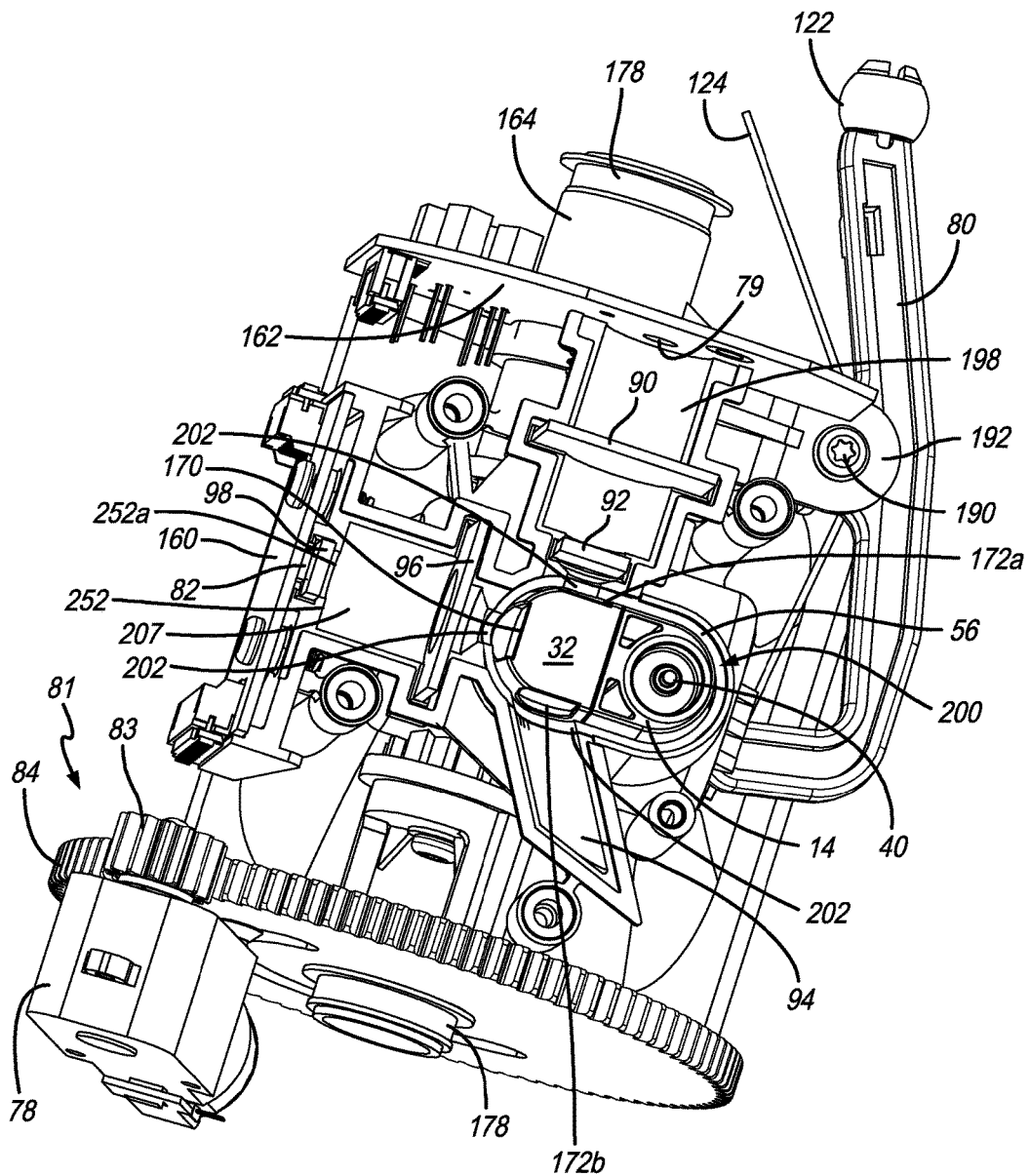
FIG. 20 is a perspective view of a portion of the rotatable assembly with the second halve of the housing removed to show the components of the optical system.

The arm 80 is movable between a stowed position (FIG. 19A) and a deployed position (FIG. 19B). Spring 124 biases the arm to the stowed position. As shown in FIG. 18, the cam surface 120 is curved and includes an increasing radius along the path that the ball bearing 122 travels. As the rotatable portion 86 (and arm 80) rotates, the ball bearing 122 rides on cam surface 120. The increasing radius of the cam surface 120 causes the arm 80 to pivot about pivot axis and therefore push the second or working end 80b of the arm 80 into arm opening 56b in the shroud 56. Compare FIG. 19A where the arm is not pivoted inwardly to FIG. 19B where it is pivoted inwardly. Due to the positioning of the analysis cartridge 14 within shroud 56, the second end 80b of the arm 80 pushes the filter assembly 19 from the breath chamber 30 to the fluid chamber 32. The cam surface 120, ball bearing 122, pivotal (and spring biased via spring 124) arm 80 work together to convert rotational motion into pivotal motion.

FIGS. 17B-17D and 20 show the optical system 77. The optical system 77 includes a housing 196 comprised of first and second halves 197a and 197b (the second half 197b is omitted in FIG. 20). The housing 196 is preferably secured to the shroud 56 by threaded fasteners 196a (see FIG. 10). In a preferred embodiment, the shroud 56 includes four fastener receiver members 175 that receive the elongated threaded fasteners 196a that extend through complementary first and second receiver tubes 177a and 177b on the first and second housing halves 197a. The fastener receiver members 175 can be internally threaded or can be made so that the threads are created in the plastic as the threaded fastener 196a is screwed therein. As shown in FIG. 17B, an extra set of first and second receiver tubes 177a and 177b are included that do not correspond to a fastener receiver member 175 on the shroud 56. The threaded fasteners 196a therefore secure the two halves of the housing together and secure the housing 196 to the shroud 56.

Figure 17C:
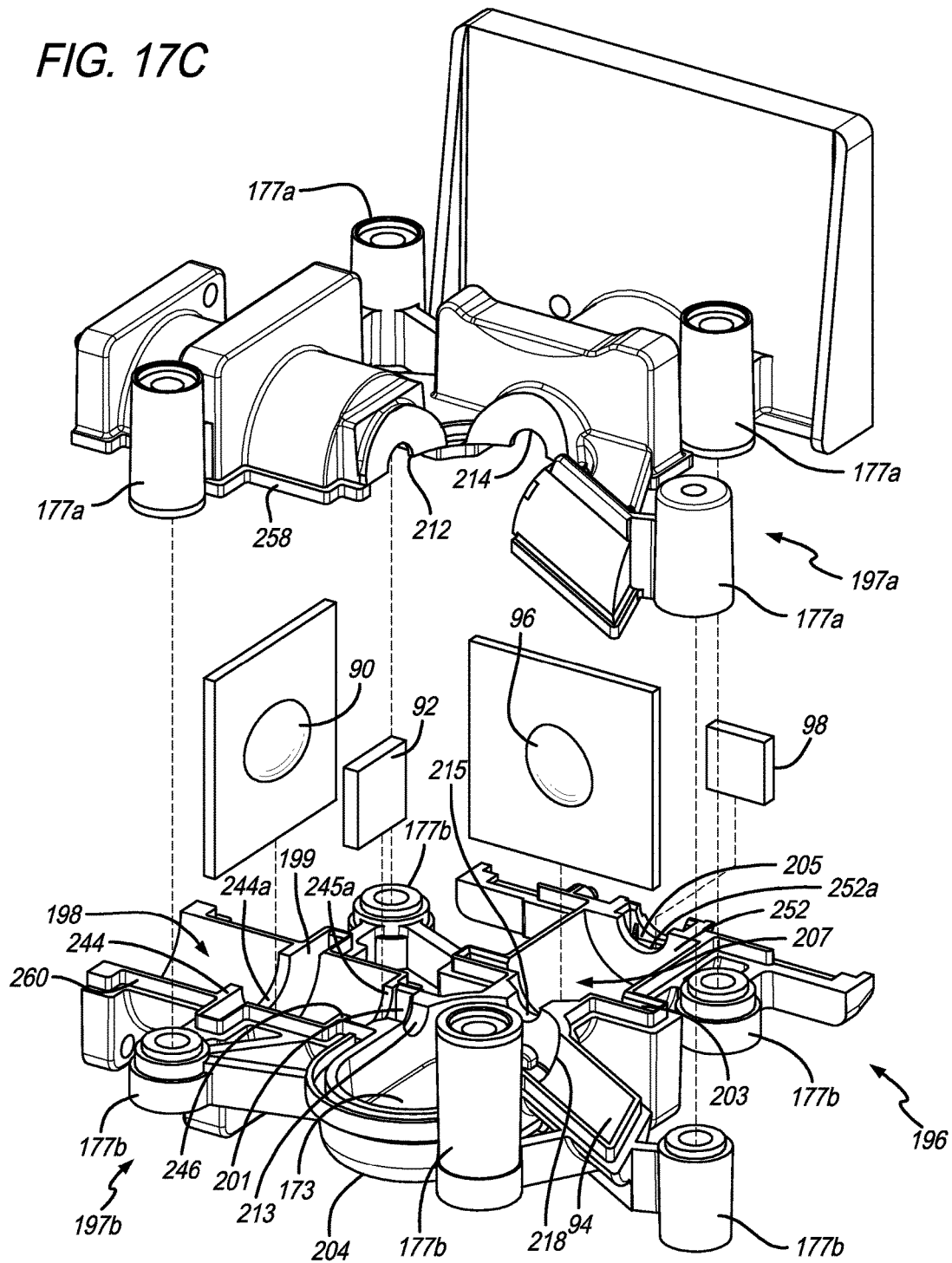
FIG. 17C is an exploded perspective view of the optical system.

Shroud 56 includes an analysis opening 200 in the bottom thereof through which the back of the analysis cartridge 14 extends when it is in the analysis pocket 58. The analysis opening 200 is aligned with a well 173 in the second half 197b of the housing 196 that receives the back of the analysis cartridge 14 therein. The housing 196 includes an analysis cartridge receiving portion 204, as shown in FIG. 17C that defines the well 173. The housing 196 is formed such that the first and second housing halves 197a and 197b cooperate to define an light chamber 198, a fluorescence chamber 207, a light trap 94, and the well 173. The shroud 56 includes three recesses 203 on the bottom surface thereof that cooperate with recesses on the analysis cartridge receiving portion 204 to define a light entry aperture 216, a fluorescence aperture 217 and a light trap opening 218.

The optical system 77 also includes a first optics circuit board or microcontroller 162 that includes an LED 79 and a second optics circuit board 160 that includes a receiver or detector 82 (e.g., a photo diode). Both optics circuit boards include sockets or connectors 163 for connecting cables (not shown) for communication and control from the main circuit board 74. The optical system 77 also includes at least a first lens 90 and at least a first filter 92 positioned in the light chamber 198, and at least a second lens 96 and at least a second filter 98 that are positioned in the fluorescence chamber 207. The housing 196 is formed such that the first and second housing halves 197a and 197b cooperate to define a first lens pocket 199, a first filter pocket 201, a second lens pocket 203 and a second filter pocket 205.

As shown in FIGS. 17C-17E and 20, the top housing half 197a includes first and second recesses 212 and 214 defined therein that cooperate with first and second recesses 213 and 215 in the top surface of the analysis cartridge receiving portion 204 to at least partially form the light entry aperture 216 and the fluorescence aperture 217. The top and bottom housing halves 197a and 197b also cooperate to at least partially form the light trap opening 218. When the analysis cartridge 14 is positioned in the well 173, the light entry window 172a is aligned with the light entry aperture 216, the fluorescence window 170 is aligned with the fluorescence aperture 217, and the light exit window 172b is aligned with the light trap opening 218.

In use, the LED 79 shines light along a light path (LP) through the first lens 90, through a first filter 92, through light entry aperture 216, through light entry window 172a in analysis cartridge 14 (where it causes the CCM in the fluorescing solution 206 to fluoresce within the sensing chamber 32b), through light exit window 172b, through light trap opening 218 and into light trap 94. The light trap 94 is configured with angled walls so that the light that enters therein bounces around and cannot escape back through the entry opening and be reflected in any way toward the detector 82. The light reflected from the fluoresced CCM exits the analysis cartridge 14 along a fluorescence path (FP) through fluorescence window 170 at an approximately 90 degree angle from the light entering the analysis cartridge 14. The fluorescence path travels through fluorescence aperture 217, through the second lens 96 and the second filter 98 and to the detector 82. This is generally an emitter detector set-up. In a preferred embodiment, the detector 82 is at about ninety degrees to the emitter 79. Other angles are within the scope of the invention.

Figure 17D:
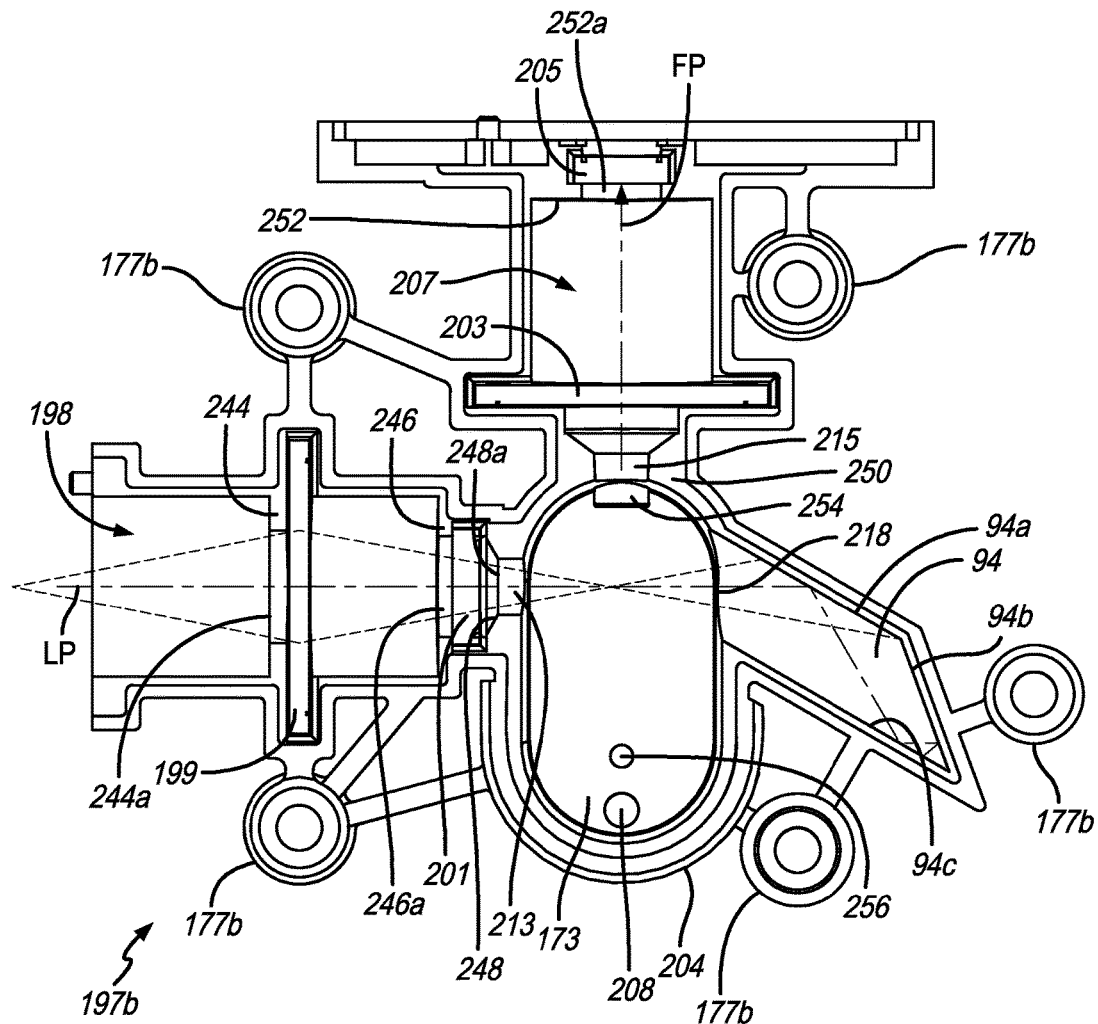
FIG. 17D is a plan view of the bottom half of the optical system housing.
Figure 17E:
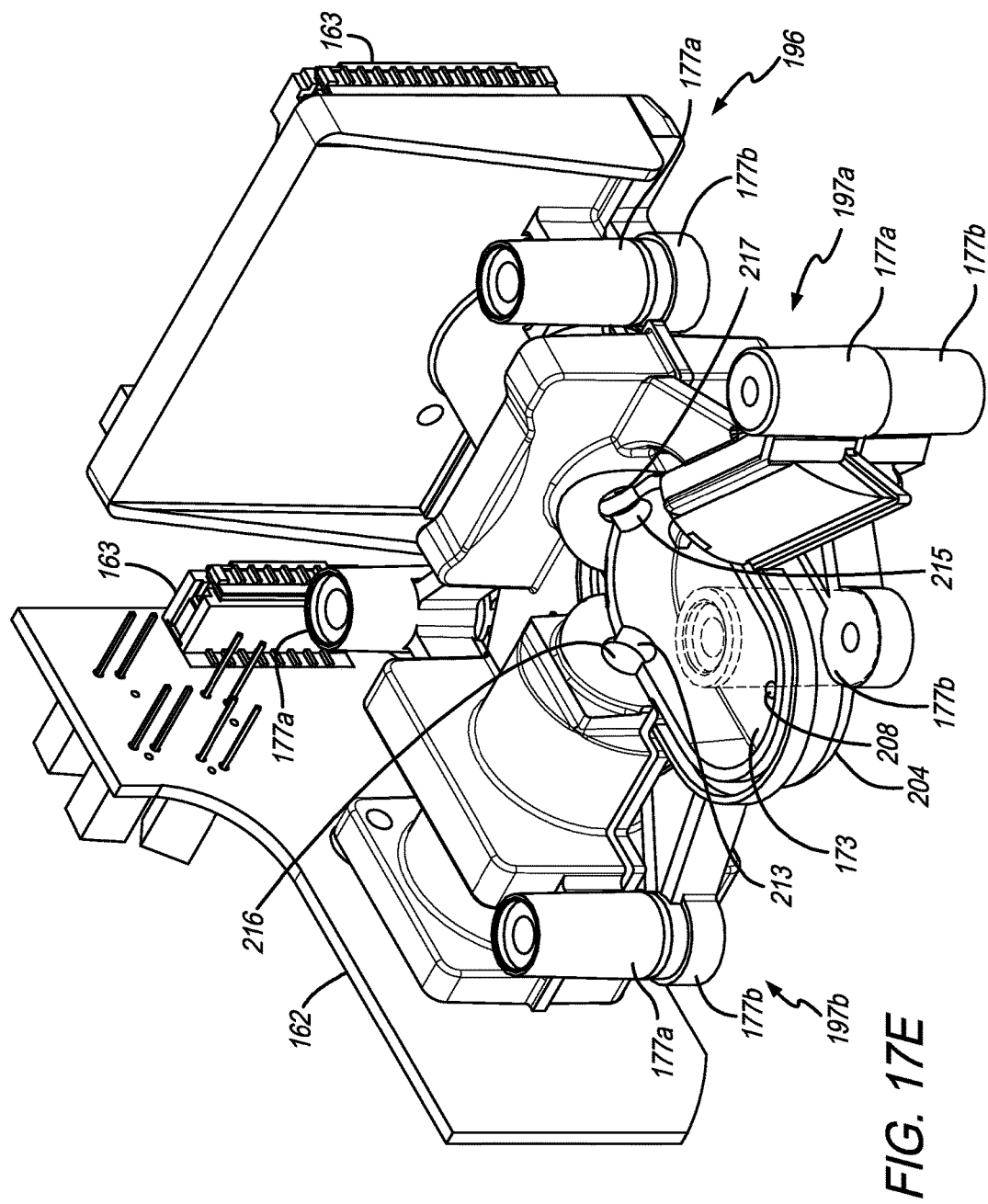
FIG. 17E is a perspective view of the optical system.

In a preferred embodiment, the light emitted from the LED 79 and directed along the light path LP is as collimated as possible. Preferably, the light chamber 198 is designed to eliminate as much light as possible that is not collimated. To accomplish this, the light chamber 198 includes at least the first lens 90, and a series of baffles and apertures (described below) positioned in the light path LP. FIG. 17D shows the light path LP as being directed parallel to the axis of the light chamber 198. However, some light emitted from the LED 79 may not extend parallel to the axis. See, for example, the dashed lines in FIG. 17D. In a preferred embodiment the first lens 90 is a Fresnel lens. However, this is not a limitation on the present invention. In an exemplary embodiment, the first lens 90 is a Fresnel lens with a focal length of about 10 mm, overall dimensions of 25.4 mm×25.4 mm×22 mm with a lens diameter of 12.7 mm (the second lens can have the same properties). However, none of these dimensions are limiting. The first lens 90 is positioned and includes specifications such that it preferably focuses the light from the LED 79 inside of the sensing chamber 32b, within the well 173. In an exemplary embodiment, the collimated beam of light is approximately 4 mm in diameter in the center of the sensing chamber 32b.

As shown in FIG. 17C-17D, in a preferred embodiment, the light chamber 198 includes a first light baffle 244 positioned therein that includes a first light baffle aperture 244a defined therein. The first light baffle 244 is positioned along a light path LP before the first lens 90. The light chamber 198 also includes a second light baffle 246 positioned therein that includes a second light baffle aperture 246a defined therein. The second light baffle 244 is positioned along the light path LP between the first lens 90 and the first filter 92. Preferably, a third light baffle 248 that includes a third light baffle aperture 248a is positioned in the light path LP after the first filter 92. Preferably, the first and second light baffles are orthogonal to the direction of the light path LP and the third light baffle is not orthogonal to the direction of the light path LP. It will be appreciated that the baffles and apertures are formed by the first housing half 197a cooperating with the second housing half 197b. FIG. 17D only shows the second housing half 197b.

After the light passes through the analysis cartridge passes through the light trap opening 218 and into the light trap 94. In a preferred embodiment, the walls of the light trap are black, which will absorb the majority of light that enters. FIG. 17D shows a plan view of the light trap 94. In a preferred embodiment, the light trap 94 includes curved walls that help disperse the light as it bounces off. However, as shown in FIG. 17D, with respect to the light path LP, the walls form angles that are designed to absorb most light because they are black, but also to reflect any light that is reflected toward another wall so that virtually no light escapes back through the light trap opening 218. The light trap 94 preferably includes a first wall 94a that receives the light after it enters the light trap. The first wall is preferably angled between about 25° and about 45° with respect to the light path LP. In an exemplary embodiment it is angled at 35° from the light path LP. The light trap 94 also preferably includes a second wall 94b that is angled from the light path LP. Preferably, it is not at a right angle with the light path LP. In an exemplary embodiment, as light enters the light trap 94, every time it bounces off a different wall approximately 80% is absorbed and 20% is reflected. After bouncing off of a few walls with the 80% to 20% absorption to reflection ratio, the remaining light will be negligible.

The fluorescence path FP also includes baffles and apertures therein together with the second lens 96 and second filter 98. As shown in FIG. 17D, in a preferred embodiment, the fluorescence path FP includes therealong a first fluorescence baffle 250 and related aperture, which is the fluorescence aperture 217 that is formed by the second recess 215 in the top surface of the analysis cartridge receiving portion 204 and the defined therein, the second lens 96, a second fluorescence baffle 252, which includes a second fluorescence baffle aperture 252a defined therein and second filter 98. Preferably, the second lens 96 has the same specifications as the first lens 90. However, this is not a limitation and the two lenses can be different. In another embodiment either or both of the light path and the fluorescence path can include more than one lens therein.

It will be appreciated that the light emitted from the LED is not completely collimated. Therefore, the light baffles and apertures are provided to block some of the light that is reflected off of the inside of the light chamber 198 and other extraneous light. The apertures in the first, second and third light baffles 244, 246 and 248 have smaller diameters than the light chamber 198, thereby causing the light baffles to block or eliminate non-collimated light some light and help create a more collimated beam traveling along the light path LP through the light chamber 198.

In a preferred embodiment, the diameters of the first, second and third light baffles get smaller as they are encountered along the light path. In an exemplary embodiment, the light chamber 198 has an inner diameter of about 16 mm, the first light baffle aperture has an inner diameter of about 10 mm, the second light baffle aperture has an inner diameter of about 9 mm, and the first light baffle aperture has an inner diameter of about 5 mm. As for the fluorescence chamber 207, in an exemplary embodiment, the first fluorescence baffle aperture has an inner diameter of about 5 mm and the second fluorescence baffle aperture has an inner diameter of about 7 mm.

As shown in FIG. 17D, in a preferred embodiment, the first lens pocket 199, first filter pocket 201, second lens pocket 203 and second filter pocket 205 each include crush ridges therein that help maintain the lens or filter therein in a stable position and prevent it from vibrating. However, the crush ridges can be omitted. Also, the well 173 can include an alignment member 254 therein and a drain 256 for draining any fluid in the well 173.

The first filter 92 is provided to filter unwanted wavelengths of light from the beam of light emitted from the LED 79. Any filter is within the scope of the present invention. In a preferred embodiment, the first filter allows transmission of light in a first range. For example, the first filter can include a transmission region of 300 nm to 540 nm T<0.0001%, OD>6, a transition region 540 nm to 550 nm, 0%<T<100%, and a blocking region that blocks light between 550 nm and 800 nm, T>90%. However, this is only exemplary and any filter is within the scope of the present invention. In a preferred embodiment, the second filter allows transmission of light within a second range. For example, the second filter can include a blocking region that blocks light between 300 nm and 555 nm, T<0.0001%, OD>6, a transition region 555 nm to 565 nm, 0%<T<100%, and a transmission region of 565 nm to 800 nm T>90%. However, this is only exemplary and any filter is within the scope of the present invention. The second filter 98 is designed to block all LED light that somehow made it into the fluorescence chamber 207 and to only allow the fluorescent light through at a predetermined wavelength (e.g., a long pass filter).

In a preferred embodiment, to further separate the fluorescence signals, lock-in amplification is used. A lock-in amplifier is used to help eliminate signals that have an origin in background light (e.g., lights from the room, circuit boards inside the device, backlighting from the screen, and any other white source that could potentially reach the detector 82). In an exemplary embodiment of using this technique, the LED is blinked on and off at a first rate (e.g., between 400 HZ and 1000 HZ). This helps get away from DC, which helps the noise issues. Then, if while detecting a signal is detected that does not have the same frequency and is very close in phase to the frequency at which the LED is being driven, there is a likelihood that the light is coming from some other source (e.g., background light), so it is eliminated from the signal. Generally, the lock-in amplifier takes the signal, it averages the signal from when the LED is on and then it averages the signal from when the LED is off and it subtracts the two. This preferably results in a fluorescence signal with little noise.

As shown in FIG. 17C, In a preferred embodiment, the upper housing half 197a includes a lip or flange 258 that extends downwardly and overlaps another lip or flange 260 extending upwardly from the lower housing half 197b. The complementary flanges help block light for entering or exiting the light chamber 198 or the fluorescence chamber 207. Preferably, the flanges are offset from one another so that they overlap.

As discussed herein, the components of the optical system 77 are tuned specifically for the chemistry of an analysis cartridge and for this particular PD derivative and the amount of fluorescence that is to be measured. The ninety degree angle allows the photo detector 82 to detect the emitted light from the fluoresced CCM. In other words, the detector 82 is not receiving any light from the LED, but is only detecting the particles of aldehyde that get fluoresced.

From the description herein, it should be understood that the breath analysis system is used preferably to obtain a breath sample from a patient in the analysis cartridge 14 and then the breath sample is analyzed in the analysis device 16. Once the analysis cartridge 14 is placed in the analysis pocket 58 in the analysis device 16 and extends down into the well 173, the rotation assembly 76 rotates the analysis cartridge 14 a number of times to mix the contents, to move the filter assembly 19 from the breath chamber 30 to the fluid chamber 32 and to let the optical system 77 perform an analysis.

Figure 21A:
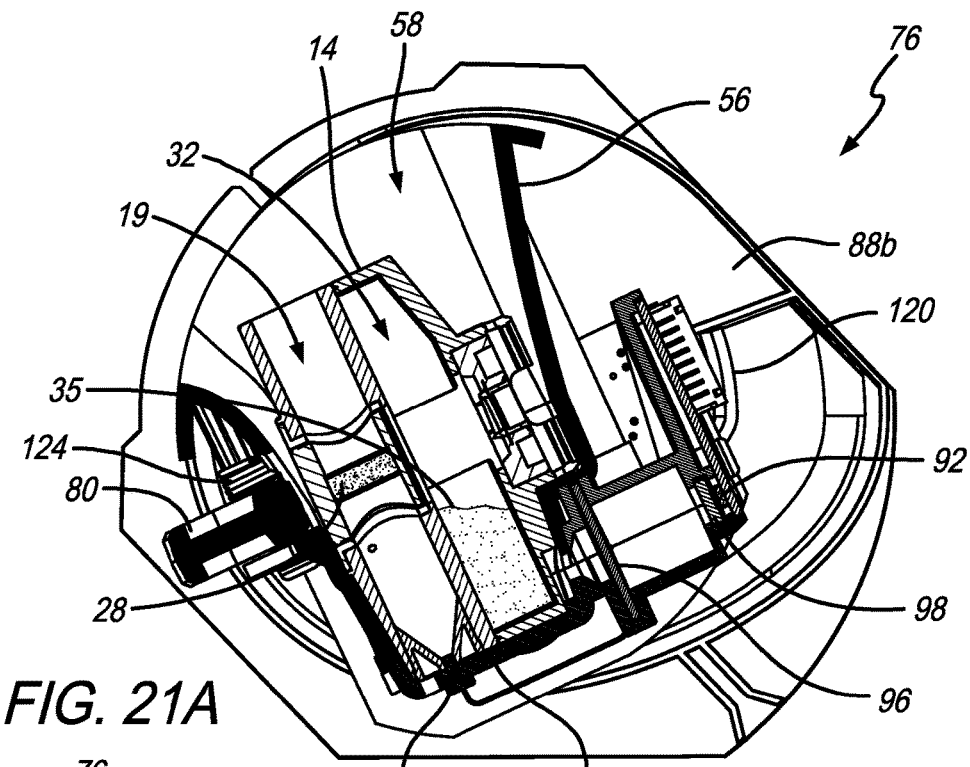
FIG. 21A is a cross-sectional end view of the rotation assembly showing the rotatable portion in the first position (also referred to as the start position)

FIGS. 21A-23 show the steps for how the rotation assembly 76 mixes the PD solution 35, moves the filter assembly 19 from the breath chamber 30 to the fluid chamber 32, mixes the PD solution and breath aldehydes (CCM) to form a fluorescing solution 206 and how the optical system 77 performs an analysis of the fluorescing solution 206. Each of the figures shows a cross-sectional end elevation view of the rotation assembly 76 with the analysis cartridge 14 in the analysis pocket 58. In a preferred embodiment, as shown in FIG. 21A, when the analysis cartridge is placed in the analysis pocket 58 and the back extends through the analysis opening 200 down into the well 173, an alignment member 208 is received in the breath exit hole 40.

Figure 21B:
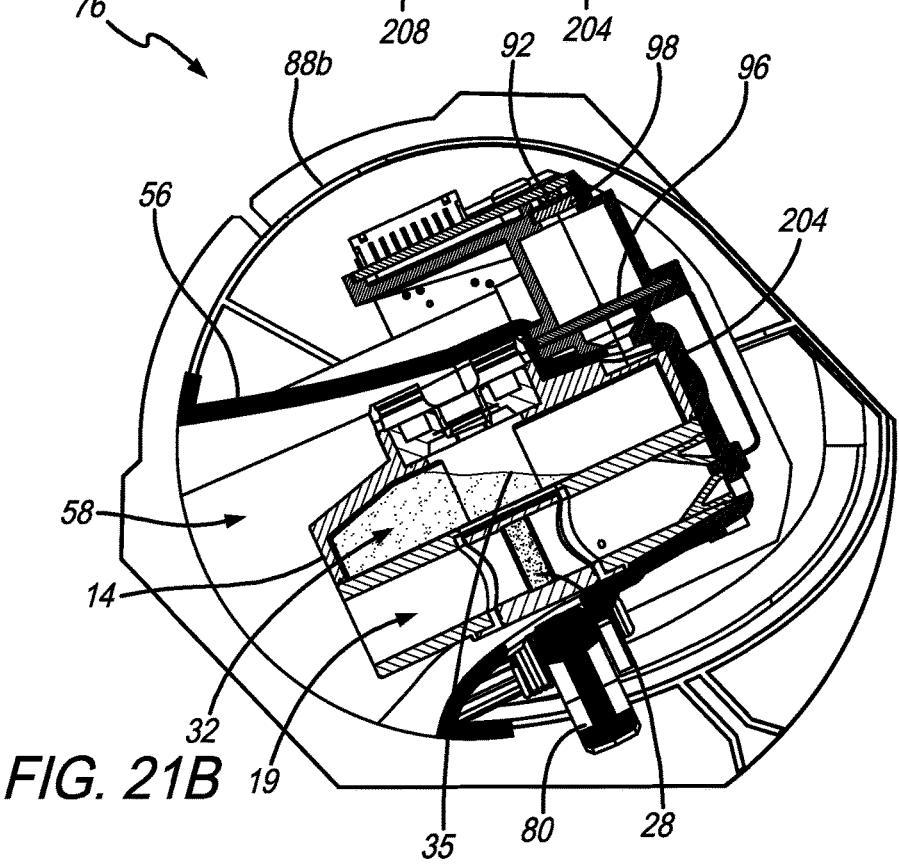
FIG. 21B is a cross-sectional end view of the rotation assembly showing the rotatable portion in the second position (also referred to as the first mixing position)

In FIG. 21A, the analysis cartridge 14 is in the analysis pocket 58 in the rotation assembly 76 and is in the configuration as the clinician has just taken it off the handle assembly 12 and placed it in the analysis pocket 58 (referred to herein as the start position). In use, the rotation assembly 76 rotates the analysis cartridge 14 through at least one pivot or rotation to introduce or mix the PD derivative 24 into the elution solution 34. FIG. 21B shows the orientation of the rotatable portion 86 and the analysis cartridge 14 in a second position after rotation (referred to herein as a first mixing position). The rotatable portion 86 can move between the start position and the first mixing a predetermined number of times for proper stirring or mixing. As discussed above, the rotatable portion 86 is moved via motor 78 (see FIG. 15), which rotates the rotatable portion 86 and basically sloshes the PD solution 35 back and forth to make sure that the PD derivative 24 is completely in solution. This is the mixing step.

Figure 21C:
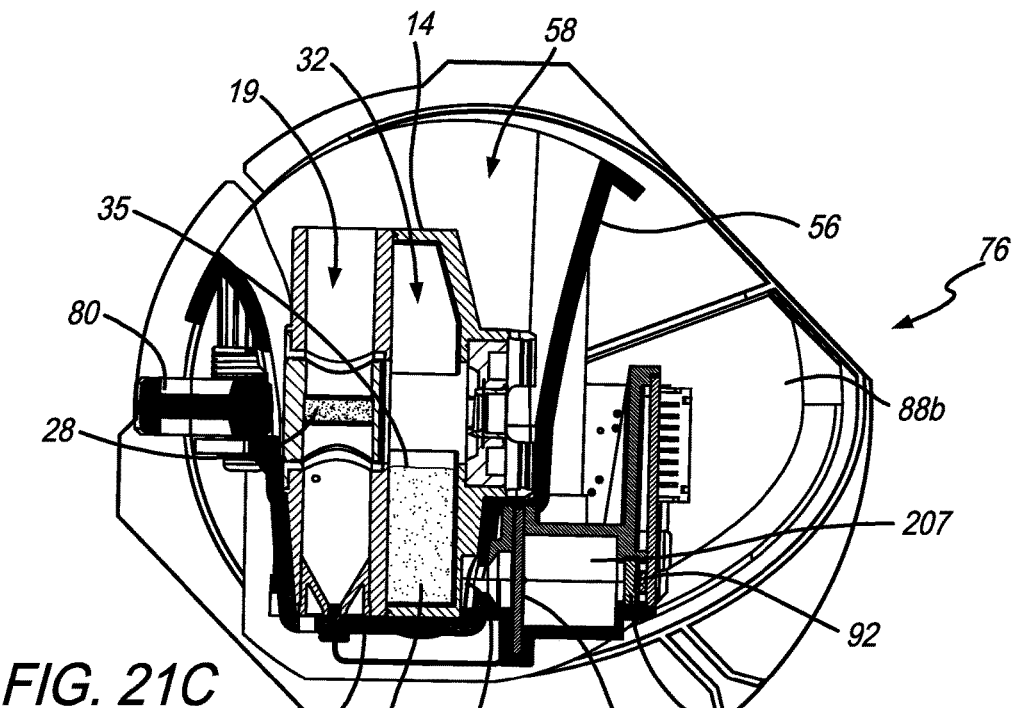
FIG. 21C is a cross-sectional end view of the rotation assembly showing the rotatable portion in the third position (also referred to herein as the baseline reading position)

FIG. 21C shows the orientation of the rotatable portion 86 and the analysis cartridge 14 in a third position (referred to herein as a baseline reading position). At this step (referred to herein as a baseline reading step), the analysis cartridge 14 is pivoted so that the fluid chamber 32 is straight up and down. Therefore, all of the PD solution 35 is in the rear portion or sensing chamber 32b of the fluid chamber 32. At this point a baseline fluorescence reading is taken by the optical system 77. In a preferred embodiment, this is done by turning on the LED 79 (the main circuit board 74 communicates with the first optical circuit board 162) and measuring the fluorescence of the PD solution 35 without any CCM therein, using detector 82. The baseline reading is communicated by the second optical circuit board 160 to the main circuit board 74.

Figure 21D:
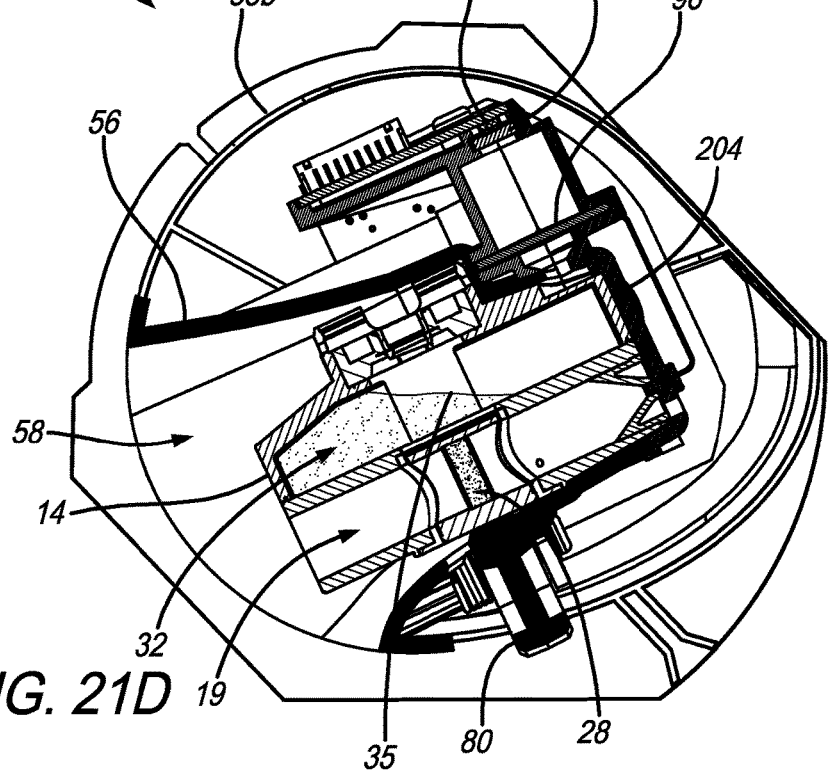
FIG. 21D is a cross-sectional end view of the rotation assembly showing the arm in a stowed position and the rotatable portion rotating toward the fourth position.
Figure 21E:
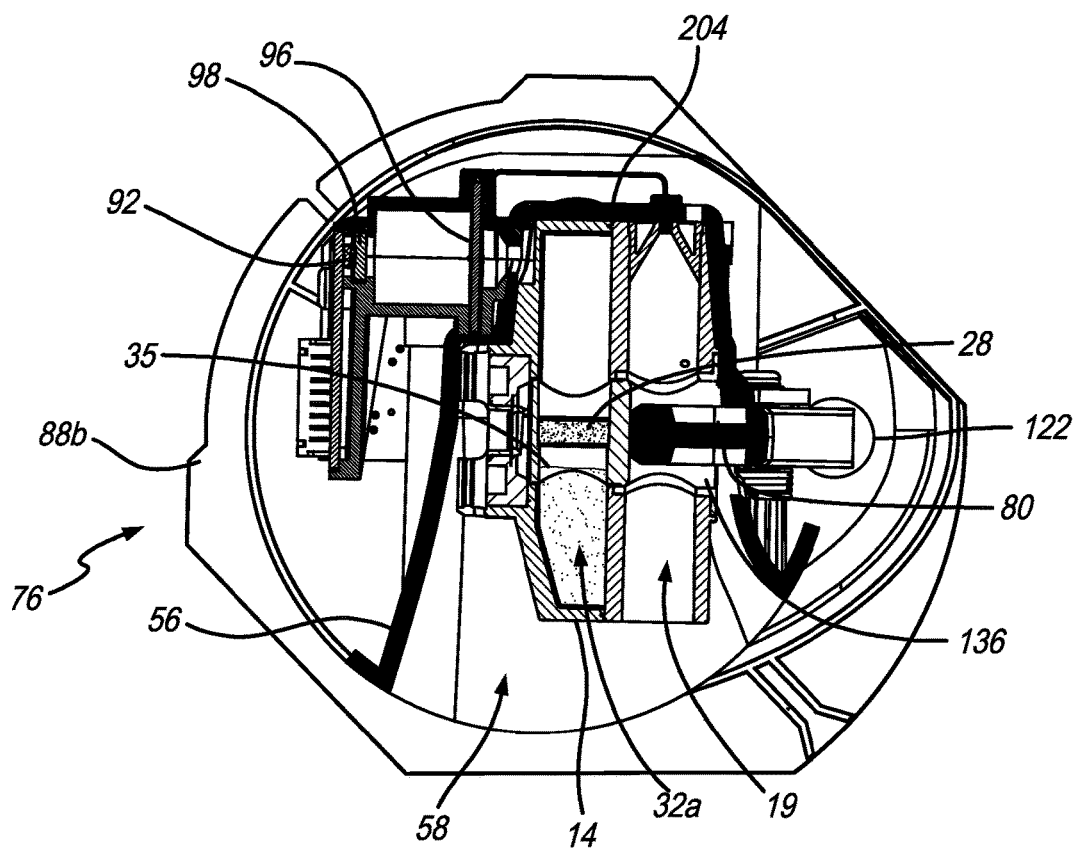
FIG. 21E is a cross-sectional end view of the rotation assembly showing the rotatable portion in a fourth position (also referred to as the insertion position) and the arm in the deployed position.

Next, as shown in FIGS. 21D-21E, the rotatable portion 86 and shroud 56 (and the analysis cartridge) move through and past the first mixing position (shown in FIG. 21D) and to a fourth position shown in FIG. 21E (referred to herein as the insertion position), where the arm 80 pushes on the filter assembly 19 and moves it along the filter assembly path P2 (see FIG. 2) from the breath chamber 30 to the fluid chamber 32. In other words, in this step, the filter assembly 19 is inserted into the fluid chamber 32 by the arm 80. When this happens, the second breakable barrier 36b is broken. It will be appreciated that the arm 80 pushes filter assembly 19 as a result of the cam path 120 discussed above. As shown in FIG. 21D, the arm 80 is still in the stowed position after the baseline reading step. Therefore, during the mixing step and the baseline reading step and the rotation between the start position, the first mixing position, and the analysis position, the cam path 120 is configured such that the arm 80 remains in the stowed position. However, when the rotatable portion 86 rotates beyond the first mixing position, the increasing radius of the cam surface 120 pushes the ball bearing 122 outwardly, thereby pivoting the second end 80b of the arm 80 and pushing the filter assembly 19 inwardly, as shown in FIG. 21E. In this position, all of the fluid is down in the front portion 32a of the fluid chamber 32 and the filter assembly 19 (frit plates 26 and substrate 28) is now in the fluid chamber 32. However, the PD solution 35 has not yet touched any of the frit plates 26 or substrate 28 because of the fluid volume.

Figure 22:
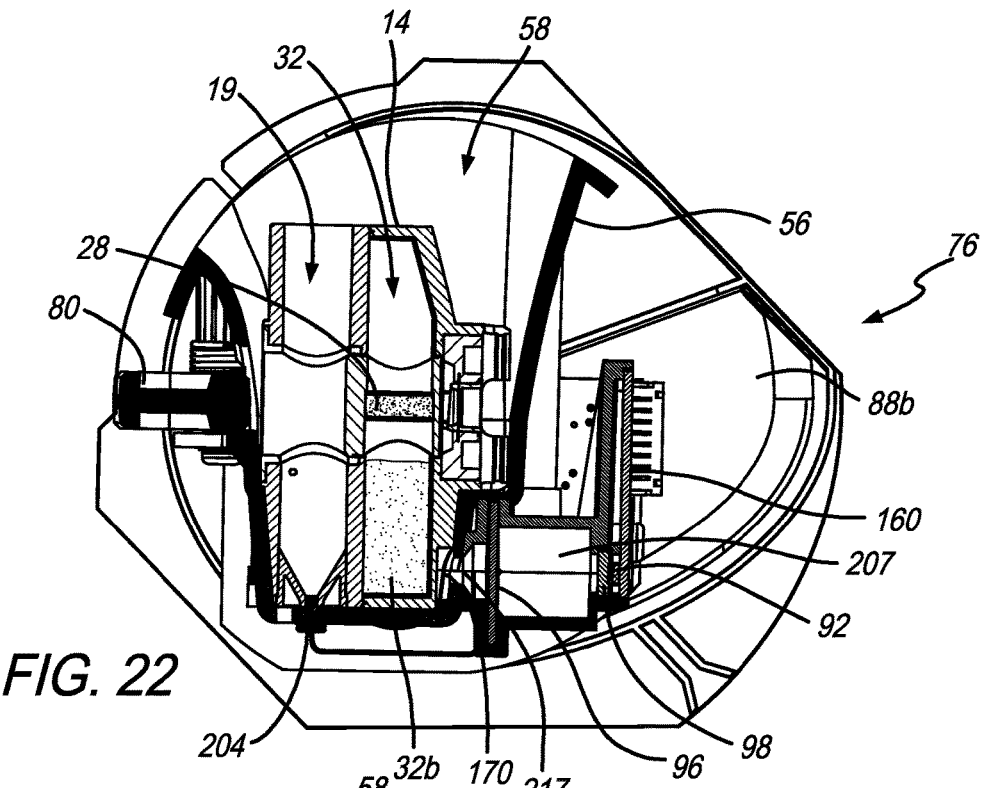
FIG. 22 is a cross-sectional end view of the rotation assembly showing the rotatable portion in the fifth position (also referred to as the analysis position)

Next, as shown in FIG. 22, the rotatable portion 86 and shroud 56 (and the analysis cartridge) rotate to a fifth position (referred to herein as the analysis position), where the fluid chamber 32 is once again straight up and down. It will be appreciated that the positioning of the rotatable portion 86 is the same in the analysis position and the baseline reading position. In this position, the PD solution 35 filters through opening 17 in the frit stack holder 20 and the frit plates 26 and the substrate 28 thereby immersing the frit plates 26 and the silica 28 in the PD solution 35. Also, the arm 80 has retracted back to the stowed position, but the filter assembly 19 has stayed in place. As the PD solution drains down and drips through the frit plates 26 it washes the CCM off the substrate 28 and into solution (referred to herein as the fluorescing solution 206). The analysis cartridge 14 is left in this orientation for a predetermined amount of time; enough time for the PD solution 35 to drain through and collect in the sensing chamber 32b of the fluid chamber 32 (the drainage step). During this step, the CCM are labeled or painted with the PD solution. In another embodiment, another mixing step can be added to further mix the fluorescing solution. Next, a fluorescence reading is taken by the optical system 77 to analyze the fluorescing solution. The original reading was the baseline without any CCM in the solution and now a measurement with CCM is taken.

Figure 23:
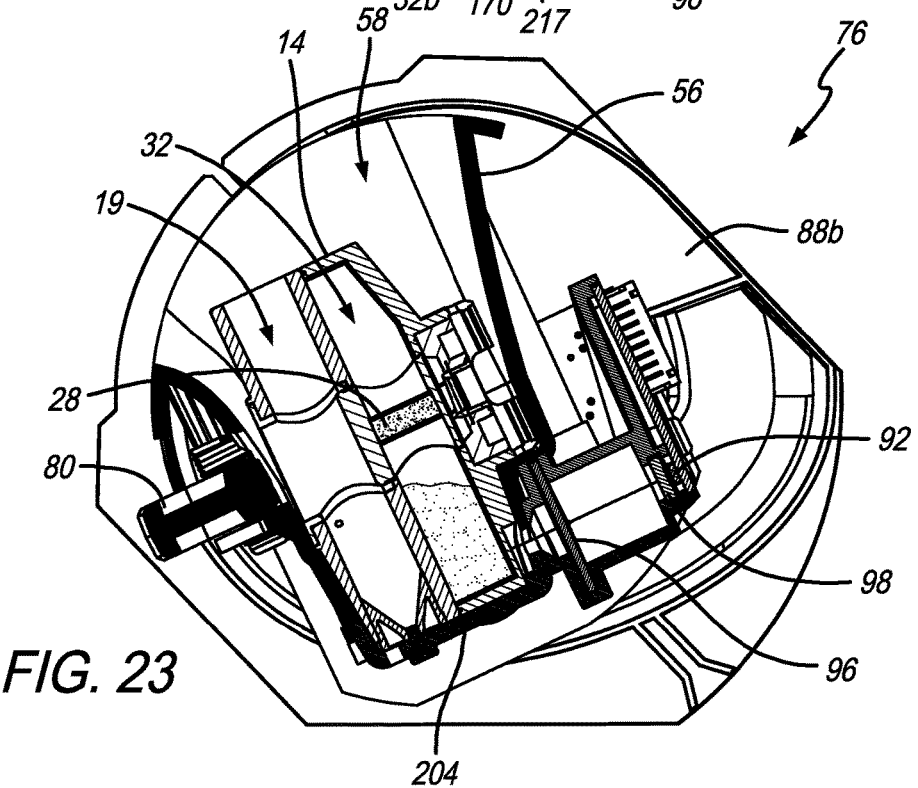
FIG. 23 is a cross-sectional end view of the rotation assembly showing the rotatable portion in the sixth position, where the analysis cartridge can be removed.

After the analysis step, the rotation assembly 76 rotates to a sixth position, which is the same as the first position. In other words, the rotatable portion 86 returns to the start position so that the analysis cartridge 14 can be removed, as shown in FIG. 23. The analysis cartridge 14 can then be disposed. In a preferred embodiment, all the steps described above are done automatically. Basically, the user opens the door 54, puts the analysis cartridge 14 in, closes the door 54 and hits go or the like on the display 60.

FIGS. 24-29 show another embodiment of the present invention where some of the steps discussed above with the analysis cartridge 14 are divided into system that includes a breath analysis cartridge 220 and a fluorescence analysis cartridge 222. The two cartridges together are referred to herein as an analysis cartridge system 219. The structure of both the breath analysis cartridge 220 and a fluorescence analysis cartridge 222 is similar to the analysis cartridge 14 described above so that they can fit into the analysis pocket 58, as described below. Like numerals in FIGS. 24-29 refer to like components in FIGS. 1-23.

The analysis cartridge system 219 is used to capture breath aldehydes (CCM) and analyze them with the optical system 77 in the device similar to the breath cartridge and system described above. The general steps in using the analysis cartridge system 219 are as follows: 1) blow through the breath chamber 30 in the breath analysis cartridge 220 to capture CCM; 2) place the breath analysis cartridge 220 in the analysis pocket 58; 3) allow the rotation assembly 76 and arm 80 to push move the filter assembly 19 from the breath chamber 30 to the fluid chamber 32 where the CCM mix with the elution solution 34 to form a CCM solution; 4) remove the breath analysis cartridge 220 from the analysis pocket 58; 5) move the ampule member from the first position to the second position to allow the CCM solution to mix with the PD derivative to form painted CCM solution 209; 6) connect the breath analysis cartridge 220 to the fluorescence analysis cartridge 222 so the painted CCM solution drains into the upper chamber of the fluorescence analysis cartridge 222 and through the filter assembly 19. The substrate 28 in the filter assembly 19 captures the painted CCM from the painted CCM solution 209 and the absorption member 238 absorbs the remaining solution; 7) place the fluorescence analysis cartridge 222 in the analysis pocket 58; 8) allow the rotation assembly 76 and arm 80 to move the filter assembly 19 from the breath chamber 30 to the fluid chamber 32 where the painted CCM is eluted into a second elution solution 202 to form the fluorescing solution 206; 9) perform a fluorescence detection analysis of the fluorescing solution 206 with the optical system 77. In a preferred embodiment, the second elution solution rinse comprises greater than 50% acetonitrile and preferably 90% ethanol.

Figures 25, 25A:
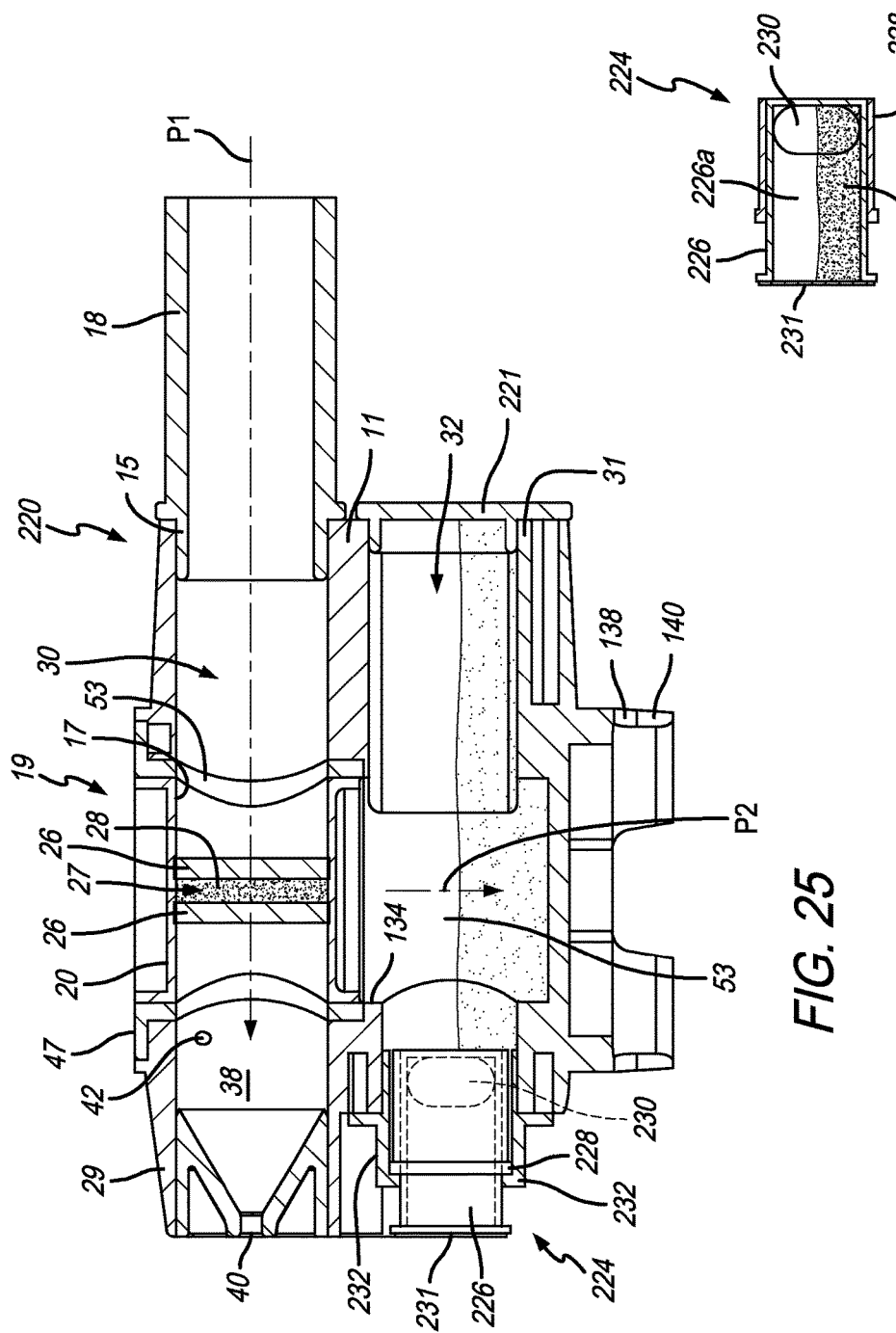
FIG. 25 is a cross-sectional view of the breath analysis cartridge of FIG. 24 with the ampule assembly in elevation.
FIG. 25A is a cross-sectional view of the ampule assembly of the breath analysis cartridge.

As shown in FIG. 25, the breath analysis cartridge 220 includes an upper or breath chamber 30, a fluid chamber 32 and a filter assembly 19 (with substrate 28 therein). A cap 221 plugs and seals the fluid chamber 32. Breath analysis cartridge 220 includes an ampule assembly 224 positioned in the back of the fluid chamber 32. Elution solution 34 is disposed in the fluid chamber 32, and the fluid chamber 32 is sealed from the breath chamber 30. This can be done by a breakable foil barrier, as described above or by another sealing method. For example, the frit stack holder 20 can seal the filter assembly opening 134. In use, a patient blows through breath chamber 30 so that breath aldehydes are collected on the substrate 28. Next, the breath analysis cartridge 220 is placed in the analysis pocket 58 in the start position (see FIG. 21A). Then the rotation assembly 76 rotates the shroud 56 and breath analysis cartridge 220 to the insertion position (see FIG. 21E) so that the filter assembly 19 moves from the breath chamber 30 to the fluid chamber. In the fluid chamber the CCM are eluted into the elution solution 24 to form the CCM solution. The breath analysis cartridge 220 is then removed from the analysis pocket 58.

Figure 24:
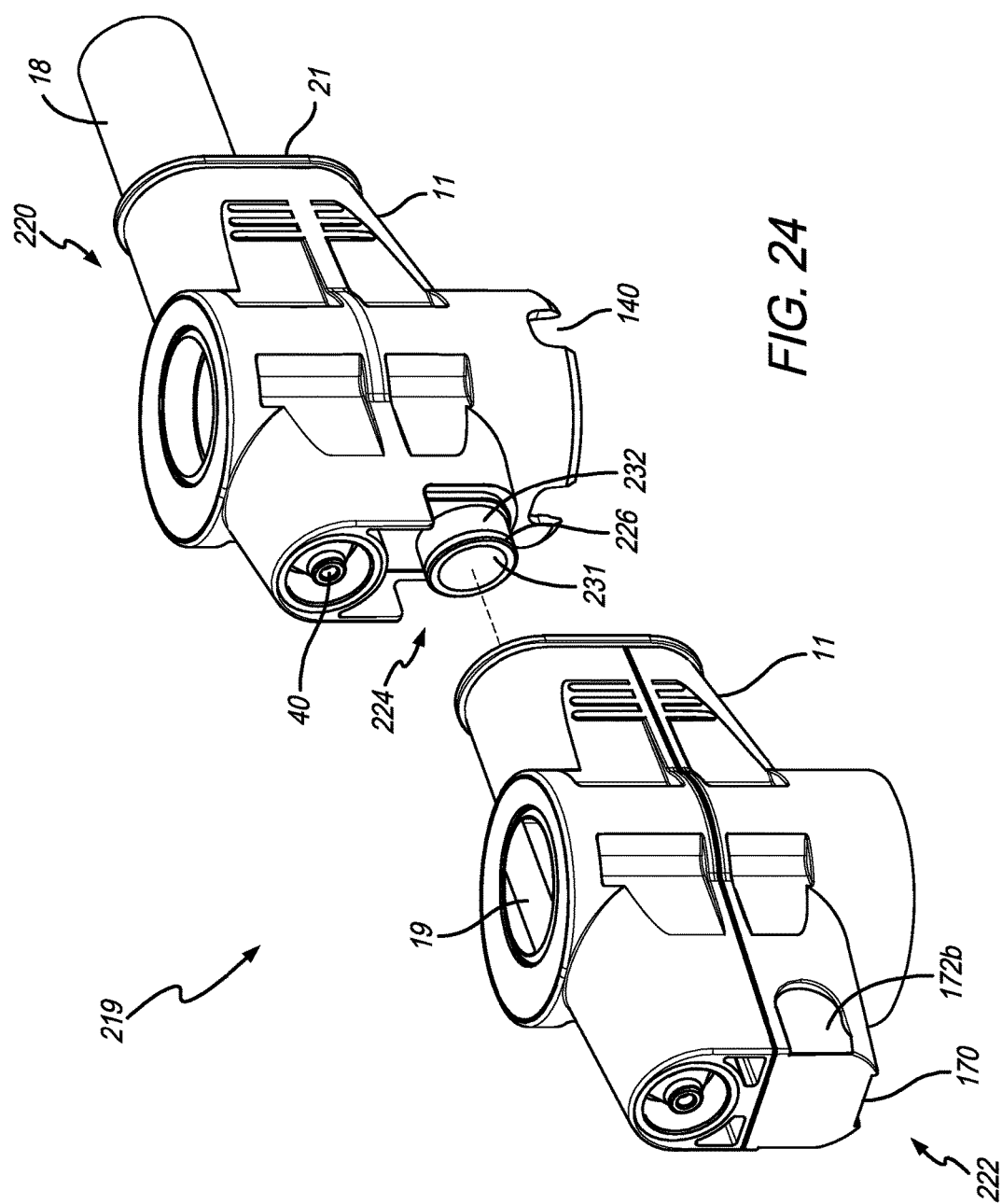
FIG. 24 is an exploded perspective view of an analysis cartridge system that includes a breath analysis cartridge and a fluorescence analysis cartridge in accordance with another preferred embodiment of the present invention.
Figures 26, 26A:
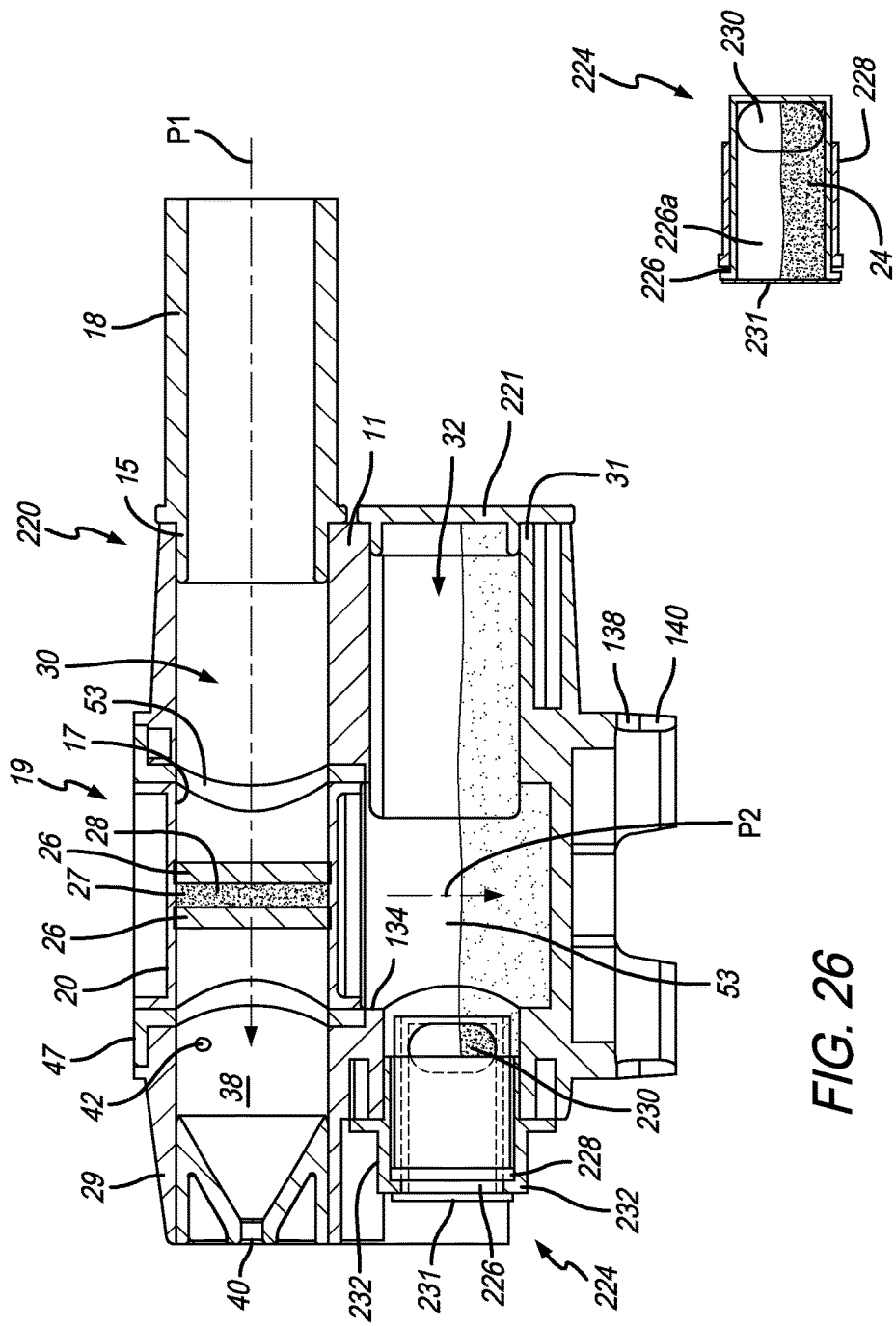

In a preferred embodiment, the ampule assembly 224 includes an ampule member 226 that is received in and slidable within a slide tube 228. The ampule member 226 is preferably a cylinder that defines an interior 226a, includes enclosed ends and has at least one and preferably two fluid openings 230 defined in the sidewall thereof. The end that protrudes outside of the fluid chamber is enclosed with a breakable barrier 231. As shown in FIG. 25, the PD derivative 24 is disposed in the ampule member interior or fluorescence chromophore space 226a. The ampule member 226 is movable within the slide tube 228 between a first position where the PD derivative 24 are separated from the fluid chamber 32 and a second position where the ampule member interior 226a is in communication with the fluid chamber 32. In a preferred embodiment, when the ampule member 226 is in the first position, the fluid openings 230 are positioned inside the slide tube 228 and are therefore sealed from allowing the elution solution 34 therein, as shown in FIG. 25. However, when the ampule member 226 is slid to the second position, the openings 230 are now in flow communication with the fluid chamber 32, which allows fluid in the fluid chamber 32 to enter the ampule member interior 226a. FIG. 26 shows the ampule member 226 in the second position. As shown in FIGS. 24-25, in a preferred embodiment, the ampule assembly 224 is housed in a receiver member 232 that mates with the fluorescence analysis cartridge 222 as described below. In use, after removing the breath analysis cartridge 220 from the analysis pocket 58, as described above, the user presses the ampule member 226 and moves it from the first position to the second position.

Figure 27:
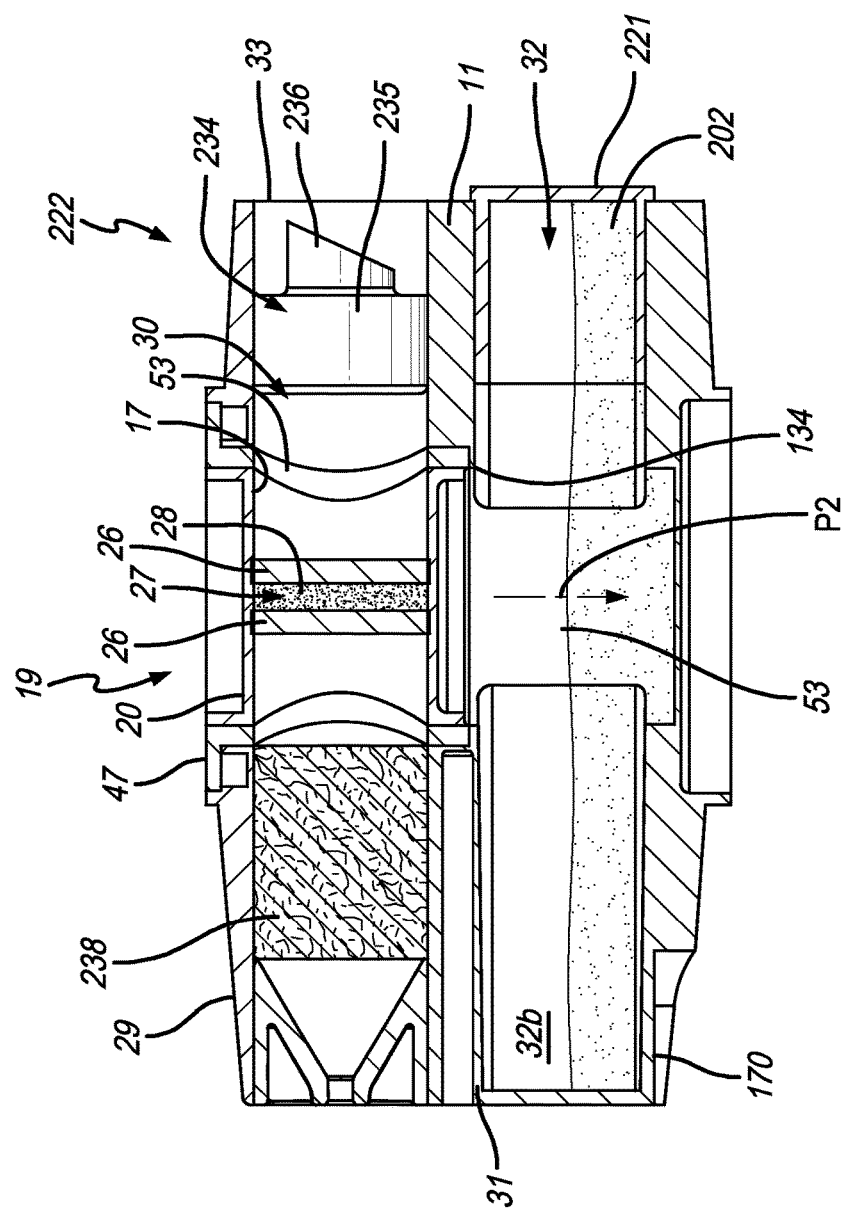
FIG. 27 is a cross-sectional view of the fluorescence analysis cartridge of FIG. 24.

As shown in FIG. 27, in a preferred embodiment, the fluorescence analysis cartridge 222 includes an upper chamber 30, a fluid chamber 32 and a filter assembly 19 (with substrate 28 therein). The second elution solution 202 is disposed in the fluid chamber 32. A cap 221 plugs and seals the fluid chamber 32. A piercing member 234 is disposed in the upper chamber 30 adjacent the front opening 33. The piercing member 234 is a hollow tubular member that includes a main body portion 235 with a piercer 236 extending therefrom. The piercer 236 has a smaller diameter than the main body portion and the upper chamber 30.

Figure 28:
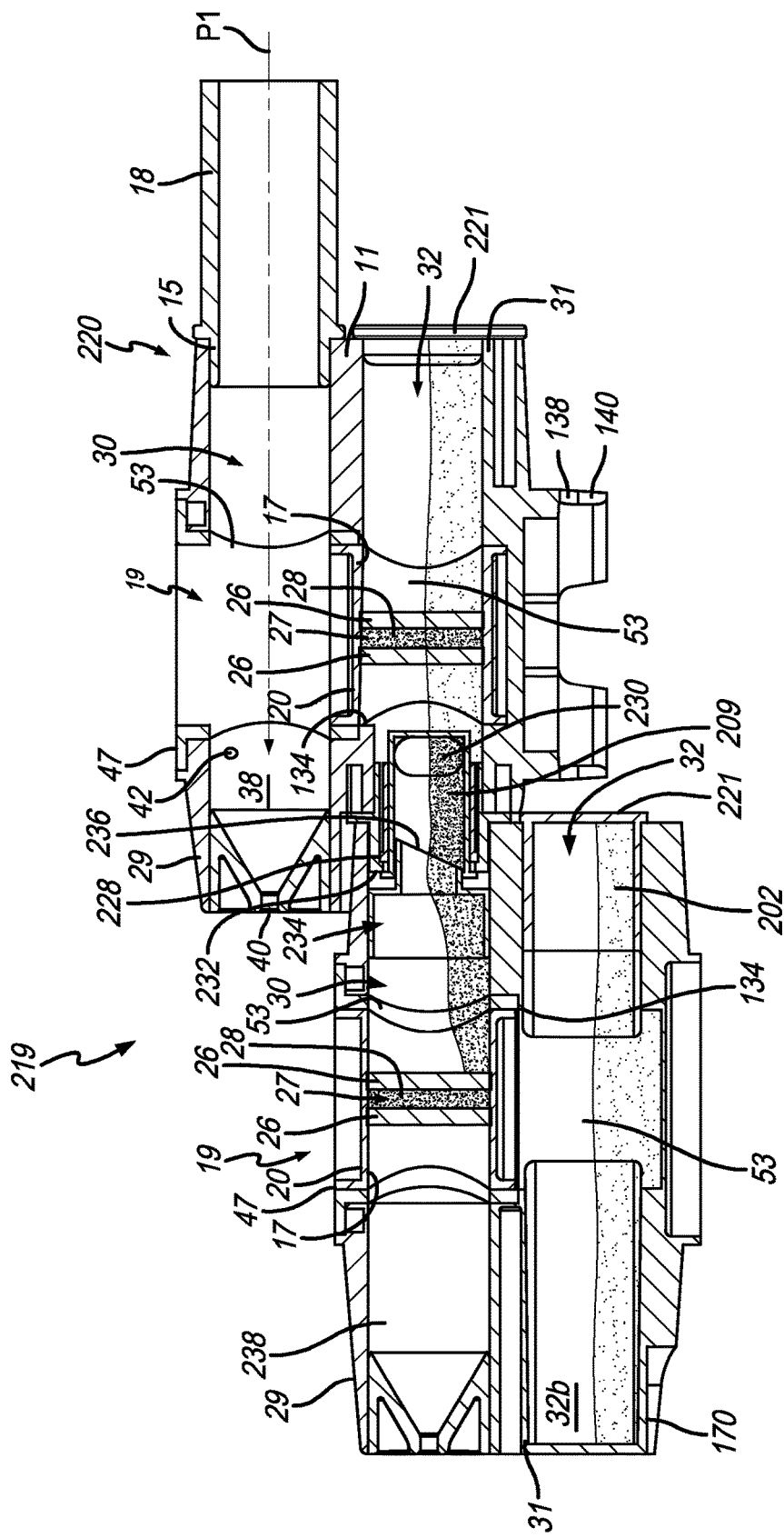
FIG. 28 is an elevational view of the analysis cartridge system of FIG. 24 with the breath analysis cartridge received on the fluorescence analysis cartridge.
Figure 29:
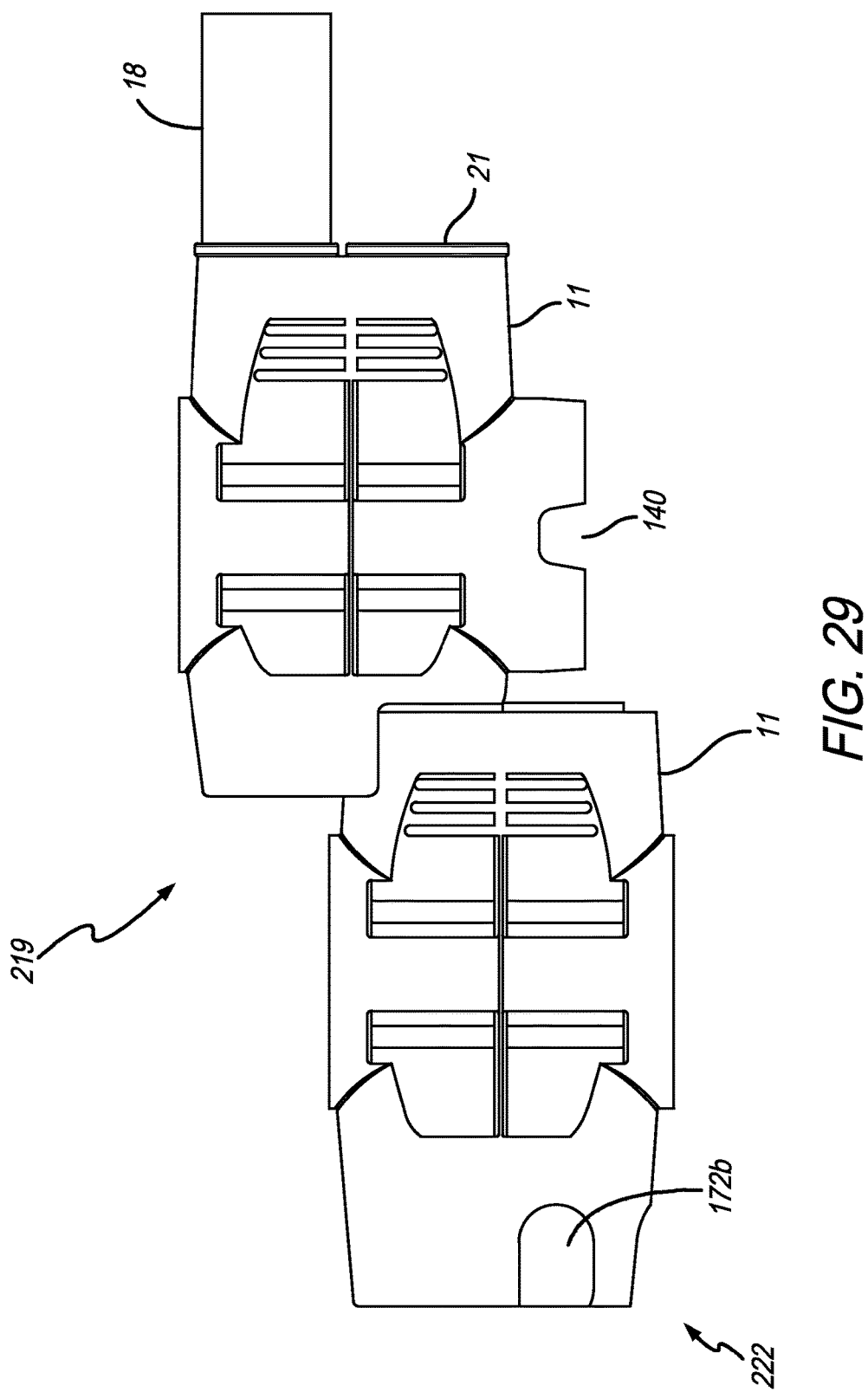
FIG. 29 is a cross-sectional view of the analysis cartridge system of FIG. 24.

In use, as shown in FIGS. 28-29, the receiver member 232 of the breath analysis cartridge 220 is inserted into the front opening 33 of the fluorescence analysis cartridge 222. The piercer 236 then pierces the breakable barrier 231 thereby communicating the ampule member interior 226a with the lower chamber 32 of the fluorescence analysis cartridge 222. When the breakable barrier 231 is pierced, the painted CCM solution 209 flows into the upper chamber 30 of the fluorescence analysis cartridge 222 and washes over the filters 26 and substrate 28 in the filter assembly 19 and the painted CCM are captured by the substrate 28. Any excess solution is absorbed in the absorption member 238 in the rear of the upper chamber 30.

The fluorescence analysis cartridge 222 is then placed in the analysis pocket 58 in the analysis device 16 in the start position (see FIG. 21A). The rotation assembly 76 then rotates the fluorescence analysis cartridge 222 to the insertion position (see FIG. 21E) where the painted CCM is eluted into the second elution solution 202 to form the fluorescing solution 206. The rotation assembly 76 then rotates the fluorescence analysis cartridge 222 to the analysis position (see FIG. 22) and a fluorescence analysis of the fluorescing solution 206, as described above, is performed.

Figure 30:
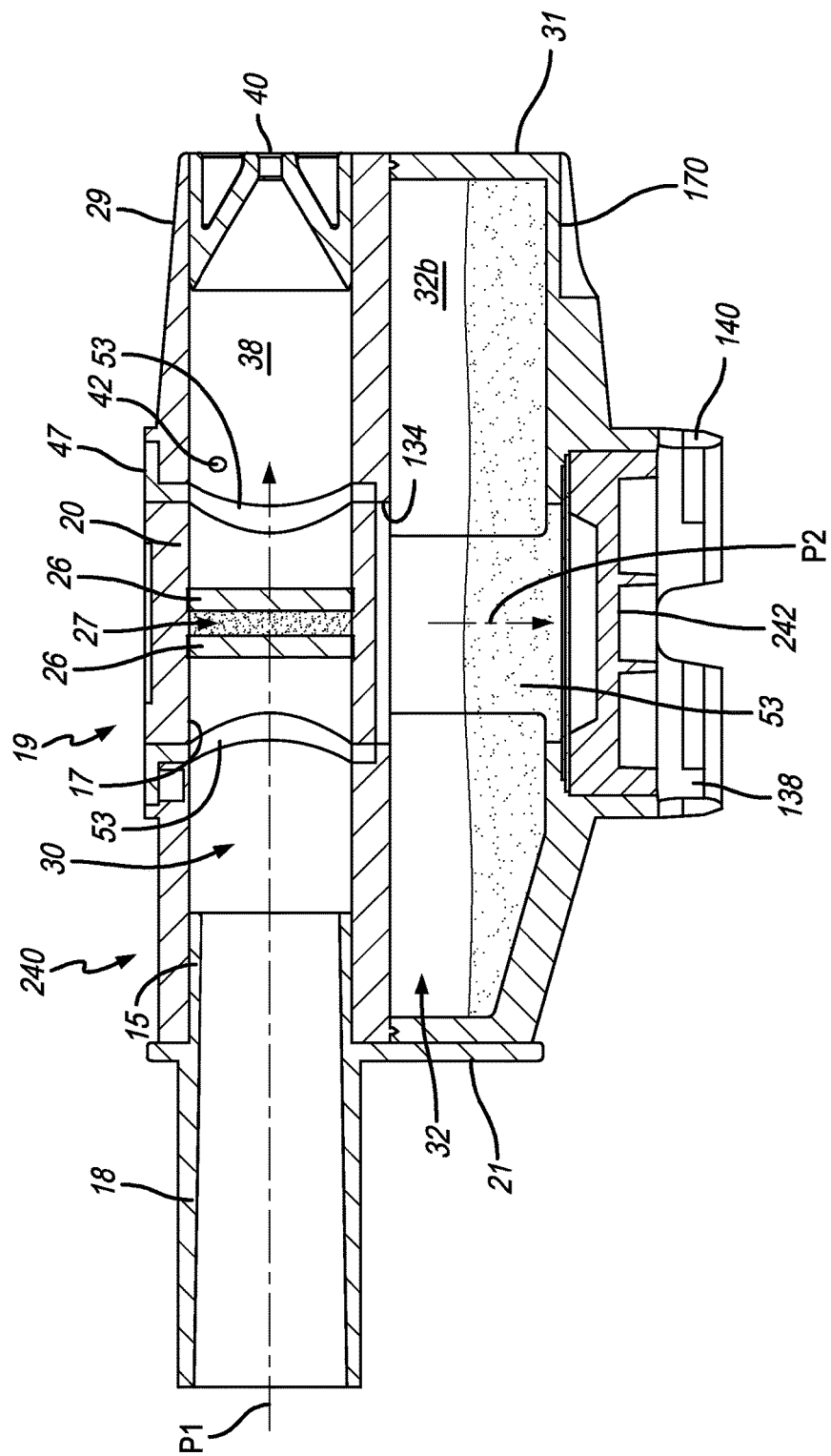
FIG. 30 is a cross-sectional view of an analysis cartridge in accordance with another preferred embodiment of the present invention.

FIG. 30 shows another embodiment of an analysis cartridge 240. The structure of analysis cartridge 240 is similar to the analysis cartridge 14 described above so that they can fit into the analysis pocket 58, as described below. Like numerals in FIG. 30 refer to like components in FIGS. 1-29. As shown in FIG. 30, the analysis cartridge 240 includes an upper chamber or breath chamber 30, a fluid chamber 32, a filter assembly 19 (with filters 26 separated by a substrate space 27) and a vent cap 242 to seal the fluid chamber 32. Substrate that is pre-loaded with the PD derivative (referred to herein as PD substrate) is disposed in substrate space 27 and elution solution 34 is disposed in the fluid chamber 32.

In use, the analysis cartridge 240 is placed on the handle assembly 12, a user blows through the mouthpiece 18 and the breath chamber 30 for a predetermined amount of time and at a predetermined pressure (or within a predetermined pressure range) until CCM are collected on the PD substrate 241. After the CCM have been collected, the user removes the analysis cartridge 240 from the handle assembly 12, removes the mouthpiece 18 and places the analysis cartridge 240 in the analysis device 16.

At first, the analysis cartridge 240 is in the analysis pocket 58 in the start position (see FIG. 21A). In a preferred embodiment, no first mixing or baseline reading step is needed. However, in another embodiment, these steps can be included. The rotation assembly 76 then rotates the analysis cartridge 14 through and past the position shown in FIG.

21D and to the insertion position where the arm 80 pushes on the filter assembly 19 and moves it along the filter assembly path P2 from the breath chamber 30 to the fluid chamber 32. In other words, in this step, the filter assembly 19 is inserted into the fluid chamber 32 by the arm 80. It will be appreciated that the arm 80 pushes filter assembly 19 as a result of the cam path 120 discussed above. When the rotatable portion 86 rotates to the insertion position the increasing radius of the cam surface 120 pushes the ball bearing 122 outwardly, thereby pivoting the second end 80b of the arm 80 and pushing the filter assembly 19 inwardly, as shown in FIG. 21E. In this position, all of the fluid is down in the front portion 32a of the fluid chamber 32 and the filter assembly 19 is now in the fluid chamber 32. However, the elution solution 34 has not yet touched any of the frit plates 26 or the PD substrate 241 because of the fluid volume.

Next, as shown in FIG. 22, the rotatable portion 86 and shroud 56 (and the analysis cartridge) rotate to the analysis position, where the fluid chamber 32 is once again straight up and down. In this position, the elution solution 34 filters through opening 17 in the frit stack holder 20 and the frit plates 26 and the PD substrate 241 thereby immersing the frit plates 26 and the PD substrate 241 in the elution solution 34. As the elution solution 34 drains down and drips through the frit plates 26 it washes the painted CCM off the PD substrate 241 and into solution (referred to herein as the fluorescing solution 206). The analysis cartridge 240 is left in this orientation for a predetermined amount of time; enough time for the elution solution 34 to drain through and collect in the sensing chamber 32b of the fluid chamber 32 (the drainage step). In another embodiment, another mixing step can be added to further mix the fluorescing solution. Next, a fluorescence reading is taken by the optical system 77 to analyze the fluorescing solution.

After the analysis step, the rotation assembly 76 rotates back to the start position so that the analysis cartridge 240 can be removed, as shown in FIG. 23. The analysis cartridge 240 and can then be disposed.

The analysis device 16 and the screen 60 thereof includes the ability to walk a patient and the practitioner through the steps necessary to perform a breath analysis. For example, the screen provides a user with feedback on, for example, the flow rate to let a patient know if they are blowing too hard or too soft.

An exemplary set of steps using the system 10 and the user interface (UI) on the screen 60 is described below. It will be understood that this is only exemplary and that steps can be rearranged and/or omitted or added as desired. Furthermore, it will be understood that all entries are being made on the UI. In another embodiment, the UI buttons and keypad can be manual buttons and a keypad. The practitioner steps are as follows: 1) Turn on the device by pressing the power button 62 located above the touchscreen. 2) Press the start button on the UI. 3) Press the list button on the bottom left of the UI keypad and select the practitioner name in the upper right corner. This auto-populates the Practitioner ID. Press the go button. 4) Enter the Patient ID in the Patient ID field (could be a number or the patient email address). Press the go button. 5) Enter the 6-digit lot number in the analysis cartridge lot number field. Press the go button. 6) Open the analysis cartridge package. 7) Remove the handle assembly 12 from the handle storage pocket 66. Press the arrow button ">" to continue. 8) Give the breath capture assembly 13 to the patient. Press the arrow button ">" to continue. 9) Press start.

The patient steps are as follows. 1) Press "tap to start". 2) Deliver breath sample by blowing through the mouthpiece 18, keeping the circle in the green zone on the UI. A ring will appear on the outside of the circle that represents the total volume. Maintain the green circle until the ring shows 100% complete. 2) When 100% total volume is reached, stop blowing and give handle to practitioner.

Continued practitioner steps are as follows. 10) Press "next". 11) Disconnect the analysis cartridge 14, 220 or 240 from the handle assembly 12. Press the arrow button ">" to continue. 12) Place the handle assembly back in the handle storage pocket 66. Press the arrow button ">" to continue. 13) Disconnect the mouthpiece 18 from the analysis cartridge 14, 220 or 240. Press the arrow button ">" to continue. 14) Open the door 54. Press the arrow button ">" to continue. Insert the analysis cartridge 14, 220 or 240 into the analysis pocket 58. Press the arrow button ">" to continue. 15) Close the door 54. 16) Press "done". 17) The analysis device 16 will begin processing the sample. When it is finished, it will display "100%." 18) Tap to reveal the score. 19) Press "done".

It will be appreciated that if the analysis cartridge system 219 is used, the final few steps will change. After step 16 the steps are as follows. 17) The analysis device 16 will push the filter assembly 19 in the breath analysis cartridge 220 to the second position. When it is finished, it will display "done." 18) Open the door 54 and remove the breath analysis cartridge. 19) Press ampule member. 20) Connect breath analysis cartridge to fluorescence analysis cartridge to allow the painted CCM solution to enter fluorescence analysis cartridge. 21) Disconnect breath analysis cartridge from fluorescence analysis cartridge. 22) Insert the fluorescence analysis cartridge 222 into the analysis pocket 58. Press the arrow button ">" to continue. 23) Close the door 54. 24) Press "done". 25) The analysis device 16 will begin processing the sample. When it is finished, it will display "100%." 26) Tap to reveal the score. 27) Press "done".

If the device is connected to Wi-Fi, the device will automatically upload the test record to a portal. If not, it will store the score until it finds a secure connection. The score can also be uploaded via USB port 168.

It will be appreciated that modifications to the invention can be made. For example, the mouthpiece can be non-removable, The present invention is directed to a method and device useful for the detection, quantitation and assay of carbonyl containing moieties ("CCM") including aldehydes, preferably in biological samples, and preferably at low concentrations in the biological sample. In this regard, CCM is defined to include one or more different carbonyl containing moieties.

As used herein, a "biological sample" is referred to in its broadest sense, and includes solid and liquid or any biological sample obtained from nature, including an individual, body fluid, cell line, tissue culture, or any other source. As indicated, biological samples include body fluids or gases, such as breath, blood, semen, lymph, sera, plasma, urine, synovial fluid, spinal fluid, sputum, pus, sweat, as well as liquid samples from the environment such as plant extracts, pond water and so on. Solid samples may include animal or plant body parts, including but not limited to hair, fingernail, leaves and so on. The preferred biological sample for one embodiment of the present invention is the breath of a human.

A CCM is a compound having at least one carbonyl group. A carbonyl group is the divalent group >C=O, which occurs in a wide range of chemical compounds. The group consists of a carbon atom double bonded to an oxygen atom. The carbonyl functionality is seen most frequently in three major classes of organic compounds: aldehydes, ketones, and carboxylic acids. As used herein, "aldehyde" has its ordinary chemical meaning and the method of the present invention is useful in detecting the concentration of aldehydes in biological samples. In particular, the present invention is useful in detecting various forms of aldehydes include without limitation 1-hexanal, malondialdehyde, 4-hydroxynonenal, acetaldehyde, 1-propanal, 2-methylpropanal, 2,2-dimethylpropanal, 1-butanal, and 1-pentanal.

The amount of the CCM captured by the substrate may vary, but typically for a substrate consisting of 200 mg of 50-270 mesh (300-50 µm) particle with a bed diameter of 12.5 mm, generally, it will be equivalent to the amount in a human's breath after breathing into a tube like a breathalyzer. Preferably it will be from 75 to 0.1 ppb (400 to 4 pmoles) and more preferably from 20 ppb to 0.01 ppb (80 to 0.4 pmoles).

The invention is amenable to "mix & read" and "real-time" assay formats for the detection of CCM. The invention can be applied to the detection of CCM in solution. The invention can be applied to the detection of trace CCM in the gas phase by the addition of a primary capture (on a substrate as discussed below) and release (elution from the loaded substrate as discussed below) process. Preferably in one step of the process, gas phase CCM, for example, aldehydes from the breath of a human, are captured on a substrate.

The substrate of the present invention is desirably formed from a solid, but not necessarily rigid, material. The solid substrate may be formed from any of a variety material, such as a film, paper, nonwoven web, knitted fabric, woven fabric, foam, glass, etc. For example, the materials used to form the solid substrate may include, but are not limited to, natural, synthetic, or naturally occurring materials that are synthetically modified, such as polysaccharides (e.g., cellulose materials such as paper and cellulose derivatives, such as cellulose acetate and nitrocellulose); polyether sulfone; polyethylene; nylon; polyvinylidene fluoride (PVDF); polyester; polypropylene; silica; inorganic materials, such as deactivated alumina, diatomaceous earth, $MgSO_4$, or other inorganic finely divided material uniformly dispersed in a porous matrix, with polymers such as vinyl chloride, vinyl chloridepropylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and so forth. Preferably the substrate is a solid phase matrix of silica optionally spaced between frits. The size of the substrate is chosen so that a measurable amount of CCM is captured by the substrate. The size can vary but generally it is about 2 mL, preferably about 1mL and more preferably about 0.25 mL.

The substrate typically consists of a bed of particles with 50-60 angstrom pores, with a 50-270 mesh (300-50 µm), and a mass of 75 to 300 mg, preferably 60-120 mesh (250-125 µm) with a mass of 100 to 200 mg and more preferably 50-120 mesh (210-125 µm) with a mass of 125 to 175 mg.

In another step of the process, a fluorescence chromophore such as a phenylene diamine derivative is added to an elution solution to form a phenylene diamine solution. Phenylene diamine derivatives useful in connection with the present invention include but are not limited to many phenylene diamine derivatives including without limitation meta-phenylene diamine ("mPDA") and its derivatives, with mPDA preferred for detecting aldehydes including without limitation 1-hexanal. While certain p-PDA or o-PDA derivatives may be useful in the method of the present invention, they are not useful for detecting 1-hexanal as they yield a cloudy colloidal suspension which is not useful for the optical based detection discussed below.

Other phenylene diamine derivatives include the following or mixtures thereof:

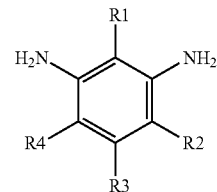

where R1, R2, R3, R4 are each independently selected from the group consisting of H, alkyl, substituted alky, alkoxy, substituted alkyoy, acyl, acylamino, acyloxy, amino, substituted amino, aminocarbonyl, aminothiocarbonyl, aminocarbonylamine, aminothiocarbonylamino, aminocarbonyloxy, aminosulfonyl, aminosulfonyloxy, aminosulfonylamino, amidino, carboxyl, carboxyl ester, (carboxylester) amino, (carboxy ester) oxy, cyano, halo, hydroxy, SO3-, sulfonyl, substituted sulfonyl, sulfonyloxy, thioacyl, thioal, alkylthio, substituted alkylthio, acyl, substituted aryl, heteroaryl, substituted heteroaryl, cycloalkyl, substituted cycloalkyl, heterocycles, and substituted heterocycles.

The mPDA derivative mPDA-orange (pyridinium,4-[2-[4-(diethylamino)phenyl-ethenyl]-1-[1-(3,5-diminobenzamide)-pentylamino-5-oxyhextyl]) leverages both a) the sensitivity to environmental changes and b) the potential to modulate the surfactant dependence of the mPDA-aldehyde induced polymerization. The scheme used to synthetize mPDA-orange is to conjugate mPDA to the styrylpyridinium moiety via an alkyl amide linker.

mPDA-orange exhibits a quantum yield increase as the molecule is incorporated into the aldehyde induced mPDA polymer. In addition, the excitation and emission properties of the styrylpyridinium moiety affords a FRET (Forster Energy Transfer) generated signal from the mPDA polymer. The styrylpyridinium moiety exhibits a broad excitation with a maximum at 470 nm and an emission maximum at 570 nm. The excitation profile provides sufficient overlap with the emission profile of the mPDA polymer to afford FRET based signal generation. A Fret based signal generation would be manifest by an excitation at the mPDA polymer (405 nm) and emission at the styrylpyridinium moiety emission at 570 nm.

A direct aldehyde induced polymerization of mPDA-orange alone does not generate a response signal due to quenching of the styrylpyridinium at the high concentrations required for induction of the polymer. A response would only be expected when the mPDA-orange is contained within a mixture of mPDA and mPDA-orange. Indeed, an aldehyde response is only observed when mPDA-orange is doped into mPDA at significantly dilute molar ratios mPDA/mPDA-orange 1,000:1 to 10,000:1. An increase in mPDA-Orange emission at 570 nm is observed when excited at 405 nm when 1 µM hexanal is added to the system. The increase in emission is not observed when the mPDA-orange styrylpyridinium moiety is excited directly at 470-490 nm. The response is approximately 3× over the background, where the conditions are 7 mM mPDA, 5 µM mPDA-orange (molar ration 15,000:1), 90 mM NaCl, 15% Ethanol, 0.1%

SDS, 50 mM citrate at ph 2.5. The excitation is at 405 nm and the emission at 575-585 nm. As can be seen, in the absence of aldehyde the background level remains fairly constant and auto induction leading to incorporation of mPDA-orange appears to be minimal Though the response for mPDA-orange is much less 3× versus 15× for mPDA alone the derivative offers several advantages: 1) increase wavelength discrimination afforded by the largeStokes shift between excitation and emission and 2) the enhanced baseline stability In general, the concentration of the phenylene diamine derivative in the phenylene diamine solution ranges from 0.5 mM to 25 mM. For mPDA, the mPDA concentration in the phenylene diamine solution generally ranges from 0.5 to 21 mM, preferably from 2 to 10 mM, and optimally 5 mM for aldehydes such as 1-hexanal. Notwithstanding the foregoing, for mPDA-orange, it must be diluted into mPDA at a low molar ration, preferably 1000-10,000.

In general, the elution solution includes a salt, a buffer, a surfactant, and an organic solvent. The concentration of the salt ranges can from 5 mM to 200 mM and preferably from 20 mM to 80 mM; the concentration of the buffer can range from 25 mM to 200 mM and preferably from 40 mM to 60 mM; and the concentration of the surfactant can range from 0.05% (1.7 mM) to 0.4% (13.9 mM), and preferably from 0.15% (5.2 mM) to 0.25% (8.7 mM). Optimally 0.2% or 6.96 mM is used. The salt can be any salt that does not negatively impact the fluorescing solution and controls salting effects in the elution solution, and may include NaCl, LiCl, KCl, sulfates and phosphates, and mixtures thereof, with NaCl preferred.

The buffer is employed to maintain the elution solution mildly acidic and preferably at a pH of between 2 and 4.5, more preferably 2.5. The buffer can be a borate buffer, a phosphate buffer, a citrate buffer, an organic buffer such as HEPES (1-piperazineethane sulphonic acid) or also a TRIS (tris(hydroxymethyl)aminoethane) buffer, preferably a citrate buffer for use in detecting aldehydes.

The surfactant can include sodium decyl sulfate, sodium dodecyl sulfate ("SDS"), sodium tetradecyl sulfate and Standapol ES-1, with SDS including the C10, C12 and C14 version of SDS is preferable. Trition X-100, Ninate 11, Georpon 71, Tetraonic 1357, Cremapor-el, Chemal la-9, Silwet L7900, Surfynly468, Surfactant 10G, and Tween 80 might also be used but they did not provide good results with the preferred elution solution, the CCM 1-hexanal and mPDA.

In the absence of SDS the polymerization and aldehyde response as discussed below is severely inhibited. mPDA is highly water soluble and the presence of SDS may provide a scaffold for organizing and orientating mPDA into a matrix to facilitate the polymerization reaction.

The solvent can include an aqueous solution of EtOH, MeOH, propanol, and isopropanol, with 15% EtOH preferred.

The molar ratio of salt concentration to phenylene diamine concentration is important. Generally the ratio should range from 0.03 to 0.5. For the CCM 1-hexanal, a molar ratio of mPDA to NaCl of 0.165 was found to provide optimal response.

The temperature for practicing the method of the present invention preferably ranges from 15 to 35° C., with 25 to 30° C. more preferred.

For the aldehydes such as 1-hexanal, one preferred embodiment of the elution solution comprises 33 mM NaCl, 50 mM Citrate, pH 2.5, 15% EtOH, and 0.2% SDS. Other preferred elution solutions include 50 mM Citrate, pH2.5, 15% propanol and 0.4% sodium decyl sulfate.

Using the elution solution containing a phenylene diamine derivative, the CCM is eluted into the phenylene diamine solution to form a fluorescing solution. The CCM and the mPDA react to form a fluorogenic species, the presence of which in the fluorescing solution is detected by measuring the fluorescence emitted by the fluorogenic species in the fluorescing solution.

The aldehyde content is quantitated by monitoring the signal rise (end-point) and/or rate of signal change (kinetic) which varies as a function of aldehyde concentration for a given mPDA concentration, and comparing such data with a carbonyl population sample of the breath. In practice the impact of carbonyls other than the selected carbonyl must be filtered out. There are two general assay format or detection modes. They are generically described as end-point and kinetic. In an end-point assay the system is incubated for a set time and the signal read. The signal at that point reflects the amount of analyte in the system. For a positive assay, the greater the concentration of the analyte, the greater the signal increase. In a kinetic assay the rate of change is monitored for a set duration. The rate of change is correlated to the amount of analyte. Preferably the end-point assay is employed with the present invention.

Assay measurements can be made on a typical fluorescence spectrometer including conventional scanning spectrometer, plate-reader or LED/diode based spectrometer following standard assay practices. To illustrate, the data displayed in FIG. 31 was acquired by mixing a total of 2 mL of the reaction solution and aldehyde into a standard fluorescence cuvette and measuring the intensity increase using an LED/diode spectrometer at particular time slices to simulate an end-point determination. The LED/diode spectrometer utilized consisted of an Ocean Optics Jazz spectrometer with LED source and diode detection coupled via fiber optics to a Qpod-e (Quantum Northwest) temperature controlled fluorescence sample holder. The 405 nm excitation was produced with a violet LED (volts: 3.3 V, I: 0.03 A). The signal was detected using a ILX-5118 diode detection with emission set at 495-505 nm band pass and 250 msec integration. Like most fluorescence based assays, optimal settings are dependent upon the throughput and stray light rejection characteristics of the spectrometer used and must be empirically determined for each instrument.

In one preferred embodiment, the phenylene diamine derivative reacts with the CCM in solution to produce a fluorescence emitting or fluorogenic species. It is believed that the phenylene diamine derivative oxidatively couples to the CCM and the phenylene diamine derivative polymerizes to dimers, trimers, oligomers and/or polymers. It is not clear if the CCM actually becomes part of the growing polymer, although the polymerization is modulated by the presence of CCM and there is a dose response.

The process of using a CCM to polymerize the phenylene diamine derivative may be described as dispersion polymerization. Poly-phenylene diamines have been used to construct nanostructures and colloidal dispersions of different shapes, tubes, spheres and the like. However, if the polymerization results in large high molecular weight structures then precipitation occurs in the solution, which, in the present invention, may handicap optical detection. Thus the ingredients used in the method of the present invention must be chosen to avoid having elements in the fluorescing solution that inhibit detection and quantitation of the CCM.

The present invention utilizes the ability of CCM to modulate (initiate, catalyze and accelerate) the oxidative coupling and polymerization of phenylene diamine derivatives to detect and quantitate trace aldehydes, ketones and carbonyl containing analytes in a biological sample. Oxidative coupling and polymerization of phenylene diamine generates chromophoric and fluorogenic species. In the case of mPDA and aldehydes, the formation of polymers or multimers gives rise to a broad optical absorbance band at 405 nm and an associated emission band at 505 nm. The monomer absorbance is found in the UV region <350 nm. As a result the production of the polymer can be conveniently followed by either conventional absorbance or fluorescence spectroscopy. In this regard, it should be appreciated that the absorbance and emission bands may vary depending upon the CCM and phenylene diamine derivative chosen, but all such bands useful in practicing this invention are part of the invention.

Figure 31:
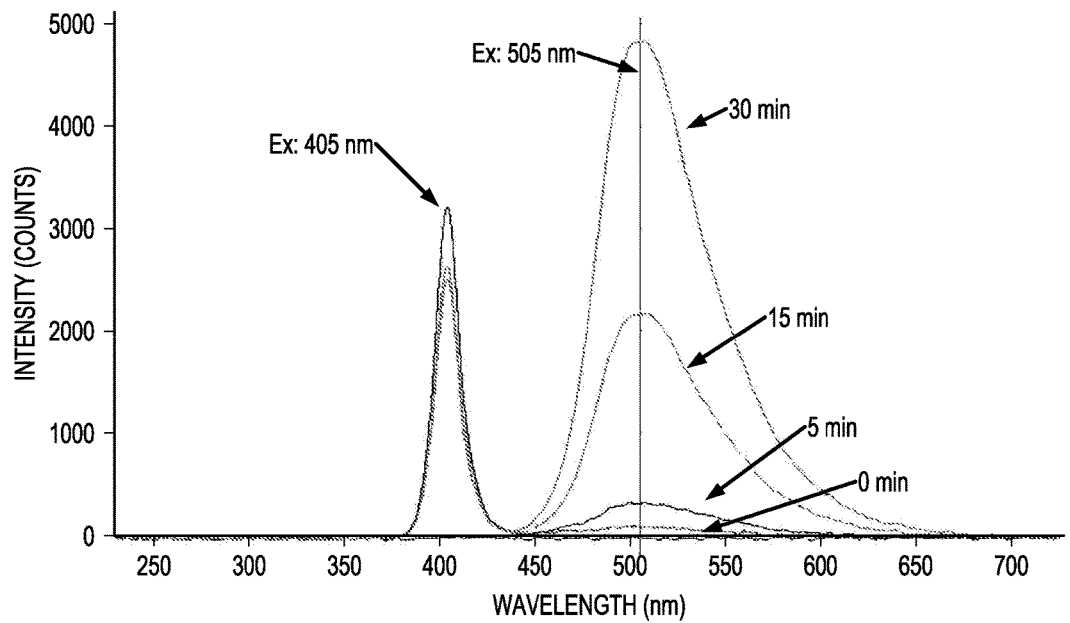
FIG. 31 shows graphs depicting the emission spectrum of the reaction of mPDA with 1-hexanal as a function of time.

For example, with reference to FIG. 31, the emission spectrum of the reaction of mPDA in the presence of 1 µM 1-hexanal as a function of time is shown. The conditions of the fluorescing solution are: 1 µM 1-hexanal, 5.4 mM mPDA, 33 mM NaCl, 50 mM citrate (pH 2.5), 15% EtOH, and 0.1% SDS. The emission increases dramatically as a function of time.

Figure 32:
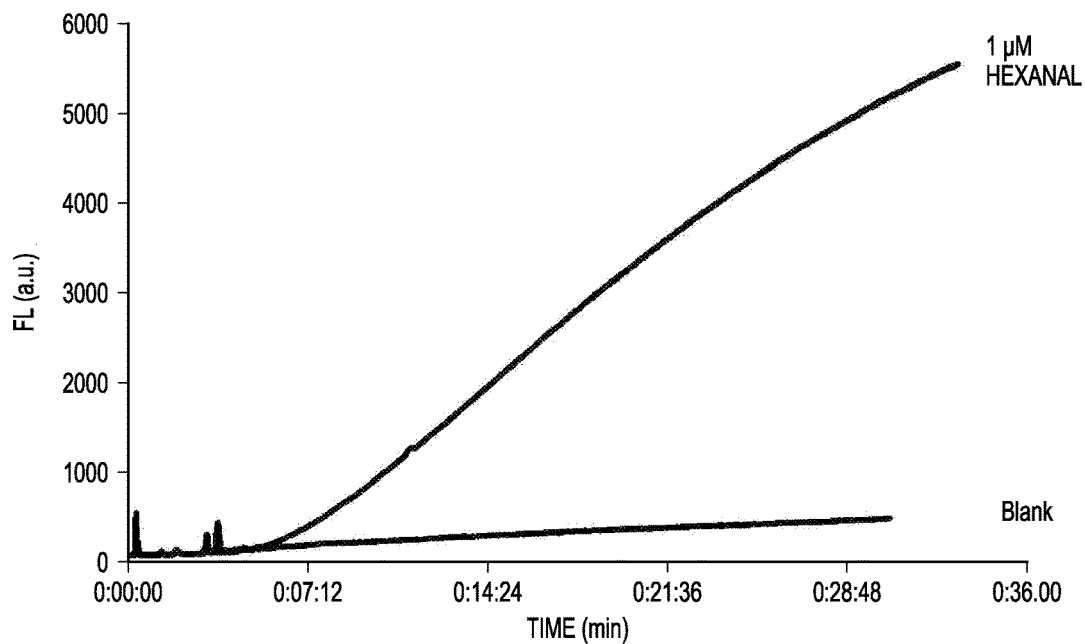
FIG. 32 shows a graph depicting the increase in fluorescence over time of the reaction of mPDA with 1-hexanal being the carbonyl containing moiety.

With reference to FIG. 32, the reaction and responses with and without aldehyde ("blank") are observed. The conditions of the fluorescing solution are: 1 µM 1-hexanal, 5.4 mM mPDA, 33 mM NaCl, 50 mM citrate (pH 2.5), 15% EtOH, and 0.1% SDS. The extent of the emission increase and the rate of increase are dependent upon the concentration of aldehyde in the phenylene diamine solution. At greater aldehyde concentrations, a larger and more rapid signal increase is observed. In the absence of aldehyde, the "blank" under goes a slow gradual small signal rise indicative of the slow polymerization of mPDA under the conditions examined. The polymerization is presumably due to the presence of trace oxidants such as iron, reactive oxygen species and other initiators. With the addition of a CCM, a significant signal enhancement over the blank or background is observed. Of particular note is that the rate of change is easily followed. As a result the detection system is amenable to both kinetic and end-point assay designs and detection modalities. The response can be quantitated at specific time points, e.g., 15 minutes (time slice) or by monitoring the slope as a function of aldehyde. The kinetic rate is slow enough that rapid and high precision of reactant additions is not required. The modulation of the polymerization reaction by a CCM such as an aldehyde and its use as a CCM quantitative sensor is another novel discovery and application described in this specification. Other alternatives including labeling, painting or tagging the CCM for subsequent analysis.

Figure 33A:
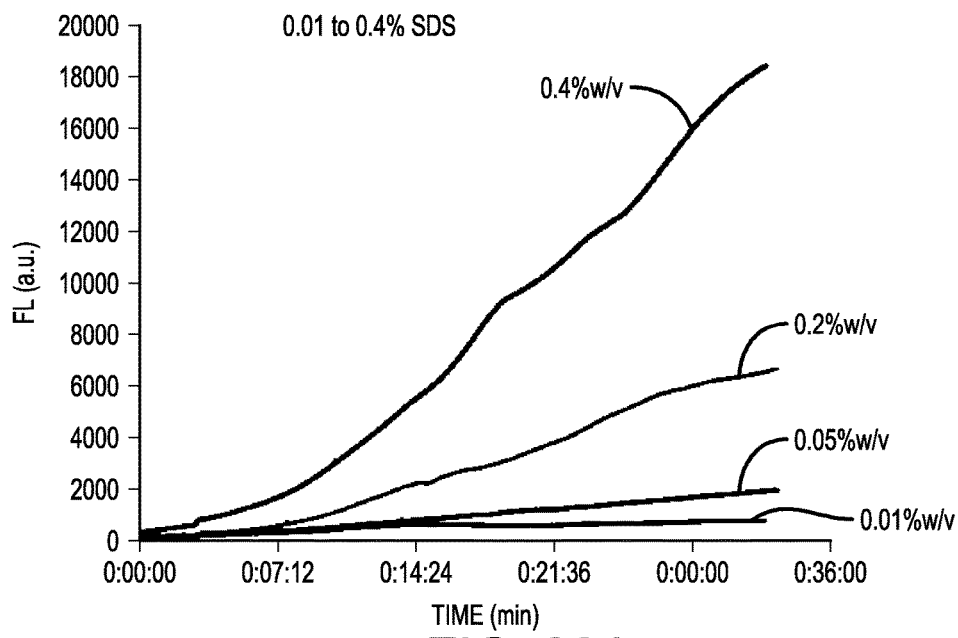
FIG. 33A shows a graph depicting the increase in fluorescence over time of the reaction with 1-hexanal as a function of sodium dodecyl sulfate ("SDS") concentration from 0.01 to 0.4% (w/v)
Figure 33B:
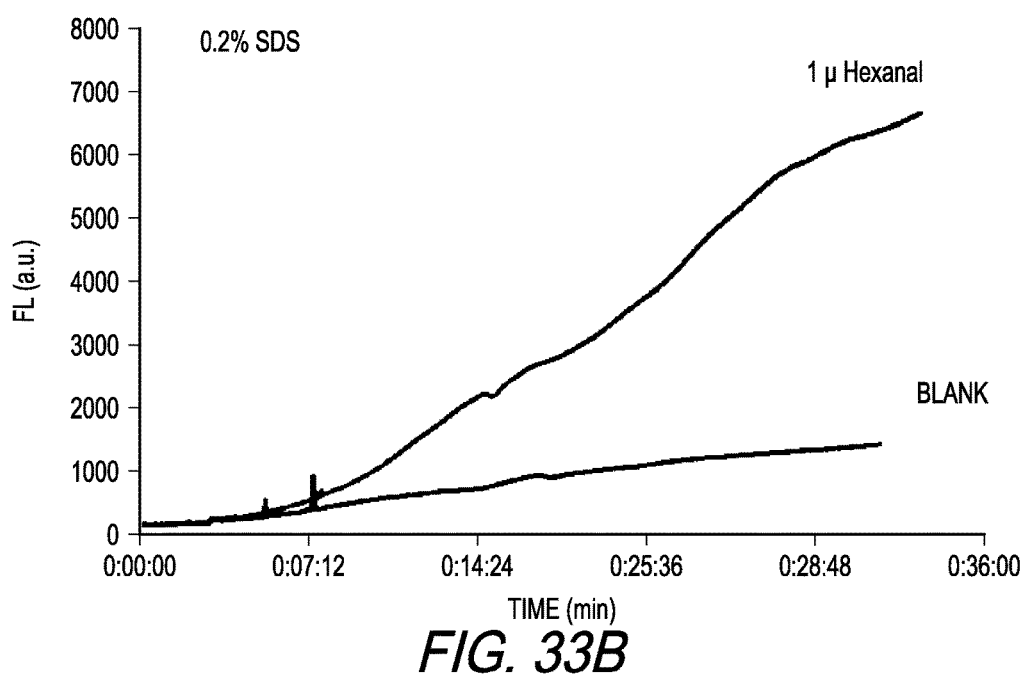
FIG. 33B shows a graph depicting the increase in fluorescence over time of reaction with 1-hexanal as compared to a blank, with SDS concentration at 0.2% SDS.
Figure 33C:
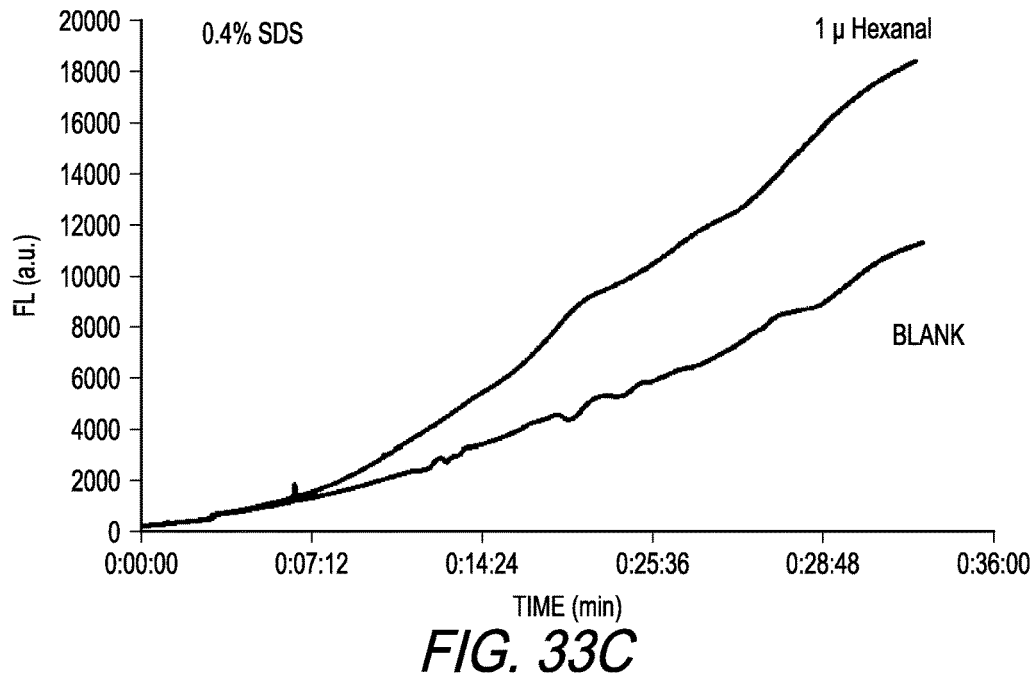
FIG. 33C shows a graph depicting the increase in fluorescence over time of the reaction with 1-hexanal as compared to a blank, with SDS concentration at 0.4% SDS.

With reference to FIGS. 33A, 33B and 33C, the CCM induced polymerization reaction with the phenylene diamine derivative is shown to be sensitive to environmental conditions, and components of the reaction system such as the concentration of SDS. The conditions of the fluorescing solution in these figures are: 1 µM 1-hexanal, 5.4 mM mPDA, 33 mM NaCl, 50 mM citrate (pH 2.5), and 15% EtOH. For example, the reaction and aldehyde assay performance is dependent upon salt content, mPDA content, surfactant, pH and temperature. Since the reaction involves a "quasi-phase" transition from monomer to polymer insufficient mPDA concentration yields a slow reaction with limited signal change. In contrast, a large excess of mPDA results in a very rapid reaction and the formation of insoluble precipitates that limit optical detection. In addition, a large excess results in increased background or "blank" signal.

With reference to FIG. 33A, the signal increases as function of SDS concentration. At an SDS concentration of 0.4%, the signal increase is almost 3 times the signal observed at 0.2%.

FIGS. 33B and 33C show a comparison of the aldehyde response versus the blank for 0.2% SDS and 0.4% SDS, respectively. The increase in SDS concentration also results in an increase in "blank" or background signal. Both the signal and background are modulated by SDS concentration and the optimized SDS concentration cannot be determined by monitoring the signal response alone. As a result the SDS concentration must be optimized to provide the greatest discrimination between signal and background signal generation. For the embodiment specified, the optimal SDS concentration falls within a narrow concentration band, and small deviations can result in increased variability and limit the assay sensitivity.

Figure 34:
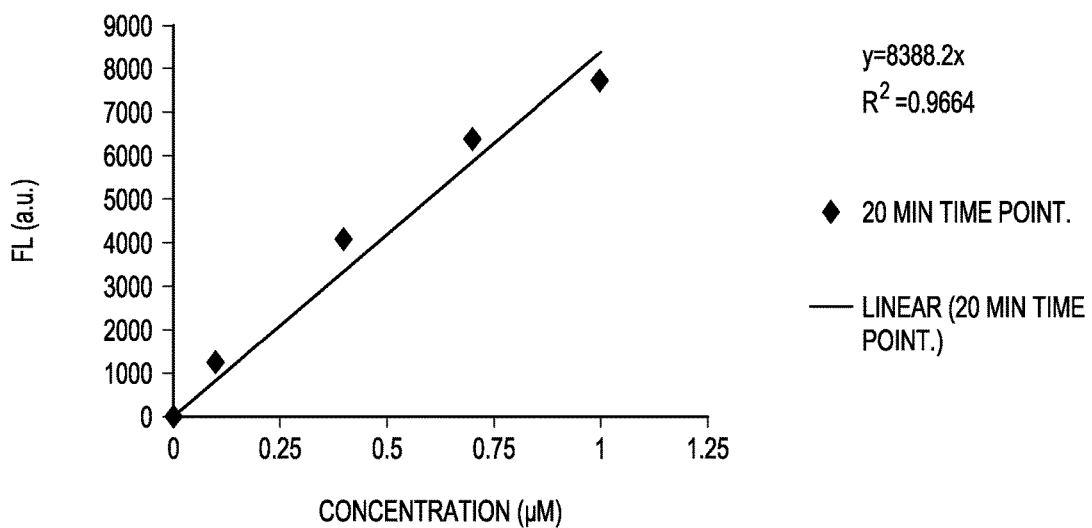
FIG. 34 shows a graph displaying fluorescence as a function of 1-hexanal concentration.

With reference to FIG. 34, the fluorescence response for mPDA as a function of 1-hexanal concentration is displayed, with the background corrected. A linear response is observed form 0.1 to 1 µM 1-hexanal. The data points are the average of triplicate samples. The signal is measured at 20 minutes after the aldehyde is added to the phenylene diamine solution. Under these conditions, 10.8 mM mPDA, 65.5 NaCl, 50 mM citrate (pH 2.5), 0.2% SDS at 25° C., a solution limit of detection (LOD) of 0.1 µM can be achieved.

Figures 35, 36:
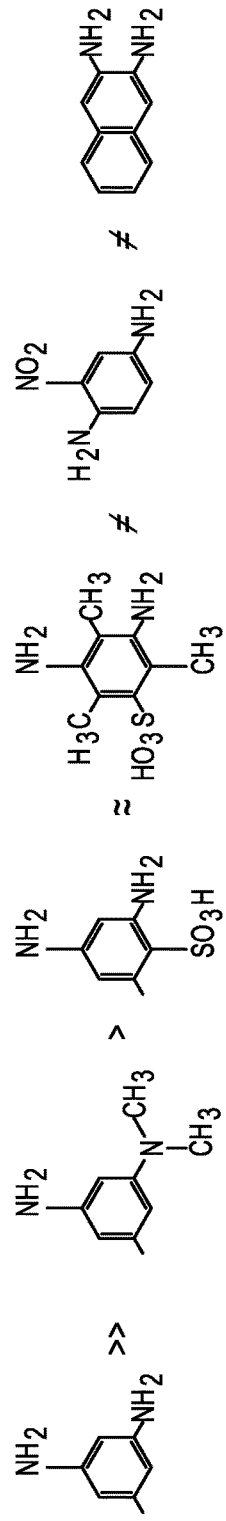
FIG. 35 shows a chart depicting the relative fluorescence as a function of aldehyde chain length.
FIG. 36 shows a chart depicting the relative fluorescence of selected small aromatic amines.

With reference to the chart in FIG. 35, mPDA exhibits a differential response for aliphatic aldehydes as a function of chain length. The chart reflects the fluorescence signal at 20 minutes after aldehyde addition, and the following conditions: 5.4 mM mPDA, 33 mM NaCl, 50 mM citrate (pH 2.5), 15% EtOH, and 0.1% SDS. The signal is measured at 20 minutes and this time-slice serves as pseudo end-point analysis method. For aliphatic aldehydes the relative response increases with aliphatic chain length. The response of acetylaldehyde is only 12% of the response observed for 1-hexanal. In contrast, the response of decyl ($C_{10}$) aldehyde is 30% greater than for 1-hexanal.

The nature of the aromatic diamine is also important to consider in employing the method of the present invention. O-PDA is highly reactive and undergoes rapid general oxidation. The high reactivity of o-PDA precludes its use as an aldehyde sensor in the preferred embodiment of the present invention. With reference to FIG. 36, the relative fluorescence response of a subset of diamines is displayed and illustrates the influence of both position and electronic effects on the aldehyde fluorescence response. Traditional aromatic electron donating and withdrawing effects should modulate the reactivity and susceptibility of the phenylene diamine derivative toward polymerization. An aldehyde response was not observed for both nitrophenylenediamine and naphthalenediamine under the preferred conditions, even when exposed to excess aldehyde. It has been found that aldehyde detection is based on the modulation of the polymerization of the reaction. If the molecule chosen is highly reactive and easily induced to polymerization then general oxidants can stimulate the reaction process and may limit its utility as a sensor. On the other hand, if the molecule is "too" stabilized, the polymerization process becomes inhibited and cannot be adequately stimulated by aldehyde and will require a much stronger oxidant to yield a response.

The present invention discussed above also includes a device for employing the method of the present invention. The device comprises a breath chamber preferably made of plastic and having a substrate in the breath chamber. The substrate is made from the materials discussed above and preferably silica. The substrate supports a carbonyl containing moiety from an animal's breath, e.g. aldehydes. The device also includes a fluid chamber. The fluid chamber includes an aqueous solution comprising an alcohol (e.g., 15% EtOH), a salt (e.g., NaCl), a surfactant (e.g., SDS), and a buffer (e.g. citrate). The solution can also comprise a phenylene diamine derivative such as mPDA.

The following example demonstrates one way to use the present invention to determine whether the sample breath of a human contains measurable aldehyde concentration and the concentration of the aldehyde in the breath. Employing the methodology discussed above, a series of fluorescence measurements are preformed to provide standards for various specific aldehydes and mixtures thereof that are known to be contained in a human breath sample (a population), and standards for concentrations of such various standards and mixtures thereof. Using these standards, the presence in a sample of human breath of a particular aldehyde or mixture of aldehydes and the concentration of such particular aldehyde or mixture of aldehydes can be determined. In general in one embodiment, the steps are as follows:

a. Capturing the aldehydes from the human breath sample on silica;
b. Forming a solution comprising a salt, a buffer, a surfactant in an alcohol in mildly acidic conditions;
c. Adding a phenylene diamine derivative to the solution of step b;
d. Eluting the captured aldehydes into the solution of step c;
e. Determining the fluorescence signal of the solution of step c;
f. Determining the fluorescence signal of the solution of step d;
g. Subtract the fluorescence signal from step e from the fluorescence signal from step f; and
h. Comparing the net resulting fluorescence signal from step g with standard fluorescence of known aldehydes (a calibration curve, i.e., a response to known concentrations via an assay) to determine the concentration of aldehydes in the fluorescing solution. Simply put, this is a comparison of "y" axis values to provide the "x" axis value, or alternatively, solve of x knowing y and the calibration function y=f(x).

In another embodiment of the present invention, the substrate can be pre-loaded with an active reactive capture agent which covalently attaches to the CCM (the "Agent") including without limitation a fluorescent hydrazine or aminooxy compound. Some examples of aminooxy compounds are as follows: aminooxy 5(6) tetramethylrhodamine (aminooxy 5(6) TAMRA), with a single isomer of either 5 or 6 preferred; and aminooxy 5(6) carboxyfluorescein (aminooxy 5(6) FAM), with a single isomer of either 5 or 6 preferred, for example aminooxy-05-5-FAM. Others include aminooxy 7-amino-3-acetyl-4 methylcourman-6-sulfonic acid; 5-aminoxy acetic acid rhodamine B; and dinitrophenylhydrazin. In the foregoing examples, the reactive group is specified without the linkage group, which would be well known to those of skill in the art. In addition to the foregoing, the hydrazine or hydrazide versions are included within the present invention. Preferably the Agent is somewhat polar.

For example, for a substrate consisting of 200 mg of 50-270 mesh (300-50 µm) particle with a bed diameter of 12.5 mm, the amount of the Agent can be from 5.5 mg to 0.1 mg, and preferably from 2.5 mg to 0.4 mg.

In yet another embodiment of the present invention, a two-solution methodology is used. After the substrate is loaded with the CCM, the CCM is eluted into a first elution solution or "rinse" solution comprising generally 30% ethanol and preferably 50 mM citrate, 30% ethanol at ph 2.5. The Agent is added to the rinse solution thereby resulting in painted CCM. This solution is then passed through another substrate, preferably a silica frit stack, to capture the painted CCM. The painted CCM is then eluted from the substrate with the painted CCM captured therein using a second elution solution or "rinse" solution comprising greater than 50% acetonitrile and preferably 90% ethanol. One of the benefits of this second embodiment is that a baseline reading is not necessary to remove noise.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further any specific numbers noted herein are only examples: alternative implementations may employ differing values or ranges.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further, any specific numbers noted herein are only examples: alternative implementations may employ differing values, measurements or ranges. It will be appreciated that any dimensions given herein are only exemplary and that none of the dimensions or descriptions are limiting on the present invention.

The teachings of the disclosure provided herein can be applied to other systems, not necessarily the system described above. The elements and acts of the various embodiments described above can be combined to provide further embodiments.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

These and other changes can be made to the disclosure in light of the above Detailed Description of the Preferred Embodiments. While the above description describes certain embodiments of the disclosure, and describes the best mode contemplated, no matter how detailed the above appears in text, the teachings can be practiced in many ways. Details of the system may vary considerably in its implementation details, while still being encompassed by the subject matter disclosed herein. As noted above, particular terminology used when describing certain features or aspects of the disclosure should not be taken to imply that the terminology is being redefined herein to be restricted to any specific characteristics, features or aspects of the disclosure with which that terminology is associated. In general, the terms used in the following claims should not be construed to limit the disclosures to the specific embodiments disclosed in the specification unless the above Detailed Description of the Preferred Embodiments section explicitly defines such terms. Accordingly, the actual scope of the disclosure encompasses not only the disclosed embodiments, but also all equivalent ways of practicing or implementing the disclosure under the claims.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A breath capture assembly comprising:
 a handle assembly that includes an elongated main body portion that defines a handle interior,
 a cap disposed at an end of the main body portion that includes a pressure opening defined therein, and
 a pressure transducer disposed in the handle interior, and
 an analysis cartridge received on an upper end of the handle assembly,
  wherein the analysis cartridge includes a main body portion that includes an upper portion that defines a breath chamber, and a lower portion that defines a fluid chamber,
  wherein the breath chamber includes a breath entry opening, a breath exit opening and a breath path therebetween, and a filter assembly that is movable along a filter assembly path between a first position and a second position,
  wherein the filter assembly has an opening defined therethrough, and
  wherein in the first position, the opening partially defines the breath chamber and is part of the breath path and in the second position the opening partially defines the fluid chamber.

2. The breath capture assembly of claim 1 wherein a pressure measurement hole is defined in a wall of the upper portion of the analysis cartridge, wherein the pressure measurement hole communicates the breath chamber with a pressure tunnel that extends through the main body portion, and wherein a pressure path is defined from the breath chamber, through the pressure measurement hole, the pressure tunnel, the pressure opening and to the pressure transducer.

3. The breath capture assembly of claim 2 wherein the cap of the handle assembly includes a pressure protrusion extending upwardly therefrom that is sealingly received in a pressure recess in the analysis cartridge, wherein the pressure recess is in communication with the pressure tunnel, and wherein the pressure opening is defined in the pressure protrusion.

4. The breath capture assembly of claim 2 wherein a hollow extension extends downwardly from the cap of the handle assembly and into the handle interior, and wherein the hollow extension is part of the pressure path.

5. The breath capture assembly of claim 4 further comprising a pressure tube that is received on the hollow extension and is in the pressure path between the hollow extension and the pressure transducer.

6. The breath capture assembly of claim 1 wherein the cap includes a seat defined therearound, and wherein a collar depending downwardly from the analysis cartridge is received on the seat.

7. The breath capture assembly of claim 6 wherein the cap includes an attachment protrusion extending radially outwardly therefrom, and wherein the attachment protrusion is received in an attachment recess defined in the collar of the analysis cartridge.

8. The breath capture assembly of claim 1 wherein the breath chamber is sealed from the fluid chamber.

9. The breath capture assembly of claim 8 wherein the analysis cartridge includes a breakable barrier disposed between the breath chamber and the fluid chamber when the filter assembly is in the first position to seal the breath chamber from the fluid chamber.

10. The breath capture assembly of claim 1 wherein the filter assembly includes first and second filters positioned in the opening, wherein the first and second filters define a substrate space therebetween, and wherein a carbonyl containing moiety capture material is disposed in the substrate space.

11. The breath capture assembly of claim 10 wherein the carbonyl containing moiety capture material is silica.

12. The breath capture assembly of claim 1 wherein the analysis cartridge includes a phenylene diamine derivative disposed therein.

13. The breath capture assembly of claim 12 further comprising an ampule member having a fluorescence chromophore space with the phenylene diamine derivative disposed therein, wherein the fluid chamber includes an elution solution disposed therein, wherein the ampule member is movable between a first position where the phenylene diamine derivative is separated from the elution solution and a second position where the phenylene diamine derivative is disposed in the elution solution.

14. The breath capture assembly of claim 13 wherein the phenylene diamine derivative is m-phenylene diamine.

15. The breath capture assembly of claim 12 wherein the phenylene diamine derivative is m-phenylene diamine.

* * * * *